US011738079B2

(12) United States Patent
Gowans et al.

(10) Patent No.: US 11,738,079 B2
(45) Date of Patent: Aug. 29, 2023

(54) ZIKA VIRUS VACCINE

(71) Applicant: THE UNIVERSITY OF ADELAIDE, Adelaide (AU)

(72) Inventors: Eric James Gowans, Prahran (AU); Branka Grubor-Bauk, Broadview (AU); Danushka Wijesundara, St. Lucia (AU)

(*) Notice: Subject to any disclaimer, the term of this patent is extended or adjusted under 35 U.S.C. 154(b) by 0 days.

(21) Appl. No.: 17/262,580

(22) PCT Filed: Jul. 23, 2019

(86) PCT No.: PCT/AU2019/050770
§ 371 (c)(1),
(2) Date: Jan. 22, 2021

(87) PCT Pub. No.: WO2020/019024
PCT Pub. Date: Jan. 30, 2020

(65) Prior Publication Data
US 2021/0228704 A1    Jul. 29, 2021

(30) Foreign Application Priority Data
Jul. 23, 2018  (AU) ............................... 2018902659

(51) Int. Cl.
*A61K 39/12* (2006.01)
*A61P 31/14* (2006.01)
*A61K 39/00* (2006.01)

(52) U.S. Cl.
CPC .............. *A61K 39/12* (2013.01); *A61P 31/14* (2018.01); *A61K 2039/53* (2013.01); *A61K 2039/572* (2013.01); *A61K 2039/575* (2013.01)

(58) Field of Classification Search
None
See application file for complete search history.

(56) References Cited

U.S. PATENT DOCUMENTS 8,513,005 B2 * 8/2013 Hooper ................. A61K 39/12
435/320.1

FOREIGN PATENT DOCUMENTS

| CN | 107987136 | | 5/2018 |
| CN | 108210921 | A | 6/2018 |
| WO | WO 2009/046388 | A1 | 4/2009 |
| WO | WO 2017/132210 | | 8/2017 |
| WO | WO 2017/140905 | | 8/2017 |
| WO | WO 2017/144173 | | 8/2017 |
| WO | WO 2017/147458 | | 8/2017 |
| WO | WO 2017/197477 | | 11/2017 |
| WO | WO 2017/200008 | | 11/2017 |
| WO | WO 2018/020271 | | 2/2018 |
| WO | WO 2018/053478 | A1 | 3/2018 |
| WO | WO 2018/237313 | | 12/2018 |

OTHER PUBLICATIONS

Pattnaik et al., Vaccine, 2020, 8(266), 19 pages. (Year: 2020).*
Dar et al., "Prediction of promiscuous T-cell epitopes in the Zika virus polyprotein: An in silico approach," *Asian Pacific Journal of Tropical Medicine*, vol. 9, No. 9, pp. 844-850, 2016.
Liu et al., "Construction and Identification of Recombinant HEK293T Cell Lines Expressing Non-structural Protein 1 of Zika Virus," *International Journal of Medical Sciences*, vol. 14, No. 11, pp. 1072-1079, 2017.
Viranaicken et al., "Recombinant Zika NS1 Protein Secreted from Vero Cells Is Efficient for Inducing Production of Immune Serum Directed against NS1 Dimer," *International Journal of Molecular Sciences*, 19:38, 2018 (13 pages).
Bailey et al., "Antibodies Elicited by an NS 1-Based Vaccine Protect Mice against Zika Virus," *mBio*, 10(2):e02861-18, 2019 (16 pages).
Extended European Search Report dated Mar. 21, 2022, for corresponding EP Appl. No. 19839807.5 (10 pages).
Grubor-Bauk et al., "NS1 DNA vaccination protects against Zika infection through T cell mediated immunity in immunocompetent mice," *Science Advances*, 5(12):eaax2388, 2019 (28 pages).
Kudchodkar et al., "Rapid response to an emerging infectious disease—Lessons learned from development of a synthetic DNA vaccine targeting Zika virus," *Microbes and Infection*, 20:676-684, 2018.

* cited by examiner

*Primary Examiner* — Stacy B Chen
(74) *Attorney, Agent, or Firm* — Klarquist Sparkman, LLP

(57) ABSTRACT

The present disclosure relates to vaccines and methods for the prevention and treatment of Zika virus infection. Particularly, the present disclosure relates to viral and DNA vaccine vectors which includes or encode for secreted immunogenic peptides of NS1 that eliciting a protective immune response and prevent Zika virus infection of a subject.

19 Claims, 21 Drawing Sheets

Specification includes a Sequence Listing.

Figure 1

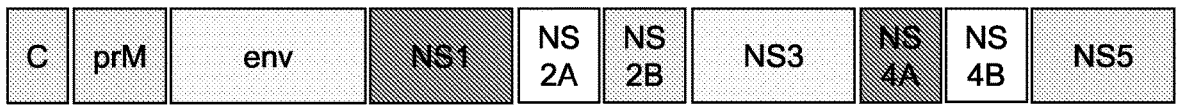

Figure 2

| SEQ ID NO: | | | |
|---|---|---|---|
| 13 | YP_009227199.1 | DVGCSVDFSKKETRCGTGVFIYNDVEAWRDRYKYHPDSPRRLAAAVKQANEEGICGISSV | 60 |
| 14 | AMX81916.1 | DVGCSVDFSKKETRCGTGVFVYNDVEAWRDRYKYHPDSPRRLAAAVKQANEDGICGISSV | 60 |
| 15 | ALU33341.1 | DVGCSVDFSKKETRCGTGVFVYNDVEAWRDRYKYHPDSPRRLAAAVKQANEDGICGISSV | 60 |
| 16 | AUI42289.1 | DVGCSVDFSKKETRCGTGVFVYNDVEAWRDRYKYHPDSPRRLAAAVKQANEDGICGISSV | 60 |
| 17 | AMR39834.1 | DVGCSVDFSKKETRCGTGVFVYNDVEAWRDRYKYHPDSPRRLAAAVKQANEDGICGISSV | 60 |
| | | ****************** .************************** .******* | |
| 13 | YP_009227199.1 | SRMENIMWKSVEGELNAILEENGVQLTVVVGSVKNPMWRGPQRLPVPVNELPHGWKAWGK | 120 |
| 14 | AMX81916.1 | SRMENIMWRSVEGELNAILEENGVQLTVVVGSVKNPMWRGPQRLPVPVNELPHGWKAWGK | 120 |
| 15 | ALU33341.1 | SRMENIMWRSVEGELNAILEENGVQLTVVVGSVKNPMWRGPQRLPVPVNELPHGWKAWGK | 120 |
| 16 | AUI42289.1 | SRMENIMWRSVEGELNAILEENGVQLTVVVGSVKNPMWRGPQRLPVPVNELPHGWKAWGK | 120 |
| 17 | AMR39834.1 | SRMENIMWRSVEGELNAILEENGVQLTVVVGSVKNPMWRGPQRLPVPVNELPHGWKAWGK | 120 |
| | | ******* .*************************************************** | |
| 13 | YP_009227199.1 | SYFVRAAKTNNSFVVDGDTLKECPLEHRAWNSFLVEDHGFGVFHTSVWLKVREDYSLECD | 180 |
| 14 | AMX81916.1 | SYFVRAAKTNNSFVVDGDTLKECPLKHRAWNSFLVEDHGFGIFHTSVWLKVREDYSLECD | 180 |
| 15 | ALU33341.1 | SHFVRAAKTNNSFVVDGDTLKECPLKHRAWNSFLVEDHGFGVFHTSVWLKVREDYSLECD | 180 |
| 16 | AUI42289.1 | SYFVRAAKTNNSFVVDGDTLKECPLKHRAWNSFLVEDHGFGVFHTSVWLKVREDYSLECD | 180 |
| 17 | AMR39834.1 | SYFVRAAKTNNSFVVDGDTLKECPLKHRAWNSFLVEDHGFGVFHTSVWLKVREDYSLECD | 180 |
| | | * .**********************.************.************ | |
| 13 | YP_009227199.1 | PAVIGTAVKGREAAHSDLGYWIESEKNDTWRLKRAHLIEMKTCEWPKSHTLWTDGVEESD | 240 |
| 14 | AMX81916.1 | PAVIGTAVKGKEAVHSDLGYWIESEKNDTWRLKRAHLIEMKTCEWPKSHTLWTDGIEESD | 240 |
| 15 | ALU33341.1 | PAVIGTAVKGKEAVHSDLGYWIESEKNDTWRLKRAHLIEMKTCEWPKSHTLWTDGIEESD | 240 |
| 16 | AUI42289.1 | PAVIGTAAKGKEAVHSDLGYWIESEKNDTWRLKRAHLIEMKTCEWPKSHTLWTDGIEESD | 240 |
| 17 | AMR39834.1 | PAVIGTAAKGKEAVHSDLGYWIESEKNDTWRLKRAHLIEMKTCEWPKSHTLWTDGIEESD | 240 |
| | | ******* .** .** .************************************** .**** | |
| 13 | YP_009227199.1 | LIIPKSLAGPLSHHNTREGYRTQVKGPWHSEELEIRFEECPGTKVYVEETCGTRGPSLRS | 300 |
| 14 | AMX81916.1 | LIIPKSLAGPLSHHNTREGYRTQMKGPWHSEELEIRFEECPGTKVHVEETCGTRGPSLRS | 300 |
| 15 | ALU33341.1 | LIIPKSLAGPLSHHNTREGYRTQMKGPWHSEELEIRFEECPGTKVHVEETCGTRGPSLRS | 300 |
| 16 | AUI42289.1 | LIIPKSLAGPLSHHNTREGYRTQMEGPWHSEELEIRFEECPGTKVHVEETCGTRGPSLRS | 300 |
| 17 | AMR39834.1 | LIIPKSLAGPLSHHNTREGYRTQMKGPWHSEELEIRFEECPGTKVHVEETCGTRGPSLRS | 300 |
| | | *********************** . .**************** .*************** | |
| 13 | YP_009227199.1 | TTASGRVIEEWCCRECTMPPLSFRAKDGCWYGMEIRPRKEPESNLVRSMVTA | 352 |
| 14 | AMX81916.1 | TTASGRVIEEWCCRECTMPPLSFRAKDGCWYGMEIRPRKEPESNLVRSMVTA | 352 |
| 15 | ALU33341.1 | TTASGRVIEEWCCRECTMPPLSFRAKDGCWYGMEIRPRKEPESNLVRSMVTA | 352 |
| 16 | AUI42289.1 | TTASGRVIEEWCCRECTMPPLSFRAKDGCWYGMEIRPRKEPESNLVRSMVTA | 352 |
| 17 | AMR39834.1 | TTASGRVIEEWCCRECTMPPLSFRAKDGCWYGMEIRPRKEPESNLVRSMVTA | 352 |
| | | *************************************************** | |

*P ≤ 0.05; P ≤ 0.01; *P ≤ 0.001

IgG2a anti-NS1 Titre Day 58

Day 63

*P ≤ 0.05
**P ≤ 0.01
***P ≤ 0.001

*P ≤ 0.05; P ≤ 0.01; *P ≤ 0.001

*P ≤ 0.05; P ≤ 0.01; *P ≤ 0.001

Pool 3 Peptides

Pool 4 Peptides

Pool 4 Peptides

P ≤ 0.01; *P ≤ 0.001

P ≤ 0.01; **P ≤ 0.0001 ns = not significant; *P ≤ 0.05; P ≤ 0.01; *P ≤ 0.001, ****P ≤ 0.0001

ZIKA VIRUS VACCINE

PRIORITY CLAIM

This application is the § 371 U.S. National Stage of International Application No. PCT/AU2019/050770, filed Jul. 23, 2019, which was published in English under PCT Article 21(2), which in turn claims priority from Australian provisional application number 2018902659 filed on 23 Jul. 2018, the entire contents of which is herein incorporated by reference.

TECHNICAL FIELD

The present invention relates to the field of vaccines and pharmaceutical compositions for prevention, treatment and diagnosis of Zika virus infection.

Specifically, the present invention provides methods, DNA vaccines, viral vectors and isolated peptides, which can be used in preventing, treating and diagnosing Zika infections in humans and other animals.

BACKGROUND OF INVENTION

Zika virus is an arbovirus and member of the Flaviviridae family of viruses. It is primarily spread in tropical and sub-tropical areas by mosquitos. Zika virus was first documented in 1947, with the first document human infection in 1952.

Typically, individuals infected with Zika virus are either asymptomatic or present with a low-grade fever, mild headache, rash and joint pain. In the majority of cases, an infected individual is not diagnosed due to the mild nature of the symptoms, and to date Zika virus has not been documented to cause mortality in infected adult individuals.

However, Zika infection has been linked to Guillain-Barré syndrome, an autoimmune disease which results in immune-mediated damage to the myelin sheaths surrounding the axon of peripheral nerves, and results in muscle weakness and abnormal function of the autonomous nervous system.

Despite its mild nature, in 2016 Zika virus was identified as a causative agent in several deleterious central nervous system malformation in fetuses. Vertical transmission from infected mothers to fetuses in utero has been shown to lead to both growth restriction, and central nervous system complication such as microcephaly Studies indicate that the rate of adverse pregnancy outcomes when the mother was positive for an active Zika infection during pregnancy were over four times higher compared to non-infected individuals (Brasil, P. et al., N Engl J Med. 2016, 375:2321-2334). However, these results were from developing nations with a distinctly high rate of adverse pregnancy outcomes in the control group (uninfected group). Consequently, the rate of adverse outcomes in Zika affected pregnancies is likely to be higher in other populations. Further, infants born from Zika infected mothers presented with an eight times higher rate of abnormalities upon clinical examination, including microcephaly (Brasil, P. et al.—supra).

The endemic mosquito hosts for Zika have primarily limited transmission to inhabitants and visitors to equatorial-tropical and subtropical areas. However, it has recently been discovered that Zika virus can be sexually transmitted, with infectious virions existing in semen for months after acute infection. Consequently, the World Health organisation (WHO) recommends that men abstain from trying to conceive with their partners for six-month after exposure to Zika affected areas.

Resultantly, there is a need to effectively prevent Zika viral infection and transmission, primarily in pregnant women attempting to, or likely to, conceive, as well as their partners.

The most common means to prevent viral infection is to vaccinate individuals. The fundamentals of vaccination are theoretically simple. A host is provided with an antigen derived from a virus which elicits an immune response. This immune response ultimately resolves, but in the process generates populations of memory immune cells (T cells and B cells) which are antigenically-experienced. Upon a subsequent exposure to the antigen, the memory cells elicit a rapid immune response which prevents, or limits, the infection from establishing in the host thereby preventing morbidity. The ideal vaccine induces a strong response from the immune system, gives long-term protection with few doses, and causes few side effects. While the theory behind vaccination is simple, in practice the development of vaccines is considerably more difficult.

Vaccines which are presently in clinical use generally fall into one of the following categories: (i) Live attenuated viruses, which are viruses that have been treated to reduce their virulence; (ii) inactivated (killed) viruses; (iii) recombinant subunit viruses which includes a specific antigenic subunit of a virus, and (iv) Toxoid viruses, which contain an inactivated toxin and protect against toxin damage, rather than an infection per se.

Of the types of vaccines, the most successful to date have been the live attenuated virus vaccines, due to their strong antigenic nature, and large array of antigens. However, these types of virus have considerable health risks as the attenuated virus, may form an active infection, and may be transmissible.

Consequently, recombinant and subunit viruses are becoming more popular. These vaccines use either one particular antigen from an infectious agent, or multiple antigens, to elicit an immune response. However, these vaccines are limited by the ability to select the best antigen, or more often a series of antigens, and to modify the antigens (fold and glycosylate) in the correct manner. When selecting antigens for subunit vaccines, the most promising antigens are the surface antigens of an infectious agent. Surface antigens are ideal candidates as they are easily accessible to immune mediators such antibodies.

Despite vaccines having a long history, there is no set process for developing a vaccine. Each infectious agent interacts with the immune system in different ways, and in many cases there are diverse but related strains which have differing antigens, or the antigens may change over time (antigen drift). As such, the selection of the "type" of vaccine, and the antigen contained within the vaccine, needs to be tailored for each infection agent.

There are a range of vaccines that have already been developed for a number of members of the Flaviviridae family.

A Yellow fever vaccine was first developed in 1938 and is currently, implemented in the infant vaccination program of 35 of the 44 countries deemed at a high risk of yellow fever infection. The vaccine is an attenuated-virus, which provides strong immunity, despite posing risks to those having compromised immune systems.

Dengue virus has proved to be significantly more difficult to vaccinate against. There are four major strains of dengue that have similar, but antigenically distinct, sequences. As such, immunity to one strain has failed to provide significant protection against other strains. In fact, it has been noted that a previous infection with one strain of Dengue virus leads to considerably more sever outcomes when an individual is infected with a second, different, strain of Dengue. This is also likely to be a problem when immunised with a single strain, or even multivalent vaccines. As a result, the current vaccine is only recommended for patients who have already had a previous Dengue viral infection.

It is though that the mechanism by which immunity to one strain of Dengue causes more severe infection when exposed to another strain is attributable to a process of Antibody Dependent Enhancement of Infection (ADEI). The proposed model of ADEI relates to pre-existing antibodies (from a previous infection or vaccination) that bind to surface antigens on the second virus. Fc Receptors on the monocytes bind to the pre-existing antibodies, which are then internalised together with the bound Dengue virus. This internalisation of the virus into a host cell facilitates infection of the monocyte (Whitehead, S. et al. Nat. Rev Micro. 5, 518-528 (2007).

Several attempts to prepare a vaccine against Zika virus have been published in the art. WO2017/109225 A1 discloses a Zika virus particle which was inactivated by formaldehyde treatment. WO2017/192856 A1, WO2018/020271 A1 and WO2018/052549 A1 all related to vaccines comprising varying vectors that include structural proteins primarily the Envelope (env) protein or premembrane (prM) protein.

Two vaccines against Zika virus are presently in clinical trials. One of these includes an inactive virus and is based on the same platform used for West Nile virus (another member of the Flaviviridae family). The other vaccine includes a genetically altered live attenuated virus, which is based on the platform use to develop the Dengue virus vaccine. However, there is a potential risk that all of the above vaccines may induce ADEI is a similar manner to the Dengue virus vaccine.

Therefore, there is a need to develop a vaccine that induces protection against Zika virus infection, which is easy to manufacture and stable to store, and is unlikely to cause potentiation of infections with other Flaviviridae or subsequent Zika virus exposure.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed before the priority date of each claim of this application.

SUMMARY OF INVENTION

The present inventors have identified that a non-structural protein of Zika virus, NS1, can elicit a protective immune response in a mammalian model, which can prevent or minimise Zika virus infection. It has been found by the Inventors that native NS1 protein, when expressed in isolation, does not elicit or instigate a significant or protective immune response in a mammalian subject. However, and importantly, operatively linking the NS1 protein, or a peptide thereof, to a signalling peptide which facilitates secretion from a mammalian cell does elicits an immune response and provides protection from Zika virus infection.

Accordingly, the present invention provides a vaccine for administering to a mammal, the vaccine including: an immunogenic peptide having at least 70% sequence homology to a portion of the non-structural protein 1 (NS1 protein) of Zika virus, the immunogenic peptide operatively linked to a heterologous signal peptide; or a nucleic acid molecule encoding an immunogenic peptide having at least 70% sequence homology to a portion of the non-structural protein 1 (NS1 protein) of Zika virus, the immunogenic peptide operatively linked to a heterologous signal peptide, wherein the immunogenic peptide is at least 7 amino acids in length and the immunogenic peptide is secreted from a mammalian cell.

In some embodiments, the immunogenic peptide has at least 75%, at least 80%, at least 85%, at least 90%, at least 95%, at least 98%, at least 99% or 100% sequence homology to a portion of the non-structural protein 1 (NS1 protein) of Zika virus, across the length of the immunogenic peptide.

In some embodiments, the present invention provides a nucleic acid molecule including: a nucleic acid encoding at least an immunogenic portion of a sequence homologous to the non-structural protein 1 (NS1) of Zika virus; and an operatively linked nucleic acid encoding a heterologous signal peptide.

The sequence of Zika virus NS1 is disclosed in the art. Indeed the NS1 protein sequence varies depending on the specific strain of Zika virus, and such variations should be considered, by those skilled in the art, to fall within the invention described herein. However, in some embodiments, the non-structural protein 1 sequence has at least 60%, at least 65%, at least 70%, at least 75%, at least 80%, at least 85%, at least 90%, at least 92%, at least 94%, at least 96%, at least 98%, at least 99%, at least 99.4%, or at least 99.7% homology to the sequence set forth in SEQ ID NO: 1.

In some embodiments of the present invention, the immunogenic peptide has at least 70% at least 75%, at least 80%, at least 85%, at least 90%, at least 95%, at least 98%, at least 99% or 100% sequence homology to a portion of the Zika virus NS1 protein sequence set forth in SEQ ID NO: 1.

The present inventors have identified that NS1, when linked to a heterologous signal peptide induces an immune response including T cells activation (both T helper cells, and cytotoxic T lymphocytes), as well as the activation of B cells and the subsequent secretion of anti-NS1 protein antibodies. Therefore, in some embodiments, the immunogenic portion of the sequence homologous to NS1 of Zika virus elicits one or more of a T-helper response, and/or a cytotoxic-T-cell response and/or a B-cell response. In some embodiments, the immunogenic peptide elicits a T-cell response. In some embodiments, the immunogenic peptide elicits at least a T-helper response and/or a cytotoxic-T-cell response.

Epitope analysis of the NS1 protein by the Inventors identified four amino acid sequences that elicit immune T helper and CTL responses in vaccinated hosts. These sequences correspond to positions 204 to 221 (specifically 204 to 218 and 207 to 221) and 261 to 278 (specifically 261 to 275 and 264 to 278) of NS1 (e.g. SEQ ID NO: 1). Of particular relevance are the two overlapping portions of these sequences, namely sequence corresponding to positions 207 to 218 and positions 264 to 275. As such, and while not wanting to be bound by theory, these sequences, and in particular the overlapping regions, likely contain epitopes that are presented by major histocompatibility molecules (MHC) to T cells. As will be appreciated by those in the art, MHC-class I has a peptide binding groove which is closed at both ends. As such, the size of the peptide presented by MHC-class I is limited to ranges from about 8 amino acids to about 10 amino acids in length, although evidence suggests that peptides from 7 amino acids up to 15 amino acids can be accommodated. However, it appears that the optimal length for presentation by MHC-class I is 9 amino acids in length. In comparison, MHC-class II has an open ended binding groove and therefore can typically accommodate peptides 13 to 15 residues in length. However, some shorter peptides (such as peptides 7 amino acids in length) can also be presented and elicit and immune response.

The positions of the identified epitope regions correspond to the C-terminal beta ladder domain of NS1, spanning from positions 172 to 352. Therefore, in some embodiments the immunogenic peptide, or immunogenic portion, has sequence homology to a portion (preferably a contiguous portion) spanning from positions 172 to 352 of NS1.

Consequently, in some embodiments, the immunogenic peptide or immunogenic portion has sequence homology to a portion of the NS1 protein located from position 172 to 352, or from position 172 to 278, or from position 204 to 278, or from position 204 to 352, or from position 204 to 218, or from position 207 to 218, or from position 204 to 221, or from position 207 to 221, or from position 261 to 275, or from position 261 to 278, or from position 264 to 275, or from position 264 to 278.

Consequently, in some embodiments, the immunogenic portion is up to 12 amino acids in length, or up to 15 amino acids in length, or up to 74 amino acids in length, or up to 107 amino acids in length, or up to 149 amino acids in length, or up to 183 amino acids in length, or is the full length NS1 protein.

As will be demonstrated below, the Inventors have demonstrated that non-structural protein 1 can be presented by MHC molecules to T cells, thereby eliciting an immune response. As such, it is proposed that immunogenic portions of the NS proteins, being at least 7 amino acids in length, are immunogenic and can be used in a vaccination regimen for treating and/or preventing Zika virus infection.

Despite, MHC only binding short peptides (typically 8 to 15 residues, as described above), longer proteins are processed within antigen presenting cells and digested to shorter peptide sequences which can be loaded onto MHC molecules. Therefore, the immunogenic peptides of the present invention can be considerably longer than 8 amino acid residues and can be up to the full length of the non-structural proteins.

Therefore, in some embodiments the immunogenic peptide, or immunogenic portion, is at least 8 amino acids in length, at least 9 amino acids in length, at least 10 amino acids in length, at least 11 amino acids in length, at least 12 amino acids in length, at least 13 amino acids in length, at least 14 amino acids in length, at least 15 amino acids in length, at least 16 amino acids in length, at least 17 amino acids in length, at least 18 amino acids in length, at least 19 amino acids in length, at least 20 amino acids in length, at least 22 amino acids in length, at least 24 amino acids in length, at least 26 amino acids in length, at least 28 amino acids in length, at least 30 amino acids in length, at least 35 amino acids in length, at least 40 amino acids in length, at least 45 amino acids in length, at least 50 amino acids in length, at least 55 amino acids in length, at least 60 amino acids in length, at least 65 amino acids in length, at least 69 amino acids in length, at least 70 amino acids in length, at least 75 amino acids in length, at least 80 amino acids in length, at least 85 amino acids in length, at least 90 amino acids in length, at least 95 amino acids in length, at least 100 amino acids in length, at least 110 amino acids in length, at least 120 amino acids in length, at least 130 amino acids in length, at least 140 amino acids in length, at least 150 amino acids in length, at least 160 amino acids in length, at least 170 amino acids in length, at least 180 amino acids in length, at least 183 amino acids in length, at least 190 amino acids in length, at least 200 amino acids in length, at least 210 amino acids in length, at least 250 amino acids in length, at least 260 amino acids in length, at least 300 amino acids in length, at least 310 amino acids in length, at least 350 amino acids in length, or is the full length NS1 protein. In some of the above embodiments the immunogenic peptide has sequence homology to the amino acid sequence set forth in SEQ ID NO: 1 or SEQ ID NO: 2 or SEQ ID NO: 3

In some embodiments, the immunogenic peptide, or immunogenic portion, is up to 351 amino acids in length, or up to 300 amino acids in length, or up to 250 amino acids in length, or up to 200 amino acids in length, or up to 181 amino acids in length, or up to 150 amino acids in length, or up to 100 amino acids in length, or up to 80 amino acids in length, or up to 60 amino acids in length, or up to 50 amino acids in length, or up to 40 amino acids in length, or up to 30 amino acids in length, or up to 20 amino acids in length, or up to 18 amino acids in length, or up to 16 amino acids in length, or up to 14 amino acids in length, or up to 12 amino acids in length, or up to 10 amino acids in length, or up to 8 amino acids in length.

In some embodiments, the immunogenic peptide or immunogenic portion has at least 70% sequence homology to a portion of at least 7, 8, 9, 10, 11 or 12 contiguous amino acids of the NS1 protein of Zika virus, preferably the sequence set forth in SEQ ID NO: 1. In some embodiments, the immunogenic peptide or immunogenic portion has at least 70% sequence homology to a portion of at least 7, 8, 9, 10, 11 or 12 contiguous amino acids of SEQ ID NO: 2 and/or SEQ ID NO: 3

In some embodiments of the vaccine for administering to a mammal, the sequence of the nucleic acid molecule, which encodes the immunogenic peptide (or immunogenic portion) and/or the heterologous signal peptide, is codon optimised. In preferred embodiments of the nucleic acid molecule encoding an immunogenic peptide having at least 70% sequence homology to a portion of the non-structural protein 1 of Zika virus, the nucleic acid molecule includes a codon optimised nucleic acid sequence, which encodes the immunogenic portion of the NS1 protein. In some embodiments, the codon optimised nucleic acid, which encodes the immunogenic portion of the NS1 protein has the sequence set forth in SEQ ID: NO: 4.

The immunogenic peptide or portion of the present invention is secreted when expressed in a mammalian cell. As such, the heterologous signal peptide is a signal peptide which facilitates secretion of the operatively linked peptide from a mammalian cell. In some embodiments, the signal peptide directs translocation of the operatively linked immunogenic portion NS1 to the endoplasmic reticulum, the cell membrane, the proteasome, the lysosome or directs the immunogenic portion of NS1 to specific cell types or cell subsets.

In some embodiments, the heterologous signal is selected from the group consisting of: tissue plasminogen activator (tPA) signal sequence, erythropoietin (epo) signal sequence, VP22 HSV1 signal sequence, Parathyroid hormone-related protein (PTHrP) N-terminal ER signal, Calreticulin (CRT), or Adenovirus E3 signal sequence or a flavivirus signal sequence including structural proteins (e.g. capsid (C), envelope (E), or premembrane (prM) proteins).

In some embodiments, the signal sequence includes, or consists of, a target sequence which targets the encoded product to a desired cell type or cellular subset and may facilitate secretion or localisation of the operatively linked portion of NS1. In some embodiments, the target sequence targets the operatively linked portion of NS1 to an immune cell. In some embodiments, the target sequence targets the operatively linked portion of NS1 to an antigen presenting cell. In some embodiment, the target sequence targets the encoded product to the proteasome of a host cell. In some embodiments, the target sequence targets the operatively linked portion of NS1 to the endosome or lysosome of a host cells.

In some embodiments, the heterologous signal peptide is a tissue plasminogen activator (tPA) signal peptide. The tPA signal peptide sequence is known in the art. However, in some embodiments the heterologous signal peptide has 80%, 85%, 90%, 95% or 100% sequence homology to the sequences set forth in SEQ ID NO: 5 or SEQ ID NO: 12. In some embodiments, the nucleic acid encoding the signal peptide is at least 80%, 85%, 90%, 95%, 98%, 99% or 100% sequence homology to the sequence set forth in SEQ ID NO: 6. In some embodiments, the heterologous signal peptide has not an immunoglobulin (Ig) signalling peptide. In some embodiments, the signal peptide is not an IgE signalling peptide In some embodiments, the nucleic acid includes a sequence homologous to, or identical to, the sequence set forth in SEQ ID NO: 7.

In some embodiments, the nucleic acid molecules includes a promotor which is constitutive in a mammalian cell. In some embodiments, the promoter is selected from the group of CMV, SV40, UBC, EF1A, PGK or CAGG. In some embodiments, the promoter is derived from cytomegalovirus (CMV).

In some embodiments, the nucleic acid molecule includes a DNA vector, the vector including a nucleic acid encoding an immunogenic portion of a sequence homologous to NS1, as described herein, and a nucleic acid encoding the heterologous signal peptide, as described herein. In some embodiments, the DNA vector is the pVax 1 vector.

In some embodiments of the vaccine of the present invention, the vaccine includes: a DNA vector including the nucleic acid molecule encoding the immunogenic peptide and the operatively linked heterologous signal peptide: or a viral vector including: the immunogenic peptide and the operatively linked heterologous signal peptide; or the nucleic acid molecule encoding the immunogenic peptide and the operatively linked heterologous signal peptide.

Further provided is a pharmaceutical composition including a vaccine as described herein; and a pharmaceutically acceptable excipient, carrier or solvent.

The present invention further provides an isolated immunogenic peptide for eliciting a T cell immune response in a subject, the immunogenic peptide having at least 70% sequence homology to a portion of the non-structural protein 1 (NS1 protein) of Zika virus, wherein the peptide is at least 7 amino acids in length.

In some embodiments, the isolated immunogenic peptide not the full length NS1 protein of Zika virus. In some embodiments, the isolated immunogenic peptide is up to 351 amino acids in length, or up to 300 amino acids in length, or up to 250 amino acids in length, or up to 200 amino acids in length, or up to 181 amino acids in length, or up to 150 amino acids in length, or up to 100 amino acids in length, or up to 80 amino acids in length, or up to 60 amino acids in length, or up to 50 amino acids in length, or up to 40 amino acids in length, or up to 30 amino acids in length, or up to 20 amino acids in length, or up to 18 amino acids in length, or up to 16 amino acids in length, or up to 14 amino acids in length, or up to 12 amino acids in length, or up to 10 amino acids in length, or up to 8 amino acids in length.

In some embodiments, the immunogenic peptide is at least 8 amino acids in length, at least 9 amino acids in length, at least 10 amino acids in length, at least 11 amino acids in length, at least 12 amino acids in length, at least 14 amino acids in length, at least 16 amino acids in length, at least 18 amino acids in length, at least 20 amino acids in length, at least 22 amino acids in length, at least 24 amino acids in length, at least 26 amino acids in length, at least 28 amino acids in length, at least 30 amino acids in length, at least 35 amino acids in length, at least 40 amino acids in length, at least 45 amino acids in length, at least 50 amino acids in length, at least 55 amino acids in length, at least 60 amino acids in length, at least 65 amino acids in length, at least 69 amino acids in length, at least 70 amino acids in length, at least 75 amino acids in length, at least 80 amino acids in length, at least 85 amino acids in length, at least 90 amino acids in length, at least 95 amino acids in length, at least 100 amino acids in length, at least 110 amino acids in length, at least 120 amino acids in length, at least 130 amino acids in length, at least 140 amino acids in length, at least 150 amino acids in length, at least 160 amino acids in length, at least 170 amino acids in length, at least 180 amino acids in length, at least 183 amino acids in length, at least 190 amino acids in length, at least 200 amino acids in length, at least 210 amino acids in length, at least 250 amino acids in length, at least 260 amino acids in length, at least 300 amino acids in length, at least 310 amino acids in length, at least 350 amino acids in length, or is 351 amino acids in length.

In some embodiment of the isolated immunogenic peptide, the portion of the NS1 protein is a portion of SEQ ID NO: 1 from position 172 to 352, or from position 172 to 278, or from position 204 to 278, or from position 204 to 352, or from position 204 to 218, or from position 207 to 218, or from position 204 to 221, or from position 207 to 221, or from position 261 to 275, or from position 261 to 278, or from position 264 to 275, or from position 264 to 278.

In some embodiments of the isolated immunogenic peptide, the immunogenic peptide has at least 70% sequence identity to 7, 8, 9, 10, 11 or 12 contiguous amino acids from the sequence set forth in SEQ ID NO: 1 or SEQ ID NO:2 and/or SEQ ID NO: 3. In some embodiments, the immunogenic peptide consisting of the sequence set forth in SEQ ID NO:2 and/or the sequence set forth in SEQ ID NO: 3.

When measuring the sequence identity of the immunogenic peptide compared to NS1 (or any of the sequences referred to herein), the percentage of sequence identity should be measure across the length of the immunogenic peptide (unless specified otherwise, or unless the context requires otherwise). Therefore, in some embodiments, the isolated immunogenic peptide has at least 70%, at least 75%, at least 80%, at least 85%, at least 90%, at least 95%, at least 98%, at least 99% or 100% sequence homology to a portion of the non-structural protein 1 (NS1 protein) of Zika virus across the length of the immunogenic peptide.

In some embodiments, the immunogenic peptide has 1, 2, 3 or 4 insertions, mutations or deletions when compared to a sequence of at least 6, 7, 8, 9, 10, 11 or 12 contiguous amino acids from the sequence set forth in SEQ ID NO: 1, and/or the sequence set forth in SEQ ID NO:2 and/or the sequence set forth in SEQ ID NO: 3. In some embodiments, the immunogenic peptide consists of the sequence set forth in SEQ ID NO:2 and/or the sequence set forth in SEQ ID NO: 3.

The present invention also provides a composition including an isolated immunogenic peptide as described herein.

Further, the present invention provides a method of eliciting an immune response in a subject. In some embodiments, the method includes the step of: administering to the subject an immunogenic agent, wherein the immunogenic agent is a nucleic acid molecule as described herein, a vaccine as described herein, a pharmaceutical composition as described herein, an isolated immunogenic peptide as described herein, or a composition as described herein.

In some embodiments, the immune response is a T cell response. In some embodiments, the T cell response is the generation of ZIKA NS1-specific CD8+ T cells and/or CD4+ T cells. In some embodiments, the T cell immune response results in ZIKA NS1 memory T cells.

In some embodiments, the T cells response is elicited in response to an immunogenic portion spanning from positions 172 to 352 of NS1.

In some embodiments, the immune response is a B cell response. In some embodiments, the B cell response results in the generation of ZIKA anti-NS1 antibodies. In some embodiments, the B cell immune response results in ZIKA NS1 memory B cells.

In some embodiments of the method of eliciting an immune response, the immunogenic agent is administered in a single dose, in two doses, in three doses, in four doses, or in five doses. In some embodiments, the immunogenic agent is administered via a parenteral route, including an intravenous route, a subcutaneous route, an intradermal route, or an intramuscular route.

Also provided by the present invention is the use of a nucleic acid molecule as described herein, a vaccine as described herein, a pharmaceutical composition as described herein, an immunogenic peptide as described herein, or a composition as described herein, for eliciting an immune response in a subject or in the preparation of a medicament for the prevention or treatment of a Zika virus infection.

Moreover, the present invention provides a nucleic acid molecule as described herein, a vaccine as described herein, a pharmaceutical composition as described herein, an immunogenic peptide as described herein, or a composition as described herein, for use in preventing or treating a Zika virus infection.

The present invention also provides a method of producing an anti-Zika NS1 protein antibody comprising: administering to a subject a nucleic acid molecule as described herein, a vaccine as described herein, a pharmaceutical composition as described herein, an immunogenic peptide as described herein, or a composition as described herein; isolating serum from the subject; and purifying an antibody from the serum.

Also provided is a method of producing an anti-Zika NS1 protein antibody comprising: administering to a subject a nucleic acid molecule as described herein, a vaccine as described herein, a pharmaceutical composition as described herein, an immunogenic peptide as described herein, or a composition as described herein; isolating B cells from the subject; fusing the isolated B cells to immortalised cells to prepare a hybridoma; culturing the hybridoma in a medium; and purifying an antibody from the culture medium.

The present invention additionally provides a method of detecting a Zika virus infection comprising, administering to a subject, or an in vitro sample from a subject, an anti-NS1 protein antibody generated in accordance with the methods for generating an antibody described herein, or generated using an immunogenic peptide or nucleic acid encoded herein.

Additionally, the present invention provides a method of detecting Zika virus-specific T-cells including the steps of; administering to a subject, or an in vitro sample from a subject, an isolated immunogenic peptide as described herein, and detecting the binding of the isolated immunogenic peptide to T-cells in the subject or the sample. In some embodiments, the immunogenic peptide is administered together with an MHC molecule. In some embodiments, the immunogenic peptide is administered together with multiple MHC molecules, in some embodiments the multiple MHC molecules are oligomerized, or biotinylated, or administered in the form of a tetramer, heptamer or a dextran bound molecule.

BRIEF DESCRIPTION OF DRAWINGS

For a further understanding of the aspects and advantages of the present invention, reference should be made to the following detailed description, taken in conjunction with the accompanying drawings.

FIG. 1—Schematic illustration of Zika virus genome.

FIG. 2—Alignment of the reference amino acid sequence of Zika virus and 4 characterised strains.

FIG. 3—pVax 1 vector structure.

FIG. 4—DNA vaccine design for control, wtNS1, tPA-NS1 and NS1 heptamer ("heptamer").

FIG. 5—Vaccine dosing and blood sampling protocol.

FIGS. 6A-6D—Immunoglobulin G (IgG) titres after administering four DNA vectors across eight weeks.

FIG. 7—IgG2a titre at day 58 post vaccination in control, tPA-NS1, wtNS1 and NS1 heptamer vaccinated mice.

FIG. 8—IgG dose response to tPA-NS1 vaccination.

FIGS. 9A-9D—Interferon gamma (IFNg) production from T cells when pulsed with varying NS1 peptides.

FIG. 10—In vivo CTL killing of targets pulsed with pooled peptides of NS1 in mice vaccinated with control, wtNS1, tPA-NS1 or heptamer DNA vectors.

FIG. 11—In vivo CD69 expression of B220+ splenocytes from mice administered cells pulsed with pooled peptides of NS1 in mice vaccinated with control, wtNS1, tPA-NS1 or heptamer DNA vectors.

FIG. 12—In vivo CTL killing of targets pulsed with individual 10 mer to 15 mer peptides of NS1 from Pool 3.

FIG. 13—In vivo CTL killing of targets pulsed with individual 10 mer to 15 mer peptides of NS1 from Pool 4 in mice vaccinated with tPA-NS1.

FIG. 14—In vivo CD69 expression of B220+ splenocytes in mice administered cells pulsed with individual 10mer to 15 mer peptides of NS1 from Pool 3.

FIG. 15—In vivo CD69 expression of B220+ splenocytes in mice administered cells pulsed with individual 10 mer to 15 mer peptides of NS1 from Pool 4.

FIG. 16—Exemplary ELISpot of IFNg release from cells isolated from vaccinated mice in response to pooled peptides with, or without, peptides 87 and 88 and in response to peptides 68 and 69.

FIGS. 17A-17C—Quantified IFNg release from cells isolated from vaccinated mice in response to pool 4 peptides, peptides 87 and 88 and peptides 68 and 69.

FIGS. 18A-18C—Quantified IFNg release from cells isolated from vaccinated mice in response to pool 3 peptides, pool 4 peptides, peptides 87 and 88 and peptides 68 and 69 in mice vaccinated with tPA-NS1 and control DNA vectors.

FIG. 19—In vivo CTL killing dose response to peptides 87 and 88 in mice vaccinated with control, wtNS1, tPA-NS1 or heptamer DNA vectors.

FIG. 20—In vivo CD69 expression of B220+ splenocytes in response to increasing doses of peptides 68 and 69 in mice vaccinated with control, wtNS1, tPA-NS1 or heptamer DNA vectors FIG. 21—Histograms of binding of serum antibodies from tPA-NS1, pVax, heptamer and wtNS1 DNA vaccinated mice compared to commercial anti-ZIKA NS1 antibodies.

FIG. 22—Antibody titres in mice administered 50 μg or 100 μg of tPA-NS1 DNA vaccine or 100 μg pVax control DNA.

FIGS. 23A-23C—Viral titres on days 1, 3 and 7 in mice vaccinated with tPA-NS1 and control DNA vaccines.

FIGS. 24A-24C—Viral titres in days 1, 3 and 7 in mice following passive transfer of antibodies titre form tPA-NS1 vaccinated mice resulting in high (2.9 $\log_{10}$) or low (2.2 $\log_{10}$) antibody levels.

FIG. 25—Anti-NS1 IgG antibody titres on weeks 4, 6 and 8 in interferon α/β signalling deficient (IFNAR-/-) mice and Balb/c control mice following tPA-NS1 vaccination.

FIG. 26—Survival rate over time of IFNAR-/- mice vaccinated with either pVax (control) or tPA-NS1 following ZIKA virus challenge.

FIGS. 27A-27C—Viral titres on days 1(A), 3(B) and 7(C) in Balb/c mice vaccinated with pVax (control) or Balb/c mice depleted of either CD8+ cells and/or CD4+ cells and vaccinated with tPA-NS1 prior to ZIKA virus challenge.

FIGS. 28A-28B—Western blot of NS1 protein in cell lysates (A) and supernatants of cell cultures (B) administered tPA-NS1, pVax, heptamer and wtNS1 DNA vectors.

DETAILED DESCRIPTION

The nucleotide and polypeptide sequences referred to herein are represented by a sequence identifier number (SEQ ID NO:). A summary of the sequence identifiers is provided in Table 1. A sequence listing is also provided as part of the specification. Reference to a polynucleotide sequence (denoted as "SEQ ID NO:") also includes the complement sequence.

protein (NS1), which is not present on the Zika virion, can elicit a protective immune response in a mammalian subject when provided in the form of a secreted peptide. Therefore, the present invention provides, a vaccine for administering to a mammal, the vaccine including: an immunogenic peptide having at least 70% sequence homology to a portion of the non-structural protein 1 (NS1 protein) of Zika virus, the immunogenic peptide operatively linked to a heterologous signal peptide; or a nucleic acid molecule encoding an immunogenic peptide having at least 70% sequence homology to a portion of the non-structural protein 1 (NS1 protein) of Zika virus, the immunogenic peptide operatively linked to a heterologous signal peptide, wherein the immunogenic peptide is at least 7 amino acids in length and the immunogenic peptide is secreted from a mammalian cell.

In some embodiments the vaccine includes: a DNA vector including the nucleic acid molecule encoding the immunogenic peptide and the operatively linked heterologous signal peptide.

In some embodiments, the present invention provides a nucleic acid molecule including: a nucleic acid encoding at least an immunogenic portion of a sequence homologous to the non-structural protein 1 (NS1) of Zika virus; and an operatively linked nucleic acid encoding a heterologous signal peptide.

Vaccines comprising nucleic acid molecules have been shown to elicit strong humoral and cell-mediated immune responses in many animal models and humans. Studies demonstrate that DNA (administered alone or in a viral vector) is internalized by host cells, including local antigen-presenting cells (APCs), which then express and present the immunogenic proteins encoded by the DNA vector to cytotoxic lymphocytes (CTLs) or T helper cells. Further, other (non-antigen presenting) cells transfected with the DNA vector, can secrete the encoded antigen, which can be processed and presented by APCs, thereby eliciting an immune response in a way comparable to an active infection.

As such a vaccine including a nucleic acid molecule encoding an immunogenic peptide having at least 70%

TABLE 1

Table of Sequence Listings

| Sequence ID Number (SEQ ID) | length | Type | Description |
| --- | --- | --- | --- |
| SEQ ID NO: 1 | 352 | A.A | Zika Virus NS1 |
| SEQ ID NO: 2 | 12 | A.A | Epitope of position 207 to 218 of NS1 |
| SEQ ID NO: 3 | 12 | A.A | Epitope of position 264 to 275 of NS1 |
| SEQ ID NO: 4 | 1053 | D.N.A. | Codon optimized NS1 encoding sequence |
| SEQ ID NO: 5 | 23 | A.A | Tissue plasminogen activator (tPA) signal sequence |
| SEQ ID NO: 6 | 69 | D.N.A | Codon optimised sequence encoding SEQ ID NO: 5 |
| SEQ ID NO: 7 | 1122 | D.N.A | Codon optimised sequence encoding tPA operatively linked to NS1 |
| SEQ ID NO: 8 | 15 | A.A | Peptide 87 |
| SEQ ID NO: 9 | 15 | A.A | Peptide 88 |
| SEQ ID NO: 10 | 15 | A.A | Peptide 68 |
| SEQ ID NO: 11 | 15 | A.A | Peptide 69 |
| SEQ ID NO: 12 | 22 | A.A. | Tissue plasminogen activator (tPA) signal sequence of NCBI Reference Sequence: NP_000921.1 |

The Sequence Listing is submitted as an ASCII text file in the form of the file named 8222-105715-01_ST25.txt, which was created on Jun. 12, 2023, and is 50,323 bytes, which is incorporated by reference herein.

The present invention is predicated on the surprising findings by the inventors that the Zika virus non-structural 1 sequence homology to a portion of the non-structural protein 1 (NS1 protein) of Zika virus, the immunogenic peptide operatively linked to a heterologous signal peptide, has been shown to elicit a significant and protective immune response to Zika virus when the immunogenic peptide is secreted from a mammalian cell.

In some embodiments the vaccine includes a viral vector including: the immunogenic peptide and the operatively linked heterologous signal peptide; or the nucleic acid molecule (described herein) encoding the immunogenic peptide and the operatively linked heterologous signal peptide.

The Zika virus (ZIKV) genome consists of a single-stranded linear RNA molecule of approximately 10.7 kb (NCBI genome reference sequence NC_012532; NCBI protein reference sequence YP_002790881: exemplary strains; GenBank accession numbers KU321639, MG645981, KU955593, and KX051561, with genomic length varying depending on the strain) with 2 flanking non-coding regions (5' and 3' NCR) and a single long open reading frame. The RNA genome encodes a polyprotein as described in FIG. 1, comprising 5' Capsid (C)—precursor of membrane (prM)—Envelope (env)—Non-structural protein (NS) 1-NS2A-NS2B-NS3-NS4A-NS4B-NS5 3'. The genome encodes a polyprotein (YP_002790881), which is cleaved into 10 sub proteins (i.e. capsid, precursor membrane prM, envelope E and seven non-structural proteins (1, 2A, 2B, 3, 4A, 4B and 5)) (see; Cunha, M. S. et al., Genome. Announc., 4(2): e00032-16); Faye et al., PLoS Negl Trop. Dis. 8(1): e2636, 2014; and Chambers et al., Annu. Rev. Microbiol. 44:649-688, 1990).

The capsid, precursor membrane prM and envelope E proteins (the structural proteins), together with genomic RNA, form virions. The seven non-structural proteins are involved in viral replication and assembly as well as evasion of host immune responses (Xia, H. et al., Nat. Comm., 9: 414).

Non-Structural Protein 1

NS1 is approximately a 50-kD glycoprotein which is essential for RNA replication and immune evasion by flaviviruses, such as Zika. Zika virus has been shown to avoid host immune responses by antagonising type-1 IFN responses during infection of dendritic cells, while viral NS1 and NS4B function to (inter alia) inhibit type-1 IFN production by preventing TBK1 inhibition (Xia, H. et al. supra). Further, studies of NS1 proteins in other flaviviruses show that this protein elicits the generation of protective antibodies, further enhancing immune evasion (Hilgenfeld, R. EMBO J., 35(24) 2631-2633).

Flavivirus NS1 proteins have been shown to occur in vivo in three different forms: (i) ER membrane-associated NS1 homodimer, which has a critical role in viral RNA replication (ii) a plasma membrane—bound NS1 dimer; and (iii) secreted NS1 which forms a hexamer (trimer of dimers). It is the secreted form that has been shown to elicit protective antibodies in other flaviviruses, such as Dengue Virus (Hilgenfeld, R., supra). However, Zika NS1 has only been demonstrated to show and overall average sequence homology of 55% with dengue virus, and as such extrapolation of NS1 function in dengue virus (and other flaviviruses) should be done with caution (Freire, M. C. L. C et al., ACS Omega, 2(7):3913-3920; Hilgenfeld, R., supra). Indeed the outer surface of Zika secreted NS1 is markedly different from those of other flavivirus members including Dengue Virus type 2 and West Nile virus (Hilgenfeld, R., supra).

NS1 can be polymorphic between varying strains of Zika virus, however the majority of the NS1 protein sequence is conserved. FIG. 2 illustrated four exemplary characterised strains of Zika virus NS1, compared to the consensus sequence. As can be seen, of the 352 amino acids comprising the NS1 protein, only 13 polymorphic sites are indicated in FIG. 2. While a boarder comparison of NS1 from varying strains of Zika virus would likely reveal further polymorphisms, It is to be understood that these polymorphic forms of NS1 are envisaged within the scope of this invention. However, in some embodiments, the non-structural protein 1 sequence has at least 60%, at least 65%, at least 70%, at least 75%, at least 80%, at least 85%, at least 90%, at least 92%, at least 94%, at least 96%, at least 98%, at least 99%, at least 99.4%, at least 99.7% homology to the sequence set forth in SEQ ID NO: 1.

As illustrated in FIG. 2, and as discussed above, the NS1 protein sequence varies depending on the specific strain of Zika virus, and such variations should be considered by those skilled in the art to fall within the invention described herein. However in some embodiments, the sequence homologous to the NS1 protein of Zika virus has homology to the sequence set forth in SEQ ID NO: 1.

The terms "homology" and "homologous", as used herein in reference to a DNA or amino acid sequence, are to be construed in accordance with the definition of "Sequence Homology, Amino Acid" as defined by National Center for Biotechnology Information Medical Subject Headings (NCBI MeSH). As such, the term "homology" and "homologous", and the like, are to be interpreted as "the degree of similarity between sequences of amino acids or polynucleotides".

When a percentage of sequence homology is specified, in the context of two nucleic acid sequences or two polypeptide sequences, the percentage of homology generally refers to the alignment of two or more sequences across a portion of their length when, compared and aligned for maximum correspondence. Preferably, and unless stated otherwise, the homology is assessed over the specified length of the nucleic acid, polypeptide or portion thereof. In some embodiments, the homology is assessed over a specified portion of the length, or a functional portion (as specified herein, identified by methods provided herein, or as known in the art). Preferably, the percentage of sequence homology is determined over the entire length of the immunogenic peptide.

In some embodiments, where appropriate or specified, the sequence homology of polypeptides is assessed over a comparison window of at least 20 amino acid residues, at least 22 amino acid residues, at least 50 amino acid residues, at least 75 amino acid residues, at least 100 amino acid residues, at least 150 amino acid residues at least 200 amino acid residues, at least 250 amino acid residues, at least 300 amino acid residues, at least 352 amino acid residues, or at least 374 amino acid residues.

In some embodiments, where appropriate or specified, the sequence homology of polynucleotides is assessed over a comparison window of at least 66 residues, at least 90 residues, at least 150 residues, at least 225 residues, at least 300 residues, at least 600 residues, at least 900 residues, at least 1056 residues, or 1122 residues.

Alignment of sequences for assessment of sequence homology can be conducted by algorithms known in the art, such as the Basic Local Alignment Search Tool (BLAST) algorithm, which is described in Altschul et al, J. Mol. Biol. 215:403-410, 1990. A publically available, internet interface, for performing BLAST analyses is accessible through the National Center for Biotechnology Information. Additional known algorithms include those published in: Smith & Waterman, "Comparison of biosequences", Adv. Appl. Math. 2:482, 1981, Needleman & Wunsch, "A general method applicable to the search for similarities in the amino acid sequence of two proteins" J. Mol. Biol. 48:443, 1970; Pearson & Lipman "Improved tools for biological sequence comparison", Proc. Natl. Acad. Sci. USA 85:2444, 1988, or by automated implementation of these or similar algorithms.

Global alignment programs may also be used to align similar sequences of roughly equal size. Examples of global alignment programs include NEEDLE (available at www.ebi.ac.uk/Tools/psa/emboss_needle/) which is part of the EMBOSS package (Rice P et al., Trends Genet., 2000; 16: 276-277), and the GGSEARCH program fasta.bioch.virginia.edu/fasta_www2/fasta_www.cgi?rm=compare&pgm=gnw), which is part of the FASTA package (Pearson W and Lipman D, 1988, Proc. Natl. Acad. Sci. USA, 85: 2444-2448). Both of these programs are based on the Needleman-Wunsch algorithm which is used to find the optimum alignment (including gaps) of two sequences along their entire length. A detailed discussion of sequence analysis can also be found in Unit 19.3 of Ausubel et al ("Current Protocols in Molecular Biology" John Wiley & Sons Inc, 1994-1998, Chapter 15, 1998).

In some embodiments, the immunogenic peptide has at least 75%, at least 80%, at least 85%, at least 90%, at least 95%, at least 98%, at least 99% or 100% sequence homology to a portion of the non-structural protein 1 (NS1 protein) of Zika virus, across the length of the immunogenic peptide. In some embodiments, the non-structural protein 1 (NS1 protein) of Zika virus has 60%, 65%, 70%, 75%, 80%, 85%, 90%, 92%, 94%, 96%, 98%, 99%, 99.4%, 99.7% homology to the sequence set forth in SEQ ID NO: 1.

In some embodiments, the immunogenic portion is at least 6 amino acids in length, or at least 7 amino acids in length, or at least 8 amino acids in length, or at least 9 amino acids in length, or at least 10 amino acids in length, or at least 11 amino acids in length, or at least 12 amino acids in length.

In some embodiments, the immunogenic peptide is at least 8 amino acids in length, or at least 9 amino acids in length, or at least 10 amino acids in length, or at least 11 amino acids in length, or at least 12 amino acids in length.

The present inventors have identified that NS1 (or immunogenic portions thereof), when linked to a heterologous signal peptide, induces an immune response including T cells activation (both T helper cells, and cytotoxic T lymphocytes), as well as the activation of B cells and the subsequent secretion of anti-NS1 protein antibodies. Therefore, in some embodiments, the immunogenic peptide of the sequence homologous to NS1 of Zika virus elicits one or more of a T-helper response, and/or a cytotoxic-T-cell response and/or a B-cell response. In some embodiments, the immunogenic peptide elicits a T-cell response. In some embodiments, the immunogenic peptide elicits at least a T-helper response and/or a cytotoxic-T-cell response.

Epitope analysis of the NS1 protein by the Inventors identified four amino acid sequences that elicit immune T helper and CTL responses in vaccinated hosts. These sequences correspond to positions 204 to 221 (specifically 204 to 218 and 207 to 221) and 261 to 278 (specifically 261 to 275 and 264 to 278) of NS1 (e.g. SEQ ID NO: 1). Of particular relevance are the two overlapping portions of these sequences, namely sequence corresponding to positions 207 to 218 and positions 264 to 275. As such, and while not wanting to be bound by theory, these sequences, and in particular the overlapping regions, likely contain epitopes that are presented by major histocompatibility molecules (MHC) to T cells. As will be appreciated by those in the art, MHC-class I has a peptide binding groove which is closed at both ends. As such, the size of the peptide presented by MHC is limited and ranges from 8 to 10 amino acids in length, although evidence suggests that peptides from 7 amino acids up to 15 residues can be accommodated. However, it appears that the optimal length for presentation by MHC-class I is 9 amino acids in length. In comparison, MHC-class II has an open ended binding groove and therefore can typically accommodate peptides 13 to 15 residues in length. However, some shorter peptides (such as peptides 7 amino acids in length) can also be presented and elicit and immune response.

As will be appreciated in the art, all, or a portion of, the peptide presented by MHC molecules may be antigenic. Therefore, in some embodiments the immunogenic portion (corresponding to a portion of the immunogenic peptide) is at least 6, 7, 8, 9, 10, 11 or 12 contiguous amino acids from the amino acid sequence SEQ ID NO: 1. In some embodiments, the immunogenic portion includes at least 6, 7, 8, 9, 10, 11 or 12 contiguous amino acids from the amino acid sequence SEQ ID NO: 2 and/or SEQ ID NO: 3. In some embodiments, the immunogenic portion has 1, 2, 3, or 4 amino acid, substitutions, deletions, or mutations when compared to a sequence spanning 6, 7, 8, 9, 10, 11 or 12 contiguous amino acids of the amino acid sequence SEQ ID NO: 1 to 3.

The positions of the identified epitope regions correspond to the C-terminal beta ladder domain of NS1, spanning from positions 172 to 352. Therefore, in some embodiments, the immunogenic peptide, or immunogenic portion, has sequence homology to a portion (preferably a contiguous portion) spanning from positions 172 to 352 of NS1.

Consequently, in some embodiments, the immunogenic portion includes at least a portion of SEQ ID NO: 1 from position 150 to 352, or from position 172 to 352, or from positions 185 to 335, or from position 210 to 310, or from position 207 to 275. Consequently, in some embodiments, the immunogenic portion is at least 69 amino acids in length, or at least 101 amino acids in length, or at least 151 amino acids in length, or at least 183 amino acids in length, or at least 203 amino acids in length, or at least 250 amino acids in length, or at least 300 amino acids in length, or is the full length NS1 protein.

Further, in some embodiments, the immunogenic peptide or immunogenic portion has sequence homology to a portion of the NS1 protein (such as that set forth in SEQ ID NO: 1) located from position 172 to 278, or from position 204 to 278, or from position 204 to 352, or from position 204 to 218, or from positions 207 to 218, or from position 207 to 221, or from position 261 to 275, or from positions 264 to 275, or from position 264 to 278. Consequently, in some embodiments, the immunogenic portion is up to 12 amino acids in length, or up to 15 amino acids in length, or up to 74 amino acids in length, or up to 107 amino acids in length, or up to 149 amino acids in length, or up to 183 amino acids in length, or is the full length NS1 protein.

Signal Peptide and Secretion

The immunogenic peptide of the invention is secreted when expressed in a mammalian cell. As such, the heterologous signal peptide is a signal peptide which facilitates secretion of operatively linked proteins in a mammalian cell. In some embodiments, the signal peptide directs translocation of the operatively linked portion of NS1 to the endoplasmic reticulum, the cell membrane, the proteasome, the lysosome or directs binding of NS1 to specific cell type or cell subset.

In some embodiments, the signal sequence includes, a target sequence which targets the encoded product to a desired cell type or cellular subset and may facilitate secretion or localisation of the operatively linked portion of NS1. In some embodiments, the target sequence targets the operatively linked portion of NS1 to an immune cell. In some embodiments, the target sequence targets the operatively linked portion of NS1 to an antigen presenting cell. In some embodiment, the target sequence targets the encoded product to the proteasome of a host cell. In some embodiments, the target sequence targets the operatively linked portion of NS1 to the endosome or lysosome of a host cells.

The term "heterologous" is a relative term and is used when comparing the origin of at least two individual molecules (i.e., DNA, RNA, protein, etc.). As used herein, the term heterologous is used to describe at least two different molecules as being from different organisms or different species. As used throughout the specification the term heterologous, when used in reference to Zika virus, refers to any molecule (e.g. gene, nucleic acid, or polypeptide encoded by such a gene or nucleic acid) that is not derived from the Zika genome. As such, "heterologous" can refer to a gene, nucleic acid, or polypeptide encoded by such a gene or nucleic acid, derived from (or homologous with) a flavivirus other than Zika, another virus from a genus other than flavivirus, another viral family other than flaviviridae, a prokaryote, a eukaryote, or from an genome containing organelle therein.

The term "signal" in relation to a peptide sequence, or a sequence encoding a peptide or a nucleic acid, is used in the context of this specification in reference to a peptide (or encoding sequence), which at least directs secretion of the linked product. In some embodiments, the signal sequence initially directs the localisation or translocation of a portion NS1 within a host cell. In these embodiments, the signal sequences include both co-translational translocation sequences and post-translational translocation sequences. In some embodiments, the signal sequence directs the localisation of the operatively linked portion of NS1 to, or through, a membrane of the host cell. In some embodiments, the membrane is the Endoplasmic Reticulum (ER), which may result in localization of the linked portion of NS1 to the cell surface, or may result in secretion of the portion NS1. In a preferred embodiment, the signal sequence directs secretion of a linked portion of NS1 from the host cell.

A range of signalling peptides are known in the art which are suitable for use in the present invention. These include signals from eukaryotic cells, prokaryotic cells and viral genomes. A range of signalling peptides are available in the literature and are indexed in databases, such as the signal peptide database (http://www.signalpeptide.de/). Further, while signal sequences display little to no sequence conservation, they do display characteristic conserved physiochemical structure. As such, algorithms have been developed which identify signal peptides (for discussion on signal peptides and identification see Nicchitta, CV, "Signal Sequence Function in the Mammalian Endoplasmic Reticulum: A Biological Perspective", Curr. Top. Membr. 2002. 52, Ch. 7:483-499)

Exemplary signal sequences include, but are not limited to the tissue plasminogen activator (tPA) signal sequence, Japanese encephalitis virus signal sequence, erythropoietin (epo) signal sequence, VP22 HSV1 signal sequence, Parathyroid hormone-related protein (PTHrP) N-terminal ER signal sequence, Calreticulin (CRT), or Adenovirus E3 signal sequence, or flavivirus signal sequences, which includes structural proteins (e.g. capsid (C), envelope (E), or pre-membrane (prM) proteins). These signal sequences are considered as heterologous as long as they originate from flaviviruses other than Zika.

In some embodiments, the encoded peptide may include a target sequence which targets the encoded product to a desired cell type or cellular subset and may facilitate localisation of the operatively linked immunogenic peptide. In some embodiments, the target sequence targets the operatively linked immunogenic peptide to an immune cell. In some embodiments, the target sequence targets the operatively linked immunogenic peptide to an antigen presenting cell.

Immune cell targeting sequences include, but are not limited to, heat shock proteins (HSP70, gp96, calreticulin, HSP60), cytokines (FLT-3 ligand, GM-CSF), chemokines (MCP3, MIP1a, MIP-3a, RANTES, β-defensin, MC148, vMIP-I), single-chain fragment variable (scFv) antibody fragment, anti-CD40, anti-MHCII, anti-CD21, anti-DEC205, cytotoxic T lymphocyte-associated antigen 4 (CTLA-4), Fc fragment, CD154, fragment of the complement factor C3 (C3d), L-Selectin or fragment C of tetanus toxin (TetC), Immunoglobulin signal sequence (e.g. IgA, IgE or IgG).

In some embodiments, the target sequence targets the operatively linked portion of NS1 to the proteasome. Proteasome targeting of expression products can assist in facilitating MHC class I presentation of a linked expression product, such as a peptide or protein. Consequently, proteasome targeting can lead to activation of larger populations of CD8+ Cytotoxic T Lymphocytes, which may generate stronger anti-viral immunity.

Proteasome target sequences include, but are not limited to, co-translational ubiquitination of an expressed product, thereby fusing the expressed product to ubiquitin, ETA(dll) or γ-tubulin, transporters associated with antigen processing (TAP) proteins, or endoplasmic reticulum insertion signal sequences.

In some embodiments, the target sequence targets the operatively linked portion of NS1 to the endosome or lysosome of a host cells. Endosome and lysosome targeting sequences may assist in targeting linked antigens to the MHC-II pathways, thereby increasing CD4+T helper responses. Endosome or lysosome targeting sequences include, but are not limited to, lysosomal-associated membrane protein type 1 (LAMP-1), major histo-compatibility complex class II-associated invariant chain (Ii), melanosome transport sorting signals, or the transferrinreceptor (TfR)

In some embodiments, the heterologous signal peptide is a tissue plasminogen activator (tPA) signal peptide. The tPA signal peptide sequence is known in the art. However, in some embodiments the heterologous signal peptide has 80%, 85%, 90%, 95% or 100% sequence homology to the sequences set forth in SEQ ID NO: 5 or SEQ ID NO: 12. In some embodiments, the nucleic acid encoding the signal peptide has at least 80%, 85%, 90%, 95%, 98%, 99% or 100% sequence homology to the sequence set forth in SEQ ID NO: 6.

In some embodiments, the heterologous signal peptide is not an immunoglobulin (Ig) signalling peptide. In some embodiments, the signal peptide is not an IgE signalling peptide.

The term "portion", as used herein, when used with respect to protein, DNA, or other such macromolecules, refers to at least a part of the full length molecule. In some embodiments, when not used in conjunction with qualifier, the term portion relates to 10%, 20%, 30%, 40%, 50%, 60%, 70%, 80%, 90%, 95% or 99% of the full length macromolecule.

When used with reference to a functional requirement, a "portion" refers to a part of the macromolecule that still retains at least 10% of the functional capacity of the full length molecule, or at least 20%, 30%, 40%, 50%, 60%, 70%, 80%, 90%, 95% or 99% of the functional capacity of the full length molecule.

The term "immunogenic peptide", as used herein relates to the capacity of the peptide to induce an immune response within a subject administered the vaccine. What constitutes an immune response will be understood in the art. However, for clarity an immune response may include (but is not limited to) the induction of an innate immune response, or the induction of an adaptive immune response. In preferred embodiments, the immunogenic portion induces an adaptive immune response. In some embodiments, the immunogenic peptide induces an antigen specific immune response. An antigen specific immune response includes (but is not limited to) an; expansion of a lymphocyte population including T cells, affinity maturation of B cells, instigation of secretion of macromolecules such as antibodies (including isotype switching to IgA, IgG or IgE isotypes), instigation or enhancement of secretion of chemokines and/or cytokines (such as IL-2, IL-4, IL-5, IL-9, IL-12, IL-13, IL-17, IL-21, IL-22, IL-26, IFNg, TNFa, or TNFb), instigation or enhancement of CTL responses, instigation or enhancement of maturation of monocytes and/or dendritic cells, increase in surface expression of co-stimulation molecules, increase in the expression of Fc receptors, increase in the expression of major-histocompatibility (MHC) molecules, recruitment or migration of leukocytes, increase in expression of markers indicative of plasma cells or memory B cells (including CD38, CD21, CD24, CD19, B220, FcRH4 and CD25), upregulation of markers indicative of memory T cells (including CD45RO, CCR7, CD62L. CD27 or CD28), and upregulation of activation receptors (including CD69, Ki67 or CD40L).

In some embodiments, an immunogenic peptide induces a T cell response. In some embodiments the T cell response is a T-helper response and/or a CTL response. In some embodiment the immune response includes a B cell response. Preferably, an immunogenic peptide induces a T-helper response, a CTL response and a B cell response.

The term "encoding", as used herein, refers to the property of specific sequences of nucleotides, in a nucleic acid molecule such as a genomic DNA, cDNA, or mRNA, to serve as a template for the synthesis of polymers or macromolecules. The polymers or macromolecules in themselves may have a defined sequence, being a sequence of nucleotides (i.e., rRNA, tRNA and mRNA) or a defined sequence of amino acids (i.e. peptides such as proteins). Both the coding strand, the nucleotide sequence of which is identical to the mRNA sequence, and the complementary non-coding strand are to be considered as encoding the protein or other product of the specified sequence. Unless otherwise specified, a "nucleotide sequence encoding" an amino acid sequence, includes all nucleotide sequences that are degenerate versions of each other and that encode the same amino acid sequence. Degenerative codons are known in the art and are provided in the Table 2.

TABLE 2

| Amino Acid | Degenerate Codons Codon |
|---|---|
| START | AUG |
| Ala/A | GCU, GCC, GCA, GCG |
| Arg/R | CGU, CGC, CGA, CGG, AGA, AGG |
| Asn/N | AAU, AAC |
| Asp/D | GAU, GAC |

TABLE 2-continued

| Amino Acid | Degenerate Codons Codon |
|---|---|
| Cys/C | UGU, UGC |
| Gln/Q | CAA, CAG |
| Glu/E | GAA, GAG |
| Gly/G | GGU, GGC, GGA, GGG |
| His/H | CAU, CAC |
| Ile/I | AUU, AUC, AUA |
| STOP | UAA, UGA, UAG |
| Leu/L | UUA, UUG, CUU, CUC, CUA, CUG |
| Lys/K | AAA, AAG |
| Met/M | AUG |
| Phe/F | UUU, UUC |
| Pro/P | CCU, CCC, CCA, CCG |
| Ser/S | UCU, UCC, UCA, UCG, AGU, AGC |
| Thr/T | ACU, ACC, ACA, ACG |
| Trp/W | UGG |
| Tyr/Y | UAU, UAC |
| Val/V | GUU, GUC, GUA, GUG |

Sequences described herein may have one or more deletions, substitutions or insertions without departing from the present invention. Where a functional requirement is described with regard to the sequence, it is to be understood that the deletions, substitutions or insertions will not abrogate the function of the specified sequence. However, the function may be diminished without departing from the invention.

The term "substitution" refers to replacement of an amino acid at a particular position in a parent peptide or protein sequence with another amino acid. A substitution can be made to change an amino acid in the resulting protein in a non-conservative manner (i.e., by changing the amino acid belonging to a grouping of amino acids having a particular size or characteristic to an amino acid belonging to another grouping; e.g. substituting a hydrophilic amino acid with a hydrophobic amino acid) or in a conservative manner (i.e., by changing the amino acid belonging to a grouping of amino acids having a particular size or characteristic to an amino acid belonging to the same grouping; e.g. substituting a hydrophilic amino acid with a hydrophilic amino acid). Such a conservative change generally leads to a reduction in conformational and functional changes in the modified peptide/protein. The following are examples of various groupings of amino acids: 1) Amino acids with nonpolar R groups: Alanine, Valine, Leucine, Isoleucine, Proline, Phenylalanine, Tryptophan, Methionine; 2) Amino acids with uncharged polar R groups: Glycine, Serine, Threonine, Cysteine, Tyrosine, Asparagine, Glutamine; 3) Amino acids with charged polar R groups (negatively charged at pH 6.0): Aspartic acid, Glutamic acid; 4) Basic amino acids (positively charged at pH 6.0): Lysine, Arginine, Histidine (at pH 6.0). Another grouping may be those amino acids with phenyl groups: Phenylalanine, Tryptophan, and Tyrosine.

A person skilled in the art will recognise that any amino acid can be substituted with a chemically (functionally) similar amino acid and retain function of the polypeptide. Such conservative amino acid substitutions are well known in the art. The following groups in Table 3 each contain amino acids that are conservative substitutions for one another.

TABLE 3

Exemplary amino acid conservative substitutions

| Original Residue | Exemplary Substitutions |
| --- | --- |
| Ala (A) | Val (V), Leu (L), Ile (I), Gly (G) |
| Arg (R) | Lys (K) |
| Asn (N) | Gln (Q), His (H) |
| Asp (D) | Glu (E) |
| Cys (C) | Ser (S) |
| Gln (Q) | Asn (N), His (H) |
| Glu (E) | Asp (D) |
| Gly (G) | Pro (P), Ala (A) |
| His (H) | Asn (N), Gln (Q) |
| Ile (I) | Leu (L), Val (V), Ala (A) |
| Leu (L) | Ile (I), Val (V), Met (M), Ala (A), Phe (F) |
| Lys (K) | Arg (R) |
| Met (M) | Leu (L), Phe (F) |
| Phe (F) | Leu (L), Val (V), Alal (A) |
| Pro (P) | Gly (G) |
| Ser (S) | Thr (T) |
| Thr (T) | Ser (S) |
| Trp (W) | Tyr (Y) |
| Tyr (Y) | Trp (W), Phe (F) |
| Val (V) | Ile (I), Leu (L), Met (M), Phe (F), Ala (A) |

Furthermore, if desired, unnatural amino acids or chemical amino acid analogues can be introduced as a substitution or addition into a polypeptide encompassed herein. Such amino acids include, but are not limited to, the D-isomers of the common amino acids, 2,4-diaminobutyric acid, α-amino isobutyric acid, 4-aminobutyric acid, 2-aminobutyric acid, 6-amino hexanoic acid, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogues in general.

The term "insertion" refers to addition of amino acids within the interior of the sequence. "Addition" refers to addition of amino acids to the terminal ends of the sequence. "Deletion" refers to removal of amino acids from the sequence.

The term "nucleic acid molecule", as used herein, refers to a polymeric form of nucleotides of any length, either ribonucleotides or deoxyribonucleotides. These terms include a single-, double- or triple-stranded DNA, genomic DNA, cDNA, genomic RNA, mRNA, DNA-RNA hybrid, or a polymer comprising purine and pyrimidine bases, or other natural, chemically, biochemically modified, non-natural or derivatized nucleotide bases. The backbone of the polynucleotide can comprise sugars and phosphate groups, or modified or substituted sugar or phosphate groups. Further, the backbone of the polynucleotide can comprise a polymer of synthetic subunits such as phosphoramidates. As can be deduced from the specification, references to DNA molecules that encode a specific product (whether a subsequent nucleic acid or a peptide or polypeptide) are not (unless specified to the contrary) to be considered as limited to a specific structure, rather they should be considered in view of their encoded product.

The term "operatively linked" as used herein in reference to the signal peptide and the immunogenic peptide (or immunogenic portion of NS1) refers to a link between the signal peptide and the immunogenic peptide whereby the functionality of the signal peptide influences the location of the immunogenic peptide. In the specific context of the invention, the operatively linked signal peptide facilitates secretion of the immunogenic peptide from a mammalian cell. The term "operatively linked" does not require that the signal peptide and immunogenic peptide remained in linkage indefinitely. It is envisaged that the signal peptide may be ligated from the immunogenic peptide after it has facilitated secretion of the immunogenic peptide, or after translocation of the immunogenic peptide to a cellular location that will ultimately result in its secretion.

DNA Vectors

In some embodiments the vaccine includes a DNA vector, the DNA vector including a nucleic acid encoding an immunogenic portion of a sequence homologous to NS1 as described herein operatively linked to a nucleic acid encoding the heterologous signal peptide as described herein.

As will be understood DNA vectors include promotor sequences for driving expressing of the encoded peptides. A non-exhaustive list of possible promoters are provided in Table 4.

TABLE 4

| Promoters | | | |
|---|---|---|---|
| Promoter | Primarily used for | Description | Expression |
| CMV | General expression | Strong mammalian expression promoter from the human cytomegalovirus | Constitutive |
| EF1a | General expression | Strong mammalian expression from human elongation factor 1 alpha | Constitutive |
| SV40 | General expression | Mammalian expression promoter from the simian vacuolating virus 40 | Constitutive |
| PGK1 (human or mouse) | General expression | Mammalian promoter from phosphoglycerate kinase gene. | Constitutive |
| Ube | General expression | Mammalian promoter from the human ubiquitin C gene | Constitutive |
| human beta actin | General expression | Mammalian promoter from beta actin gene | Constitutive |
| CAG | General expression | Strong hybrid mammalian promoter | Constitutive |
| TRE | General expression | Tetracycline response element promoter | Inducible with Tetracyline or its derivatives. |
| UAS | General expression | Drosophila promoter conaining Gal4 binding sites | Specific |

TABLE 4-continued Promoters

| Promoter | Primarily used for | Description | Expression |
|---|---|---|---|
| Ac5 | General expression | Strong insect promoter from Drosophila Actin 5c gene | Constitutive |
| Polyhedrin | General expression | Strong insect promoter from baculovirus | Constitutive |
| CaMKIIa | Gene expression for optogenetics | Ca2+/calmodulin-dependent protein kinase II promoter | Specific |
| GAL1, 10 | General expression | Yeast adjacent, divergently transcribed promoters | Inducible with galactose; repressible with glucose |
| TEF1 | General expression | Yeast transcription elongation factor promoter | Constitutive |
| GDS | General expression | Strong yeast expression promoter from glyceraldehyde 3-phosphage dehydrogenase | Constitutive |
| ADH1 | General expression | Yeast promoter for alcohol dehydrogenase I | Repressed by ethanol |
| H1 | small RNA expression | From the human polymerase III RNA promoter | Constitutive |
| U6 | small RNA expression | From the human U6 small nuclear promoter | Constitutive |

In some embodiments, the DNA vector is the gWIZ vector, the pVax 1 vector, the pcDNA3.1 vector (see Gomez L. and Onate A. Plasmid-Based DNA Vaccines, DOI: 10.5772/intechopen.76754), the NTC8385 vector and the NTC9385R vector (see Williams J. Vaccines, 2013, 1(3): pp. 225-249).

In some embodiments, the DNA vector includes a promotor which is constitutive in a mammalian cell. In some embodiments, the promoter is selected from the group of CMV, SV41, UBC, EF1A, PGK or CAGG. In some embodiments, the promoter is a derived from cytomegalovirus (CMV).

DNA vectors suitable for use with the present invention are known in the art, and include vectors approved for therapeutic use by regulatory bodies including the US Food and Drug Administration (FDA), the European Medicines Agency (EMA), the Australian Therapeutic Goods Administration (TGA) and the Chinese Food and Drug Administration (CDFA).

Any suitable DNA vector can be used in the present invention, which may include naked DNA. It is therefore not intended that the invention described herein in limited to a specific vector, unless expressly stated.

However, when the term "DNA vector" is used throughout this specification, it is intended to refer to a polynucleotide/nucleic acid, construct designed for transduction/transfection of one or more cell types. These may include, for example; "cloning vectors" which can be stably maintained in a target cell and can facilitate propagation, replication and subsequent isolation of inserted nucleotide molecules; "expression vectors" designed for expression of selected nucleotide sequence in a host cell; a "viral vector" which are designed to facilitate the production of a recombinant DNA containing virus or virus-like particle in a host cell, or "shuttle vectors", which can propagate in host cells from more than one species.

It is envisaged that the vectors of the present invention, wherein they are so described and claimed, can comprises a nucleic acid molecule encoding a Zika virus NS1 protein as well as a nucleic acid molecule encoding another protein (additional to the signal peptide) that may direct the localisation of the NS1 protein and improve efficacy of the vector. Proteins that improve the efficacy of the vector may include, but are not limited to, cytokines; chemokines; co-stimulatory proteins; angiostatin; endostatin; and heat shock proteins.

Typically, a vector will include cloning, or restriction, sites for insertion or DNA, a promoter (as discussed above) to induce the production of the inserted DNA, and DNA portion that encodes for proteins which permit selection or identification vector carrying host cell(s).

Methods are known in the art for producing, modifying and optimising suitable vectors for use in the present invention (see, for example, Iurescia S. et al. (2014) A Blueprint for DNA Vaccine Design. In: Rinaldi M. et al. (eds); DNA Vaccines. Methods in Molecular Biology (Methods and Protocols), vol 1143. Humana Press, New York, N.Y.).

In some embodiment, the vector comprises a pVax vector.

Viral Vectors

In some embodiments the vaccine includes a viral vector, the viral vector including an immunogenic peptide as described herein operatively linked to a heterologous signal peptide as described herein, or the viral vector includes a nucleic acid encoding an immunogenic peptide as described herein operatively linked to a nucleic acid encoding the heterologous signal peptide as described herein.

Viral vectors suitable for use with the present invention are known in the art, and include vectors approved for therapeutic use by regulatory bodies including the US Food and Drug Administration (FDA), the European Medicines Agency (EMA), the Australian Therapeutic Goods Administration (TGA) and the Chinese Food and Drug Administration (CDFA).

Any suitable viral vector can be used in the present invention. It is therefore not intended that the invention described herein in limited to a specific viral vector, unless expressly stated.

Examples of viral vectors suitable for use with the present invention include (but are not limited to); measles virus, adenovirus, Varicella-zoster virus, Human parainfluenza virus 3, Coxsackievirus group B, Retrovirus, Lentivirus, Vaccinia virus Adenovirus, Adeno-associated virus, Cytomegalovirus, Sendai virus and Poxvirus—modified vaccinia Ankara. Methods are known in the art for producing viral vectors comprising a peptide of nucleic acid in accordance with the invention. For example see Lauer K et al. *Multivalent and Multipathogen Viral Vector Vaccines*; Clinical and Vaccine immunology. DOI: 10.1128/CVI.00298-16, and Ura T. et al. Developments in Viral Vector-Based Vaccines; Vaccines, 2014, 2(3): pp. 624-641.

Peptides and Immunogenic Portion of NS1

As describe further in the Examples, the present inventors have identified immunogenic regions of the NS1 protein which elicit both a cytotoxic T-lymphocyte (CTL) and T-helper response. Therefore, the present invention provides an immunogenic peptide for eliciting an immune response, including an immunogenic portion of a sequence homologous to the NS1 protein of Zika virus. The immunogenic portion can be any suitable portion that elicits an immune response as defined herein.

Specifically, the inventions identified two peptides of 15 amino acids long that initiated a CTL response in animals vaccinated with a vector encoding NS1 operatively linked to a signal sequence. These two peptides had a conserved sequence of 12 amino acids (SEQ ID NO: 3). Further, the inventors identified two peptides of 15 amino acids that initiated a T helper response in animals vaccinated with NS1 and a signal sequence. The two peptides also had a conserved sequence of 12 amino acids (SEQ ID NO: 2).

As such, in some embodiments, the immunogenic portion of a sequence homologous to the NS1 protein of Zika virus is at least 12 amino acids long. In some embodiments, the immunogenic portion of a sequence homologous to the NS1 protein of Zika virus is up to 12 amino acids long The peptides of SEQ ID NO: 2 and 3 were identified at positions 207 to 218 and 264 to 275 of SEQ ID NO: 1 (see bound areas in FIG. 2). Notably, and as illustrated in FIG. 2, positions 264 and 265 are polymorphic between strains. Therefore, in some embodiments the immunogenic portion of a sequence homologous to the NS1 protein of Zika virus spans from position 266 to 275 and is at least 70%, 75%, 80%, 85%, 90%, 95% or 100% homologous to the respective positions of SEQ ID NO: 1.

The region spanning positions 172 to 352 of the Zika NS1 protein, when in an in silico-modelled hexadimer, locates to the outer layer of the oligomer (Song et al. Nat. Struct. Mol. Biol., 23:456-458). As such, this region likely presents antigenic regions for interaction with the host immune system. Therefore, in some embodiments, the immunogenic portion of a sequence homologous to the NS1 protein is located between positions 172 to 352 of SEQ ID NO: 1.

Cytotoxic T-lymphocyte and T helper responses are initiated by peptides being presented within a binding groove of the major histocompatibility complex (MHC). Class I MHC (MHC-I) molecules present antigens to CTL cell expressing the CD8 co-receptor, while class II MHC (MHC-II) presents antigen to T helper cell expressing the CD4 co-receptor. The binding groove of MHC-I has closed ends. Therefore, the size of molecules presented by MHC-I to CTLs is typically 8 to 10 amino acids. As such, it is likely that the 12 amino acid long peptides are being internally processed to a shorter 8 to 10 amino acid length, with a portion of these including an immunogenic epitope.

Despite, MHC only binding short peptides (typically 8 to 15 residues, as described above), longer proteins are processed within antigen presenting cells and digested to shorter peptide sequences which can be loaded onto MHC molecules. Therefore, the immunogenic peptides of the present invention can be considerably longer than 8 amino acid residues and can be up to the full length of the non-structural proteins.

Therefore, in some embodiments the immunogenic peptide, or immunogenic portion, is at least 8 amino acids in length, at least 9 amino acids in length, at least 10 amino acids in length, at least 11 amino acids in length, at least 12 amino acids in length, at least 13 amino acids in length, at least 14 amino acids in length, at least 15 amino acids in length, at least 16 amino acids in length, at least 17 amino acids in length, at least 18 amino acids in length, at least 19 amino acids in length, at least 20 amino acids in length, at least 22 amino acids in length, at least 24 amino acids in length, at least 26 amino acids in length, at least 28 amino acids in length, at least 30 amino acids in length, at least 35 amino acids in length, at least 40 amino acids in length, at least 45 amino acids in length, at least 50 amino acids in length, at least 55 amino acids in length, at least 60 amino acids in length, at least 65 amino acids in length, at least 69 amino acids in length, at least 70 amino acids in length, at least 75 amino acids in length, at least 80 amino acids in length, at least 85 amino acids in length, at least 90 amino acids in length, at least 95 amino acids in length, at least 100 amino acids in length, at least 110 amino acids in length, at least 120 amino acids in length, at least 130 amino acids in length, at least 140 amino acids in length, at least 150 amino acids in length, at least 160 amino acids in length, at least 170 amino acids in length, at least 180 amino acids in length, at least 183 amino acids in length, at least 190 amino acids in length, at least 200 amino acids in length, at least 210 amino acids in length, at least 250 amino acids in length, at least 260 amino acids in length, at least 300 amino acids in length, at least 310 amino acids in length, at least 350 amino acids in length, or is the full length NS1 protein. In some of the above embodiments the immunogenic peptide has sequence homology to the amino acid sequence set forth in SEQ ID NO: 1 or SEQ ID NO: 2 or SEQ ID NO: 3

In some embodiments, the immunogenic peptide, or immunogenic portion, is up to 351 amino acids in length, or up to 300 amino acids in length, or up to 250 amino acids in length, or up to 200 amino acids in length, or up to 181 amino acids in length, or up to 150 amino acids in length, or up to 100 amino acids in length, or up to 80 amino acids in length, or up to 60 amino acids in length, or up to 50 amino acids in length, or up to 40 amino acids in length, or up to 30 amino acids in length, or up to 20 amino acids in length, or up to 18 amino acids in length, or up to 16 amino acids in length, or up to 14 amino acids in length, or up to 12 amino acids in length, or up to 10 amino acids in length, or up to 8 amino acids in length.

In some embodiments, the immunogenic peptide or immunogenic portion has at least 70% sequence homology to a portion of at least 7, 8, 9, 10, 11 or 12 contiguous amino acids of the NS1 protein of Zika virus, preferably the sequence set forth in SEQ ID NO: 1. In some embodiments, the immunogenic peptide or immunogenic portion has at least 70% sequence homology to a portion of at least 7, 8, 9, 10, 11 or 12 contiguous amino acids of SEQ ID NO: 2 and/or SEQ ID NO: 3

In some embodiments, the immunogenic portion of a sequence homologous to the NS1 protein of Zika virus is at least 6 amino acids longs. In some embodiments, the immunogenic portion of the NS1 protein includes at least 6 contiguous amino acids of the amino acid sequence set forth in SEQ ID NO: 2 and/or the sequence set forth in SEQ ID NO: 3. In some embodiments, the immunogenic portion of a sequence homologous to the NS1 protein of Zika virus is at least 7 amino acids longs. In some embodiments, the immunogenic portion of the NS1 protein includes at least 7 contiguous amino acids of the amino acid sequence set forth in SEQ ID NO: 2 and/or the sequence set forth in SEQ ID NO: 3. In some embodiments, the immunogenic portion of a sequence homologous to the NS1 protein of Zika virus is at least 8 amino acids longs. In some embodiments, the immunogenic portion of the NS1 protein includes at least 8 contiguous amino acids of the amino acid sequence set forth in SEQ ID NO: 2 and/or the sequence set forth in SEQ ID NO: 3. In some embodiments, the immunogenic portion of a sequence homologous to the NS1 protein of Zika virus is at least 9 amino acids longs. In some embodiments, the immunogenic portion of the NS1 protein includes at least 9 contiguous amino acids of the amino acid sequence set forth in SEQ ID NO: 2 and/or the sequence set forth in SEQ ID NO: 3. In some embodiments, the immunogenic portion of a sequence homologous to the NS1 protein of Zika virus is at least 10 amino acids longs. In some embodiments, the immunogenic portion of the NS1 protein includes at least 10 contiguous amino acids of the amino acid sequence set forth in SEQ ID NO: 2 and/or the sequence set forth in SEQ ID NO: 3. In some embodiments, the immunogenic portion of a sequence homologous to the NS1 protein of Zika virus is at least 11 amino acids longs. In some embodiments, the immunogenic portion of the NS1 protein includes at least 11 contiguous amino acids of the amino acid sequence set forth in SEQ ID NO:2 and/or the sequence set forth in SEQ ID NO: 3.

In some embodiments, the immunogenic portion of a sequence homologous to the NS1 protein of Zika virus includes the amino acid sequence set forth in SEQ ID NO:2 and/or the sequence set forth in SEQ ID NO: 3.

In some embodiments of the immunogenic peptide, the immunogenic portion of a sequence homologous to the NS1 protein of Zika virus includes a portion of the sequence from position 150 to 360 of SEQ ID NO: 1, or from position 210 to 310 of SEQ ID NO: 1, or from position 207 to 285 of SEQ ID NO: 1. In some embodiments this portion is 6 contiguous amino acids, or 7 contiguous amino acids, or 8 contiguous amino acids, or 9 contiguous amino acids, or 10 contiguous amino acids, or 11 contiguous amino acids, or 12 contiguous amino acids.

Methods for screening immunogenic portions of proteins are known in the art, and include automated predictive algorithms. Further, experimental methods for identifying immunogenic regions are present herein in the Examples.

DNA Vaccines

Many known forms of vaccines against viruses are used for inferring protection to pathogenic organisms. The most common of which include live-attenuated viruses, inactivated (killed) viruses, subunit or recombinant vaccines that use portions of viral capsule proteins or virus like particles. However, one of the most promising vaccine types are DNA vaccines.

DNA vaccines, in their simplest form, consist of a DNA plasmid or vector containing an immunogenic gene (or portion of a gene) of a pathogen, and elements needed to transcribe this gene in the target subject. This DNA is administered to a subject during immunization. The encoded immunogenic gene is transcribed, and the antigen is translated to elicit an immune response.

Unlike protein based vaccines, DNA vaccines have the advantage of synthesizing the specific antigen in the host's target organism (as opposed to a model system in vitro). This ensures that the proteins, once translated are processed (e.g. glycosylated and folded) correctly to elicit the appropriate immune response.

Furthermore, DNA vaccines have the advantage of being simple and cheap to produce and being stable for transportation and storage, when compared to protein based vaccines. DNA can be readily lyophilised and rehydrated prior to administration without significant loss in functionality.

Accordingly, the present invention provides a DNA vaccine including a nucleic acid molecule in accordance with the invention as described herein.

Further, the present invention provides a pharmaceutical composition including a nucleic acid molecule as described herein and a pharmaceutically acceptable excipient or solvent. In some embodiments, the pharmaceutical composition further comprises an adjuvant for enhancing the immunogenicity of the vaccine.

In some embodiments of the vaccine for administering to a mammal, the sequence of the nucleic acid molecule, which encodes the immunogenic peptide and/or the heterologous signal peptide, is codon optimised. In preferred embodiments or the nucleic acid molecule encoding an immunogenic peptide having at least 70% sequence homology to a portion of the non-structural protein 1 of Zika virus includes a codon optimised nucleic acid, which encodes the immunogenic portion of the NS1 protein. In some embodiments, the codon optimised nucleic acid, which encodes the immunogenic portion of the NS1 protein has the sequence set forth in SEQ ID: NO: 4.

In preferred embodiments, the immunogenic portion is secreted when expressed in a mammalian cell. As such, the heterologous signal peptide is a signal peptide which facilitates secretion of operatively linked peptide from a mammalian cell. However, in some embodiments, the signal peptide directs translocation of the operatively linked immunogenic portion NS1 to the endoplasmic reticulum, the cell membrane, the proteasome, the lysosome or directs the immunogenic portion of NS1 to specific cell type or cell subset.

The present invention further provides a peptide composition including an immunogenic peptide having at least 6, 7, 8, 9, 10 or 11 contiguous amino acid portion of the sequence set forth in SEQ ID NO:2 and/or an immunogenic peptide having at least a 6, 7, 8, 9, 10 or 11 contiguous amino acid portion of the sequence set forth in SEQ ID NO: 3. In some embodiments, the composition includes the immunogenic peptide having the sequence set forth in SEQ ID NO:2 and/or the sequence set forth in SEQ ID NO: 3

A, "vaccine" composition refers to a composition comprising at least a vector as described herein, which is useful to establish immunity to the Zika virus in the subject. It is contemplated that the vaccine comprises a pharmaceutically acceptable carrier, solvent, excipient and/or an adjuvant.

A vaccine composition envisages a prophylactic or therapeutic treatment. A "prophylactic" treatment is a treatment administered to a subject, who does not exhibit signs of an infection, for the purpose of reducing the likelihood of a Zika infection, decreasing the risk of developing pathology from a Zika virus infection, decreasing the severity of a Zika virus infection, or decreasing the risk of transmitting a Zika virus infection to another subject.

A "therapeutic" treatment is a treatment administered to a subject who exhibits signs or symptoms of pathology, for the purpose of reducing the severity of infection, shortening the duration of infection, reducing or eliminating signs or symptoms of an infection, reducing viral shedding of the infection, or reducing the likelihood of transmitting the infection.

A "DNA Vaccine" as used throughout the specification refers to a synthetic DNA structure that can be administered to a subject and transfected into one or more host cells whereby it is transcribed. A DNA vaccine can comprise any suitable DNA molecule including linear nucleic acid, such as a purified DNA molecule, a plasmid incorporating a DNA molecule, or a DNA molecule incorporated into another suitable vector for introduction (transfection, transduction, transformation etc.) of the DNA molecule into the cell of a treated subject. Accordingly, in some embodiments, the DNA vaccine can be naked DNA, a DNA vector or a viral vector vaccine (live, attenuated, inactivated or killed).

As used herein, "pharmaceutical composition" refers to a composition suitable for administration to a subject animal, including humans. In the present context, a pharmaceutical composition comprises a pharmacologically effective amount of a DNA vector including a nucleic acid molecule of the present invention and also a pharmaceutically acceptable carrier, solvent or excipient. Accordingly, a pharmaceutical compositions of the present invention encompass any composition made by admixing a nucleic acid molecule in accordance with the present invention and a pharmaceutically acceptable carrier.

As used herein, a "pharmaceutically acceptable carrier" include any and all clinically useful solvents, dispersion media, coatings, antibacterial and antifungal agents, isotonic and absorption delaying agents, buffers, and excipients, such as a phosphate buffered saline solution (PBS), aqueous solutions of dextrose or mannitol, and emulsions, such as an oil/water or water/oil emulsion, and various types of wetting agents and/or adjuvants. Suitable pharmaceutical carriers and formulations are described in Remington's Pharmaceutical Sciences, 21st Ed. (Mack Publishing Co., Easton, 2006). Pharmaceutical carriers useful for the composition depend upon the intended mode of administration of the active agent. Typical modes of administration include parenteral administration, including subcutaneous, intramuscular, intravenous or intraperitoneal injection; transdermal; or transmucosal administration.

A vaccine may comprise immune enhancing agents such as adjuvants. Adjuvants for conventional vaccines include, but are not limited to, saponin, non-ionic detergents, vegetable oil, aluminum hydroxide, surface active substances (including lysolecithin, pluronic polyols, polyanions) peptides, oil or hydrocarbon emulsions, keyhole limpet hemocyanins.

Specific adjuvants for DNA vaccines include plasmids, or other nucleic acid molecules, encoding immunomodulatory proteins, such as cytokines (including IL-2, IL-4, IL-5, IL-6, IL-8, IL-12, IL-18, IL-21, IFNg TGFβ, GM-CSF) chemokines (including MIP-1α, MIP-3α, MIP-3β, and RANTES), co-stimulatory and adhesion molecules (including B7-1, B7-2, LFA-3 and ICAM-1), molecules that block co-inhibitory molecules (including blocking PD-1).

Methods are known in the art for optimizing DNA based vaccines. For example see: William J. A. et al. Biotechnol Adv. 2009; 27(4): 353-370; William J. A, Curr Gene Ther. 2014; 14(3):170-89; and Iurescia S1, Fioretti D & Rinaldi, M Methods Mol Biol. 2014; 1143:3-10.

Methods of Use

The invention provides methods for using the nucleic acid molecule, immunogenic peptides, vaccines, pharmaceutical compositions and peptide compositions, as described herein.

Vaccination

The disclosure herein provides methods of immunizing, or vaccinating, an individual for the prevention of Zika virus infection. Further provided herein are methods of treating, or reducing transmission, of a Zika virus infection. In some embodiments, these methods are achieved by eliciting an immune response in a subject. As such, in some embodiments, the invention provides a method of eliciting an immune response in a subject, the method including the step of; administering to the subject an immunogenic agent, wherein the immunogenic agent is a nucleic acid molecule, a vaccine, a pharmaceutical composition, an immunogenic peptide or a composition as described herein.

In some embodiments, the immune response is a T cell response. In some embodiments, the T cell response is the generation of ZIKA NS1-specific CD8+ T cells and/or CD4+ T cells. In some embodiments, the T cell immune response results in ZIKA NS1 memory T cells.

In some embodiments, the T cells response is elicited in response to an immunogenic portion spanning a portion, or all of, positions 172 to 352 of NS1.

In some embodiments, the immune response is a B cell response. In some embodiments, the B cell response results in the generation of ZIKA anti-NS1 antibodies. In some embodiments, the B cell immune response results in ZIKA NS1 memory B cells.

Regimens for immunizing a subject are known in the art, and may vary depending on the composition of vaccine (e.g. the presence of adjuvants), the route of administration, and the immuno-competence of the individual. In some embodiments, the method of eliciting an immune response includes a dosage regimen, wherein the immunogenic agent is administered in a single dose, in two doses, in three doses, in four doses, or in five doses. In some embodiments, the method of eliciting an immune response includes a dosage regimen, wherein the immunogenic agent is administered in at least a single dose, in at least two doses, in at least three doses, in at least four doses, or in at least five doses.

In some embodiments, the method of eliciting an immune response in a subject includes administering an immunogenic agent via a parenteral route. Exemplary parenteral routes include an intravenous route, a subcutaneous route, an intradermal route, or an intramuscular route.

In some embodiments, the invention provides the use of a vaccine, a pharmaceutical composition, an immunogenic peptide, or a peptide composition as described herein, for eliciting an immune response in a subject.

A method of eliciting an immune response is significant if there is a detectable change in the physiology of a subject that enhances at least one primary or secondary humoral or cellular immune response against at least one strain of an infectious Zika virus. The nucleic acid molecule, vaccine, pharmaceutical composition, peptide or peptide composition as described herein is administered by a method of the invention to protect against Zika viral infection. The "protection" need not be absolute, i.e., the Zika infection need not be totally prevented or eradicated, if there is a statistically significant improvement compared with a control population or subject. Protection may be limited to reducing the severity or duration of the symptoms or the infection, or preventing latency in the infected subject.

Methods are known in the art to evaluate the induction of an immune response. Exemplary methods include (but are not limited to) the induction of an innate immune response, or the induction of an adaptive immune response. In preferred embodiments, the immunogenic portion induces an adaptive immune response. In some embodiments, the immunogenic compound induces an antigen specific immune response. An antigen specific immune response includes (but is not limited to) the expansion of lymphocytes population including T cells, affinity maturation of B cells, instigation of secretion of macromolecules such as antibodies (including isotype switching to IgA, IgG or IgE isotypes), instigation or enhancement of secretion of chemokines and/or cytokines (such as IL-2, IL-4, IL-5, IL-9, IL-12, IL-13, IL-17, IL-21, IL-22, IL-26, IFNg, TNFa, or TNFb), instigation or enhancement of CTL responses, instigation or enhancement of maturation of monocytes and/or dendritic cells, increase in surface expression of co-stimulation molecules, increase in the expression of Fc receptors, increase in the expression of major-histocompatibility (MHC) molecules, recruitment or migration of leukocytes, increase in expression of markers indicative of plasma cells or memory B cells (including CD38, CD21, CD24, CD19, B220, FcRH4 and CD25), upregulation of markers indicative of memory T cells (including CD45RO, CCR7, CD62L. CD27 or CD28), and upregulation of activation receptors (including CD69, Ki67 or CD40L).

In some embodiments, treatment of a Zika infection may include: reducing the likelihood of infection with Zika virus; reducing the severity of Zika virus infection; reducing the duration of Zika virus infection; decreasing viral titres during Zika virus infection; decreasing viral sheading during Zika virus infection; or reducing one or more symptoms or side effects of Zika virus infection, including, but not limited to, fever, rash, joint pain, conjunctivitis, muscle pain, headache.

In some embodiments, the subject is a human. In some embodiments, the subject is a human who is immunologically naïve for Zika virus. In some embodiments, the subject is a female. In some embodiments, the subject is pregnant. In some embodiments, the subject has an active infection or indications of a recent infection. In some embodiments, the subject has a subclinical infection. In some embodiments, the subject is a male. In some embodiments, the subject has viral DNA in semen samples.

The precise dose of the nucleic acid molecule, vaccine, pharmaceutical composition, peptide or peptide composition to be employed in methods of the invention will depend on multiple factors including the route of administration, and the nature of the patient, and should be decided according to the judgment of the practitioner and each patient's circumstances according to standard clinical techniques. In some embodiments a pharmaceutically effective amount will be administered. An "effective amount" is an amount sufficient to achieve a desired biological effect such as to induce enough humoral or cellular immunity.

Antibody Production

Methods are known in the art to produce monoclonal and polyclonal antibodies for experimental and therapeutic uses, for example see Leenaars, M. and Hendriksen, C. F. M., "Critical Steps in the Production of Polyclonal and Monoclonal Antibodies: Evaluation and Recommendations", 2005, ILAR Journal, 46(3):269-279, In the context of the present invention methods relate to the administration of a nucleic acid sequence in accordance with the present invention, or an immunogenic peptide as described herein, or identified in accordance with methods provided herein, to a subject to induce specific B cells and plasma cells within the subject. These cells are isolated, typically from the spleen or lymph nodes of an immunized subject, and are fused to form a hybridoma.

Consequently the present invention provides a method of producing an anti-Zika NS1 protein antibody. The method comprising; administering to a subject a nucleic acid molecule, a vaccine, a pharmaceutical composition, or an immunogenic peptide as described herein; isolating serum from the subject; and purifying an antibody from the serum.

Further, the invention provides a method of producing an antibody comprising: administering to a subject a nucleic acid molecule, a vaccine, a pharmaceutical composition, or an immunogenic peptide as described herein; isolating B cells from the subject; fusing the isolated B cells to immortalised cells to prepare a hybridoma; culturing the hybridoma; and purifying an antibody from the culture supernatant.

Detecting Viral Infection and Immune Responses

Current diagnostic tests for infection with Zika virus use specific Zika virus proteins (i.e. antibodies directed against Zika virus structural proteins) or inactivated virus to detect anti-Zika virus antibodies in an individual's blood. These techniques primarily detect the presence of the infection agent, but do not detect the activity of the immune response.

The present invention provides an alternative method of detecting a Zika virus infection, and detecting the presence of an anti-Zika T cell response. In some embodiments, the method includes detecting Zika virus-specific T-cells by administering to a subject, or an in vitro sample, an immunogenic peptide as describe herein, and detecting the binding of T-cells to the immunogenic peptide.

Methods are known for detecting binding of peptides to MHC molecules. However, in some embodiments, the method for detecting Zika virus-specific T-cells includes administering the immunogenic peptides together with MHC molecules. In some embodiments, the MHC molecules are oligomerized. In some embodiments, the MHC molecules are biotinylated. In some embodiments, the MHC molecules are in the form of a tetramer. In some embodiments, the MHC molecules are associated with a detecting agent such as a fluorophore. Preferably, the Zika virus-specific T-cells are Zika NS1-specific T cells.

The present invention further provides methods of detecting Zika virus infection, the methods including administering to a subject, or an in vitro sample, an anti-NS1 antibody generated in accordance with methods of the present invention. In some embodiments of this method, the antibody is immobilised on a substrate, biotinylated, or labelled.

Method of Testing Vaccine Efficacy

In some embodiments, the invention provides a method of detecting the induction of an anti-NS1 immune response in a subject the method including; administering to a subject a vaccine for Zika virus, the vaccine comprising a NS1 protein or nucleotide encoding the same; obtaining or receiving a sample from the subject; contacting the same with a peptide as described herein, wherein binding of the peptide to a T cell receptor (TCR) indicates the presence of an immune response.

Methods are known for assessing the binding of a peptide to a TCR, and may include MHC (class 1 or class 2) oligomers, such as tetramers, pentamers or dextramers, or an immune bioassay comprising pulsing sampled lymphocytes with immunogenic peptides.

In some embodiments, the invention provides a method of detecting the induction of an anti-NS1 immune response in a subject the method including; administering to a subject a vaccine for Zika virus, the vaccine comprising a NS1 protein or nucleotide encoding the same; obtaining or receiving a sample from the subject; contacting the same with an antibody produced according to a method described herein, wherein binding of the antibody indicates the induction of an immune response Methods are known for detecting antibody binding including directly tagging antibodies and the use of tagged secondary antibodies for indirect detection. Suitable tags include fluorescent labels (e.g. fluorescent-activated cell sorting or fluorescent microscopy) or chromogenic enzymes (e.g. ELISA, ELIspot).

EXAMPLES

The invention is further described and illustrated in the following examples. The examples are only for the purpose of describing particular embodiments of the invention, and are not intended to be limiting with respect to the above description and the scope of the invention as claimed in this application or future applications claiming priority from this application.

Example 1—Immunogenicity of NS1 DNA Vectors

DNA vaccines encoding membrane and envelope proteins of Zika virus have previously been trialled with varying results. To assess if non-structural proteins could be utilised in inducing an immune response in a murine model, three DNA vectors containing nucleic acid sequences encoding NS1 were prepared as set out below. The immunogenicity of the NS1 vectors were compared to a blank control plasmid and total IgG titres were assessed in a murine model.

Preparation of Plasmid Vaccine

An exemplified protocol for preparing nucleic acid vectors for expressing a NS1 protein from Zika virus is detailed as follows.

Three DNA plasmid containing nucleic acids encoding NS1 were prepared as set out below. Further, a plasmid, containing no inserted DNA was use as a control.

DNA encoding the NS1 protein of Zika virus (SEQ ID NO: 4), tissue plasminogen activator (SEQ ID NO: 6) and the oligomerisation domain of the C4 binding protein (IMX313P) was ordered from GeneArt (synthetically synthesised for codon optimisation), cut out with restriction enzymes (for tpa-NS1-IMX313) and inserted downstream of the CMV promoter into the pVAX vector (FIG. 3—Thermo Fisher Scientific—catalogue number V26020) to form a tPA-NS1-IMX313 vector.

PCR amplification was used to produce codon optimized nucleic acid encoding tPA-NS1 from the tPA-NS1-IMX313 vector. The amplicons were ligated with restriction enzymes, and the ligated DNA was inserted into the pVax vector to produce a tPA-NS1 vector (FIG. 4).

PCR amplification was also used to produce codon optimized nucleic acid encoding NS1 from the tPA-NS1-IMX313 vector. The amplicons were ligated with restriction enzymes, and the ligated DNA was inserted into the pVax vector to produce a wtNS1 vector (FIG. 4).

The three vectors were transformed in DH5 alpha *E coli* bacteria; cultures were grown over night; and plasmids were either isolated for further cloning using Qiagen mini prep kit, or for administration to animals using an endotoxin free Qiagen GIGA kit. Following isolation plasmids were stored until needed.

The four plasmids produced are illustrated in FIG. 4, and are denoted as follows:
Control (C) unmodified pVAX1 vector.
wtNS1 The pVax plasmid was restricted and ligated with codon optimized DNA encoding the wild-type NS1 protein of Zika virus as set forth in SEQ ID NO: 4 encoding for the protein set forth in SEQ ID NO: 1 (Zika NS1 protein)
tPA-NS1 The pVax vector was restricted and ligated with a codon optimized DNA encoding the tissue plasminogen activator (tPA) signal sequence as set forth in SEQ ID NO: 6 and codon optimized DNA encoding the NS1 protein of Zika virus as set forth in SEQ ID NO: 4.

NS1 heptamer The pVax vector was restricted and ligated with a codon optimized DNA encoding the tissue plasminogen activator (tPA) signal sequence as set forth in SEQ ID NO: 6 linked to DNA encoding the NS1 protein of Zika virus as set forth in SEQ ID NO: 4 which was linked to a sequence encoding IMX313P, which when expressed produces an oligomer (heptamer) version of the NS1 protein (see Tomusange, K et al. Sci Rep., 6:29131.

IMX313P is the oligomerisation domain of the C4 binding protein and has been shown to oligomerise monomer proteins into heptamers. Use of this fusion protein have been demonstrated to act as a potent adjuvant for purified protein antigens in murine models of vaccination (Kask, L. et al., Biochemistry 2002; 41(30): 9349-9357; and Ogun et al., Infect Immun. 2008; 76(8):3817-23).

Immunogenicity of NS1 DNA Vectors

To assess the ability of the prepared vectors to induce a humoral immune response, four groups of female Balb/c mice (n=7 per group) group were administered with 50 ug of plasmid vaccine on day 0, 14 and 28 (see FIG. 5), blood was collected from the mice via cheek bleeds on, day 14 (bleed 1), day 28 (bleed 2), day 42 (bleed 3), day 56 (bleed 4) and day 63 (bleed 5).

Total IgG titres from each bleed was tested by NS1 IgG ELISA as outlined in Brault A. et al. Sci Rep., 7:14769). Briefly, flat-bottom 96-well plates (ThermoFisher Scientific) were coated overnight at 4° C. with ZIKV NS1 protein (Sino Biological) at 1 μg/mL in PBS. The plates were washed 4 times with phosphate buffered saline (PBS)+0.05% Tween-20 (PBST) and then blocked with StartingBlock Block Buffer (ThermoFisher Scientific) for 5 minutes at room temperature. Serially diluted mouse serum samples were added to wells, incubated at 37° C. for 1 h, and the plates washed 4 times. Bound antibodies were detected using HRP-conjugated goat anti-mouse IgG (GE Healthcare Life Sciences) and the OD read at 492 nm.

To assess the IgG2a antibody isotype, the anti-NS1 humoral response antibodies were captured as described above and detected using HRP-conjugated anti-mouse IgG2a (GE Healthcare Life Sciences). Endpoint titers were determined as the reciprocal of the highest serum sample dilution with an OD reading above the cut-off, set as 2 standard-deviations above the mean OD of serum samples from pre-vaccinated or naïve mice.

As can be seen from FIGS. 6A to 6D, the titers induced by the tPA-NS1 DNA vaccine were statistically significantly higher than those induced by wtNS1 or NS1 secreted as a heptamer. tPA-NS1 vaccination resulted in 4 log titers of ZIKV NS1-specific antibodies. NS1 antibody titers increased 1 log each following the second (day 14) and third (day 28) vaccine boosts and remained steady (4 log titre) for at least four weeks following the last vaccination.

Specifically, at day 14 (FIG. 6A) all three NS1 containing DNA vectors induced a statistically significant ($*p \leq 0.05$) increase in the total IgG titre, when compared to the control pVAX vector, with 6/7 mice showing an increase in IgG titre.

Further, at day 28 (FIG. 6B) only mice administered the tPA-NS1 DNA vector showed a statistically significant ($**p \leq 0.01$) increase in IgG titre compared to the control (with 6/7 mice having an elevated IgG titre), while the wtNS1 and the NS1 heptamer groups of treated mice were not significantly increased compared to controls (with only 4/7 individuals having elevated IgG1 titres in both groups).

On day 42 (FIG. 6C) (two weeks after the third dose) the wtNS1 and the NS1 heptamer groups of treated mice were not significantly increased compared to controls (with only 4/7 individuals and 3/7 individuals having elevated IgG1 titres, respectively). However, all seven mice in the tPA-NS1 group had elevated IgG titres, with the group having a statistically significant (***p≤0.001) increase in IgG titre compared to all other treatment groups.

By day 56, (FIG. 6D) only one individual in the wtNS1 group had an elevated IgG titre and all mice in the NS1 heptamer group had reverted to base line. In comparison, all seven mice in the tPA-NS1 group demonstrated an elevation in their IgG titres and the tPA-NS1 treated mice demonstrated a statistically significant (***p≤0.001) increase compared to all other treatment groups.

Isotyping IgG Response

The IgG isotype profile of blood collected on day 63 was assessed by NS1 ELISA (as above) using a secondary HRP-conjugated antibody specific for IgG2a.

Assessment of the IgG isotype antibodies in blood samples taken on day 56 (bleed 4-4 weeks after the final vaccine dose) is illustrated in FIG. 7 and indicates that high IgG2a isotype antibodies were only induced by administration of tPA-NS1 DNA vaccine. IgG2a antibodies are the primary antibody associated with the induction of antibody dependent cell-mediated cytotoxicity (ADCC). As such, it is postulated, in the present context, that the presence of high IgG2a antibody titres may indicate at a degree of protective immunity from the administration of the secreted form of NS1 (tPA-NS1 DNA vaccine) while the membrane bound form (wtNS1) or heptamer form failed to induce such a response.

Dose Response to tPA-NS1 DNA Vector

The humoral immune response to two different dosages of the tPA-NS1 DNA vector was assessed as follows. Two groups of mice were administered 50 μg of the tPA-NS1 vector, two groups were administered 100 μg of the tPA-NS1 vector, and two control groups were administered either 50 μg or 100 μg of the control vector in accordance with the protocol illustrated in FIG. 5 (as discussed above). Blood samples were collected on day 63 and analysed for total IgG titre, as discussed above.

As illustrated in FIG. 8, there were no significant differences between the four treatment groups, indicating that a low dosage of 50 μg is sufficient to induce a humoral immune response.

Example 2—Identification of Immunogenic NS1 Peptides

To identify portions of the 352 amino acid sequence of the Zika NS1 protein involved in inducing an immune response, 114 overlapping synthetic peptides (as shown in Table 5) between 10 and 15 amino acids in lengths having known sequences, and which spanned the length of the 352 amino acid sequence set forth in SEQ ID NO: 1, were obtained from the National Institutes for Health Bio Defense and Emerging Infectious Research Resources Repository (NIAID), National Institutes of Health.

TABLE 5

Synthetic peptides

| Peptide Number | Sequence | SEQ ID NO: |
|---|---|---|
| 1 | GCSVDFSKKETRCGT | 18 |
| 2 | VDFSKKETRCGTGVF | 19 |
| 3 | SKKETRCGTGVFVYN | 20 |
| 4 | ETRCGTGVFVYNDVE | 21 |
| 5 | CGTGVFVYNDVEAWR | 22 |
| 6 | GVFVYNDVEAWRDRY | 23 |
| 7 | VYNDVEAWRDRYKYH | 24 |
| 8 | DVEAWRDRYKYHPDS | 25 |
| 9 | AWRDRYKYHPDSPRR | 26 |
| 10 | DRYKYHPDSPRRLAA | 27 |
| 11 | KYHPDSPRRLAAAVK | 28 |
| 12 | PDSPRRLAAAVKQAW | 29 |
| 13 | PRRLAAAVKQAWEDG | 30 |
| 14 | LAAAVKQAWEDGICG | 31 |
| 15 | AVKQAWEDGICGISS | 32 |
| 16 | QAWEDGICGISSVSR | 33 |
| 17 | EDGICGISSVSRMEN | 34 |
| 18 | ICGISSVSRMENIMW | 35 |
| 19 | ISSVSRMENIMWRSV | 36 |
| 20 | VSRMENIMWRSVEGE | 37 |
| 21 | MENIMWRSVEGELNA | 38 |
| 22 | IMWRSVEGELNAILE | 39 |
| 23 | RSVEGELNAILEENG | 40 |
| 24 | EGELNAILEENGVQL | 41 |
| 25 | LNAILEENGVQLTVV | 42 |
| 26 | ILEENGVQLIVVVGS | 43 |
| 27 | ENGVQLTVVVGSVKN | 44 |
| 28 | VQLTVVVGSVKNPMW | 45 |
| 29 | WVVGSVKNPMWRGP | 46 |
| 30 | VGSVKNPMWRGPQRL | 47 |
| 31 | VKNPMWRGPQRLPVP | 48 |
| 32 | PMWRGPQRLPVPVNE | 49 |
| 33 | RGPQRLPVPVNELPH | 50 |
| 34 | QRLPVPVNELPHGWK | 51 |
| 35 | PVPVNELPHGWKAWG | 52 |
| 36 | VNELPHGWKAWGKSY | 53 |
| 37 | LPHGWKAWGKSYFVR | 54 |
| 38 | GWKAWGKSYFVRAAK- | 55 |
| 39 | AWGKSYFVRAAKTNN | 56 |
| 40 | KSYFVRAAKTNNSFV | 57 |
| 41 | FVRAAKTNNSFVVDG | 58 |
| 42 | AAKTNNSFVVDGDTL | 59 |
| 43 | TNNSFVVDGDTLKEC | 60 |
| 44 | SFVVDGDTLKECPLK | 61 |
| 45 | VDGDTLKECPLKHRA | 62 |
| 46 | DTLKECPLKHRAWNS | 63 |
| 47 | KECPLKHRAWNSFLV | 64 |
| 48 | PLKHRAWNSFLVEDH | 65 |
| 49 | HRAWNSFLVEDHGFG | 66 |
| 50 | WNSFLVEDHGFGVFH | 67 |
| 51 | FLVEDHGFGVFHTSV | 68 |
| 52 | EDHGFGVFHTSVWLK | 69 |
| 53 | GFGVFHTSVWLKVRE | 70 |
| 54 | VFHTSVWLKVREDYS | 71 |
| 55 | TSVWLKVREDYSLEC | 72 |
| 56 | WLKVREDYSLECDPA | 73 |
| 57 | VREDYSLECDPAVIG | 74 |
| 58 | DYSLECDPAVIGTAV | 75 |
| 59 | LECDPAVIGTAVKGK | 76 |
| 60 | DPAVIGTAVKGKEAV | 77 |
| 61 | VIGTAVKGKEAVHSD | 78 |
| 62 | TAVKGKEAVHSDLGY | 79 |
| 63 | KGKEAVHSDLGYWIE | 80 |
| 64 | EAVHSDLGYWIESEK | 81 |
| 65 | HSDLGYWIESEKNDT | 82 |
| 66 | LGYWIESEKNDTWRL | 83 |
| 67 | WIESEKNDTWRLKRA | 84 |
| 68 | SEKNDTWRLKRAHLI | 85 |
| 69 | NDTWRLKRAHLIEMK | 86 |
| 70 | WRLKRAHLIEMKTCE | 87 |
| 71 | KRAHLIEMKTCEWPK | 88 |
| 72 | HLIEMKTCEWPKSHT | 89 |
| 73 | EMKTCEWPKSHTLWT | 90 |
| 74 | TCEWPKSHTLWTDGI | 91 |
| 75 | WPKSHTLWTDGIEES | 92 |
| 76 | SHTLWTDGIEESDLI | 93 |

TABLE 5-continued

Synthetic peptides

| Peptide Number | Sequence | SEQ ID NO: |
|---|---|---|
| 77 | LWTDGIEESDLIIPK | 94 |
| 78 | DGIEESDLIIPKSLA | 95 |
| 79 | EESDLIIPKSLAGPL | 96 |
| 80 | DLIIPKSLAGPLSHH | 97 |
| 81 | IPKSLAGPLSHHNTR | 98 |
| 82 | SLAGPLSHHNTREGY | 99 |
| 83 | GPLSHHNTREGYRTQ | 100 |
| 84 | SHHNTREGYRTQMKG | 101 |
| 85 | NTREGYRTQMKGPWH | 102 |
| 86 | EGYRTQMKGPWHSEE | 103 |
| 87 | RTQMKGPWHSEELEI | 104 |
| 88 | MKGPWHSEELEIRFE | 105 |
| 89 | PWHSEELEIRFEECP | 106 |
| 90 | SEELEIRFEECPGTK | 107 |
| 91 | LEIRFEECPGTKVHV | 108 |
| 92 | RFEECPGTKVHVEET | 109 |
| 93 | ECPGTKVHVEETCGT | 110 |
| 94 | GTKVHVEETCGTRGP | 111 |
| 95 | VHVEETCGTRGPSLR | 112 |
| 96 | EETCGTRGPSLRSIT | 113 |
| 97 | CGTRGPSLRSTTASG | 114 |
| 98 | RGPSLRSTTASGRVI | 115 |
| 99 | SLRSTTASGRVIEEW | 116 |
| 100 | STTASGRVIEEWCCR | 117 |
| 101 | ASGRVIEEWCCRECT | 118 |
| 102 | RVIEEWCCRECTMPP | 119 |
| 103 | EEWCCRECTMPPLSF | 120 |
| 104 | CCRECTMPPLSFRAK | 121 |
| 105 | ECTMPPLSFRAKDGC | 122 |
| 106 | MPPLSFRAKDGCWYG | 123 |
| 107 | LSFRAKDGCWYGMEI | 124 |
| 108 | RAKDGCWYGMEIRPR | 125 |
| 109 | DGCWYGMEIRPRKEP | 126 |
| 110 | WYGMEIRPRKEPESN | 127 |
| 111 | MEIRPRKEPESNLVR | 128 |
| 112 | RPRKEPESNLVRSMV | 129 |
| 113 | KEPESNLVRSMVTAG | 130 |
| 114 | ESNLVRSMVTAGS | 131 |

The fragment peptides were then formed into four pools, being:

Pool 1—Peptides 1 to 28 which spanned positions 1 to 96 of the NS1 protein.

Pool 2—peptides 29 to 57, which spanned positions 85 to 183 of the NS1 protein.

Pool 3—Peptides 58 to 86, which spanned positions 172 to 270 of the NS1 protein.

Pool 4—Peptides 87 to 114, which spanned between positions 259 to 352 of the NS1 protein.

Splenocytes were isolated from mice administered either: the control vector (empty pVax vector); the pVax vector containing NS1 alone without a signal peptide (wtNS1); the pVax vector containing a heterologous tPA signal peptide linked to NS1 sequence (tPA-NS1—secreted); or the pVax vector containing a heterologous tPA signal peptide linked to NS1 and an IMX313P sequence (heptamer).

The vectors were administered in accordance with the protocol outlined in FIG. 5 (as discussed above), and spleens were collected 2 weeks after the last DNA dose (Day 42). Splenocytes were isolated, depleted of red blood cells, and subsequently cultured in RPMI supplemented with 10% FCS, pen/strep, sodium pyruvate, Hepes and beta-mercaptoethanol at $2 \times 10^5$ cells per well.

Plated cells were administered one of the four pools of peptides (4 ug per well) and incubated at 37 degrees, 5% $CO_2$, for 36 hrs.

The immunogenicity of each pool was assessed via quantitative Interferon-gamma (IFN-γ) ELISpot.

Mouse IFN-γ ELISpot was performed on red blood cell-depleted splenocytes from immunised mice and were stimulated with one of the peptide pools described above for 36h at 37° C.+5% CO2, as described previously (Grubor-Bauk 2016, Wijesundara 2018).

Briefly, multiscreen-IP HTS plates (Merck Millipore, Germany) were coated with anti-mouse IFN-γ (clone AN18, MabTech, Sweden) and secreted IFN-γ detected with anti-mouse IFN-γ-biotin (clone R4-6A2, MabTech), streptavidin-AP (Sigma Aldrich) and SigmaFast BCIP/NBT (Sigma Aldrich)

Developed spots were counted automatically using an ELISpot reader (AID Germany), and the number of spots in unstimulated splenocytes (~0 to 50) subtracted from the number of spots in the peptide pool-stimulated splenocytes to generate the number of specific spot-forming units (SFU) per $10^6$ cells. Data are presented as means±the standard error of the mean (SEM). Statistical analysis was performed using unpaired Mann-Whitney tests, with P≤0.05 (*), P≤0.01 (), and P≤0.001 (*) considered significant. Analysis was performed using GraphPad Prism version 6.00 for Windows (GraphPad Software, La Jolla, Calif.).

As illustrated in FIG. 9, pools 1, 3 and 4 induced an increase in the secretion of IFNγ only in splenocytes cells isolated from mice immunised with tPA-NS1 vaccine, albeit with only pool 3 and 4 showing a statistically significant increase when compared to the control. Interferon gamma production was stimulated primarily by pool 3 and pool 4 indicating that peptides within these pools, spanning positions 172 to 352 of the NS1 protein, were inducing a NS1-specific T cell response in mice vaccinated with tPA-NS1.

Mapping T Cell Epitopes

After identifying pools 3 and 4 as inducing NS1-specific T cell responses, individual peptide from pool 3 and 4 were interrogated for T cell immunogenicity, using fluorescent labelling of individual cell populations which were pulsed with the individual peptides comprising pool 3 and pool 4.

To generate the FTA used in experiments illustrated in FIGS. 10 and 11 splenocytes from 11 naïve mice were pooled, split evenly 5 ways and labelled with either 85, 22.95, 6.21, 1.67 or 0.595 uM CTV. Subsequently, the cells were washed three times using RPMI+5% FCS and the cells from each aliquot were split evenly into three groups. These groups were labelled with either 5.17, 1.46 or 0.441 uM of CFSE to result in 15 distinct populations of target cells (to delineate 5 concentrations of 3 sets of pooled peptides). The different populations were then pulsed with 10 μg/ml of NS1 Pool 1, NS1 Pool 2, NS1 Pool 3, NS1 Pool 4 or Pool 4 without 'immunodominant' peptides 87 and 88.

Four hours after peptide pulsing at 37° C.+5% $CO_2$, the peptide-pulsed targets were washed three times and all the pulsed cells were pooled prior to labelling with 38.65 uM CPD. The labelled cells were washed and resuspended in PBS for intravenous challenge into immunised (tPA-NS1) or control mice ($2.25 \times 10^7$ cells ($1.5 \times 10^6$ cells per target cell population) in 200 μl of PBS/mouse). Fifteen hours later, the splenocytes were harvested, depleted of red blood cells, stained with B220 and CD69 and analysed by flow cytometry (BD FACS Canto II) as described in Wijesundara et al. 2018; J Virol. Flowjo Tree Star (version 8.8.7) software was used to generate the flow cytometry plots.

Fluorescent cell labelling and peptide pulsing were performed as described (Wijesundara D. K., J Virol. 2006, 28; 92(8)). To generate the FTA used in the experiments illustrated in FIGS. 12 to 15, splenocytes from naïve mice were pooled, split and labelled with various concentrations of CTV and CFSE as set out in the tables below. The different populations were then pulsed with individual peptides.

Four hours after peptide pulsing at 37° C.+5% $CO_2$, the peptide-pulsed targets were washed three times and all the pulsed cells were pooled prior to labelling with CPD. The labelled cells were washed and resuspended in PBS for intravenous challenge into immunised (tPA-NS1) or control immunised mice. Fifteen hours later, the splenocytes were harvested from the mice, depleted of red blood cells, stained with B220 and CD69 and analysed by flow cytometry (BD FACS Canto II) as described in Wijesundara et al 2018; J Virol. Flowjo Tree Star (version 8.8.7) software was used to generate the flow cytometry plots.

| 2.7 mM CPD | | | | | | |
|---|---|---|---|---|---|---|
| | 0 mM | 0.05 mM CTV | 0.19 mM CTV | 0.73 mM CTV | 2.7 mM CTV | 10 mM CTV |
| 2.7 mM CFSE | Mock (a) | 58 (b) | 59 (c) | 60 (d) | 61 (e) | 62 (f) |
| 0.82 mM CFSE | 63 (g) | 64 (h) | 65 (i) | 66 (j) | 67 (k) | 68 (l) |
| 0.23 mM CFSE | 69 (m) | 70 (n) | 71 (o) | 72 (p) | 73 (q) | 74 (r) |
| 0.08 mM CFSE | 75 (s) | 76 (t) | 77 (u) | 78 (v) | 79 (w) | 80 (x) |
| 0 mM CFSE | 81 (y) | 82 (z) | 83 (1) | 84 (2) | 85 (3) | 86 (4) |

| 10 mM CPD | | | | | | |
|---|---|---|---|---|---|---|
| | 0 mM | 0.05 mM CTV | 0.19 mM CTV | 0.73 mM CTV | 2.7 mM CTV | 10 mM CTV |
| 2.7 mM CFSE | 87 (a) | 88 (b) | 89 (c) | 90 (d) | 91 (e) | 92 (f) |
| 0.82 mM CFSE | 93 (g) | 94 (h) | 95 (i) | 96 (j) | 97 (k) | 98 (l) |
| 0.23 mM CFSE | 99 (m) | 100 (n) | 101 (o) | 102 (p) | 103 (q) | 104 (r) |
| 0.08 mM CFSE | 105 (s) | 106 (t) | 107 (u) | 108 (v) | 109 (w) | 110 (x) |
| 0 mM CFSE | 111 (y) | 112 (z) | 113 (1) | 114 (2) | P3 (3) | P4 (4) |

The percentage of specific FTA loss (as a measure of CTL activity) was calculated using the formula, ((mock target—peptide-pulsed targets)/mock targets)×100. GraphPad Prism 6 software was used to construct the graphs presented in this study.

Cytotoxic T lymphocyte (CTL) responses from the control vaccinated mice or the tPA-NS1 vaccinated mice (FIGS. 12 and 13) and wtNS1 and heptamer vaccinated mice (FIG. 10) were analysed by assessing the in vivo killing of distinct populations of cells (i.e. population having a distinct CFSE, CPD and CTV profile).

Figure 13:
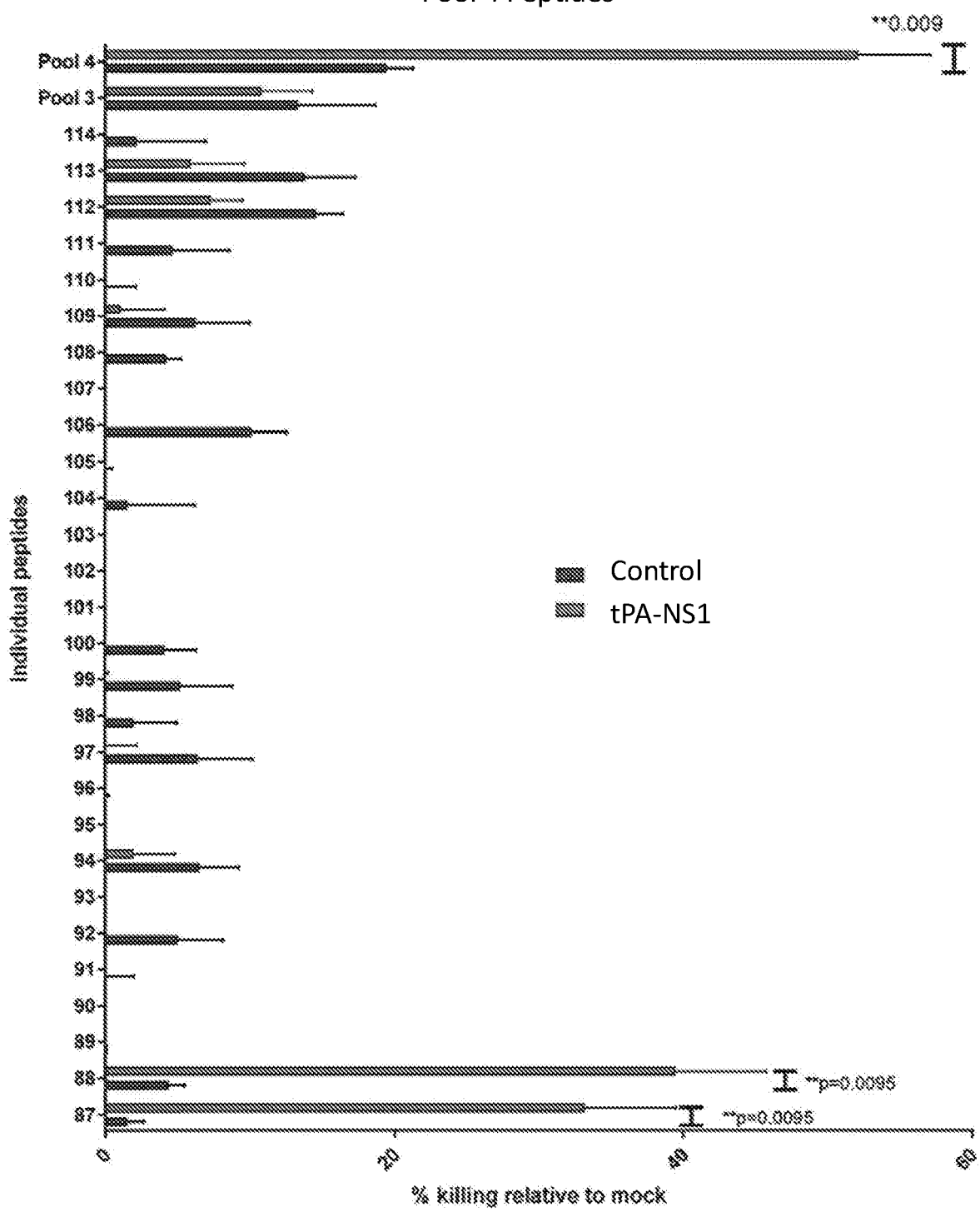

FIG. 13 illustrates the relative killing of cells pulsed with individual peptides 87 to 114, which comprise Pool 4, as well as cells pulsed with Pool 3 peptides and Pool 4 peptides. Notably cells pulsed with peptides 87 and 88 were killed at a statistically significantly higher rate in tPA-NS1 treated mice compared to control treated mice, indicating that these peptides contain CTL (MHC class I restricted) epitopes for cell populations induced by the tPA-NS1 DNA vaccine.

Figure 19:
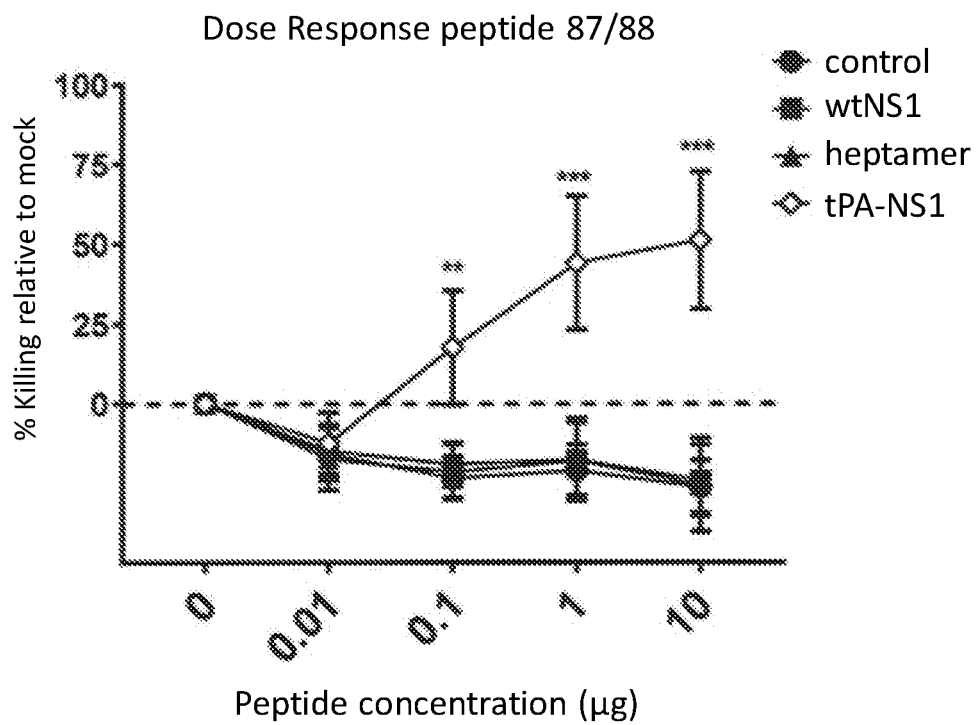
Figure 20:
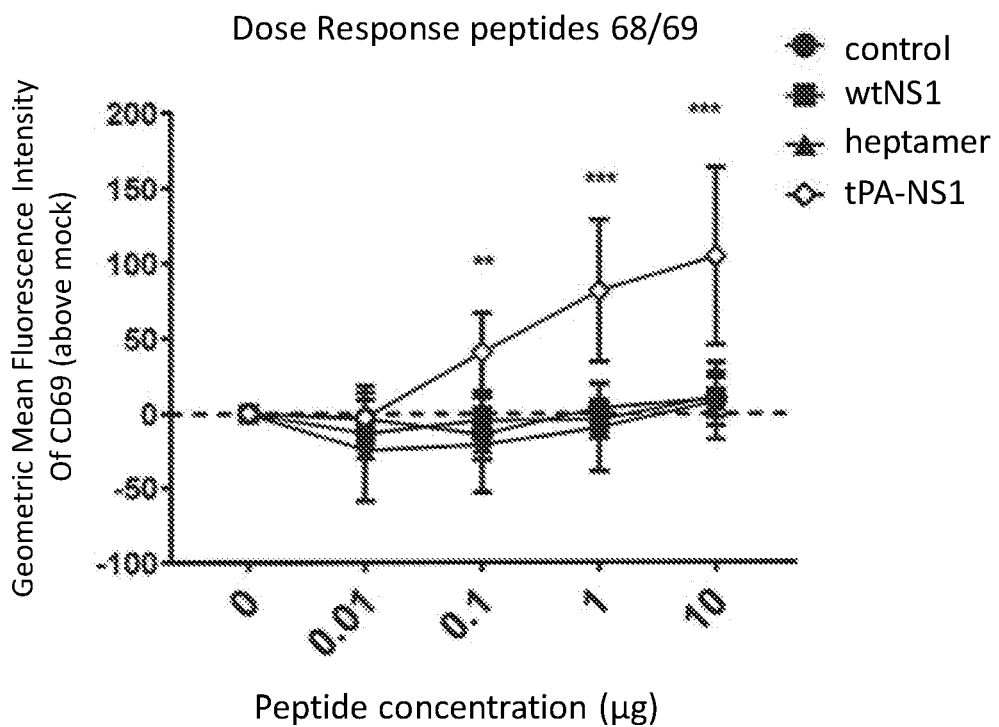

The dose response of CTL killing and T helper responses to peptides 87 and 88 and peptides 68 and 69 are illustrated in FIGS. 19 and 20.

Upon recognition of cognate antigens, T helper (Th) cells co-stimulate B cells, which leads to upregulation of CD69 on mature (B220+) B cells. Consequently, in vivo T helper responses from the control vaccinated mice and the tPA-NS1 vaccinated mice were analysed by assessing the activation of B220+ B cell populations within each distinct population of peptide pulsed cells (i.e. each population having a distinct CFSE, CPD and CTV profile). Specifically, the expression (as determined by the geometric mean fluorescence intensity—GMFI) of the activation marker CD69 was assessed on each of distinct populations of cells which had been pulsed with pooled peptides, or individual peptides from pool 3 and pool 4 from both the control treated mice and NS1 vaccinated mice.

Figure 11:
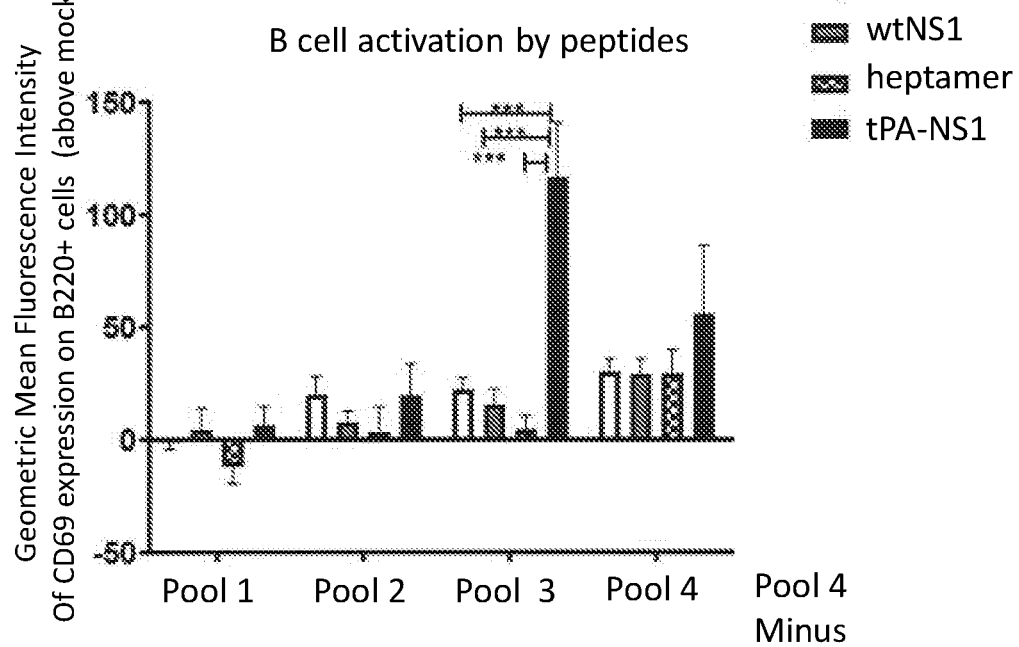
Figure 12:
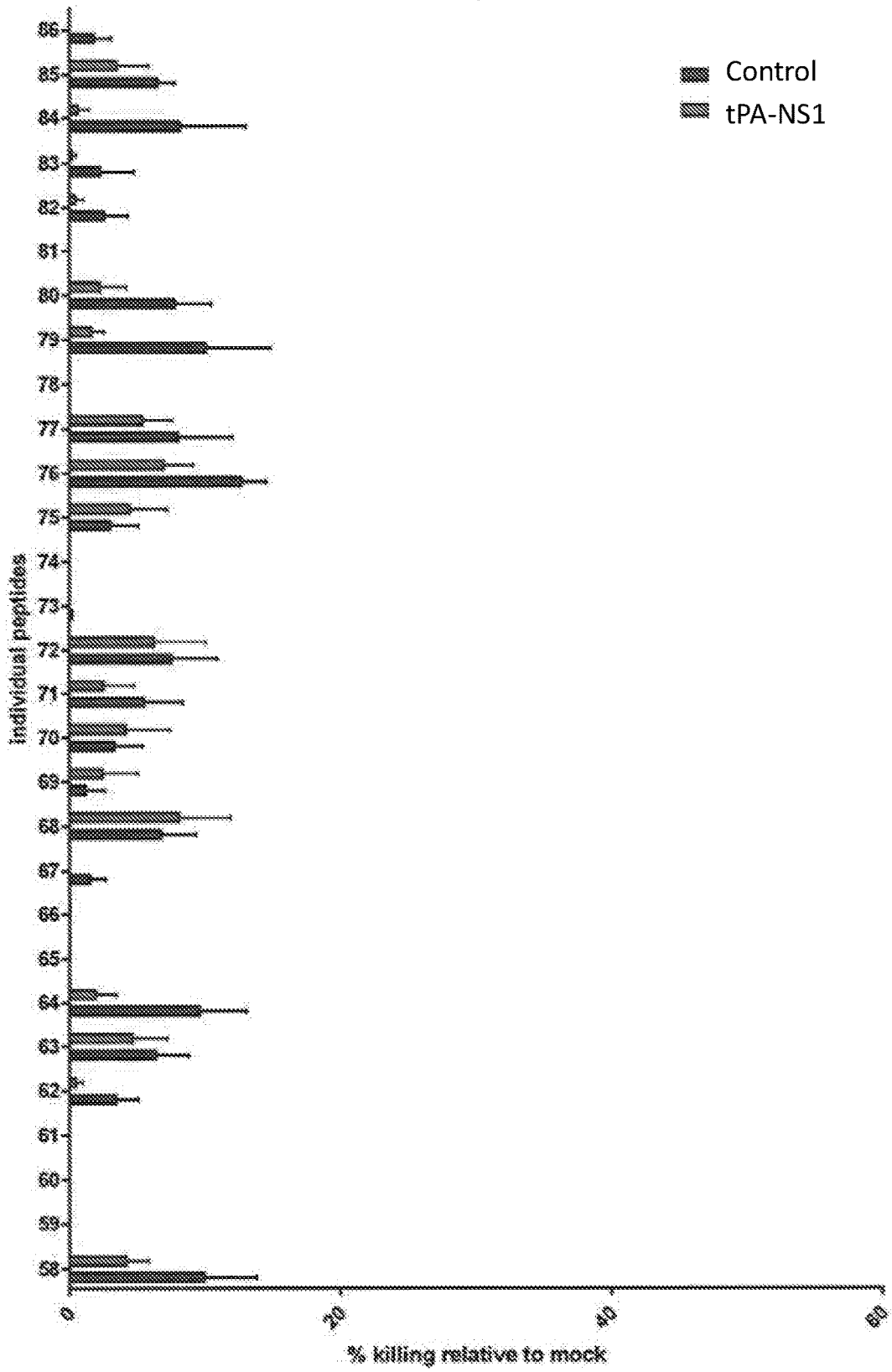
FIG. 12 illustrates the relative killing of cells pulsed with individual peptides 58 to 86, which comprise Pool 3. No significant difference was discernible between peptide pulsed cells in the control treated animals and the tPA-NS1 treated animals.

FIG. 11 illustrates that primarily Pool 3, activated T helper responses (as indicated by an increase in CD69 expression in B220+ cells) in mice vaccinated with the tPA-NS1 vector. While mice vaccinated with the control pVax vector; the wtNS1 vector; or the vector containing the tPA-NS1-IMX313P (heptamer), did not demonstrate significant T helper responses.

Figure 14:
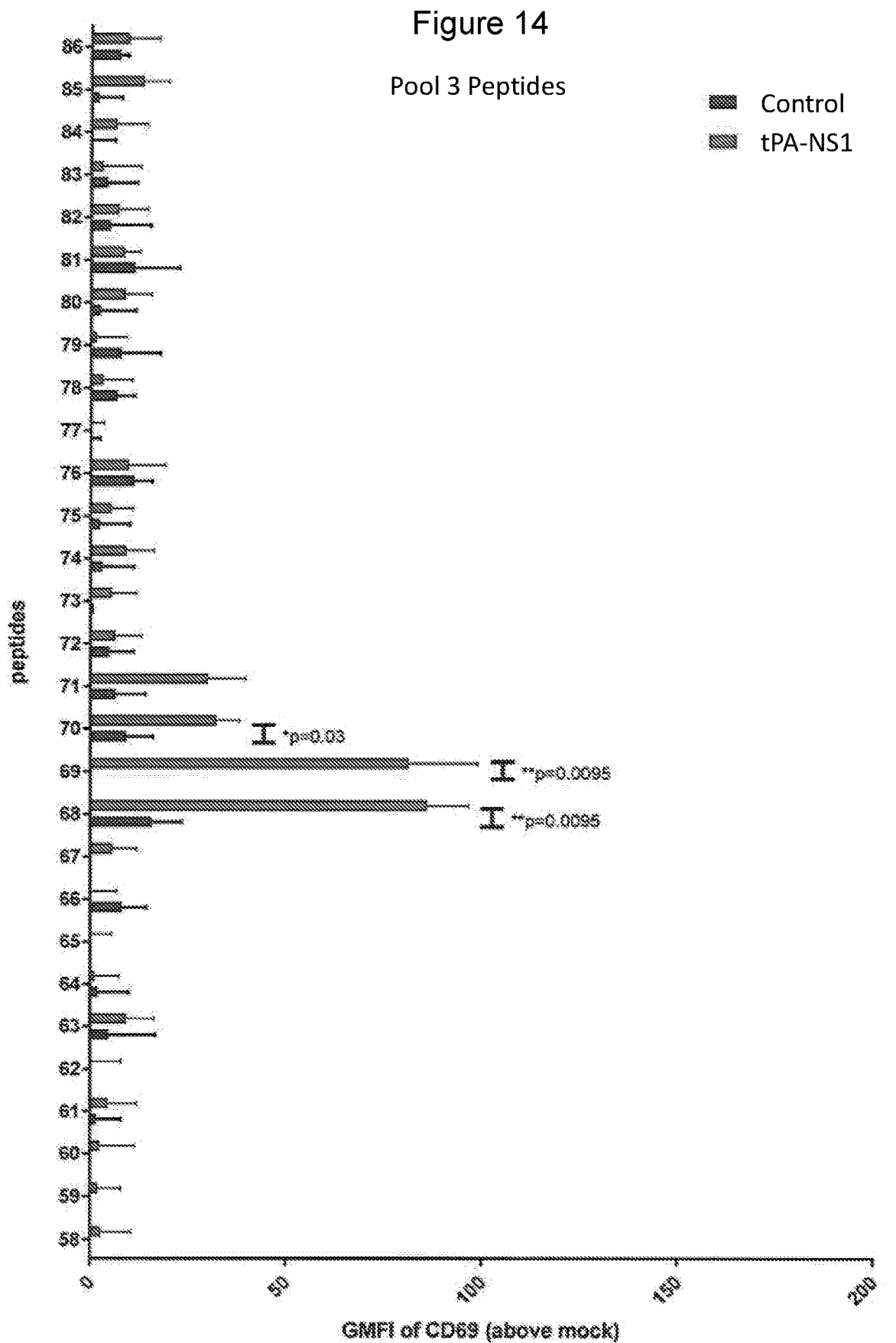
Figure 15:
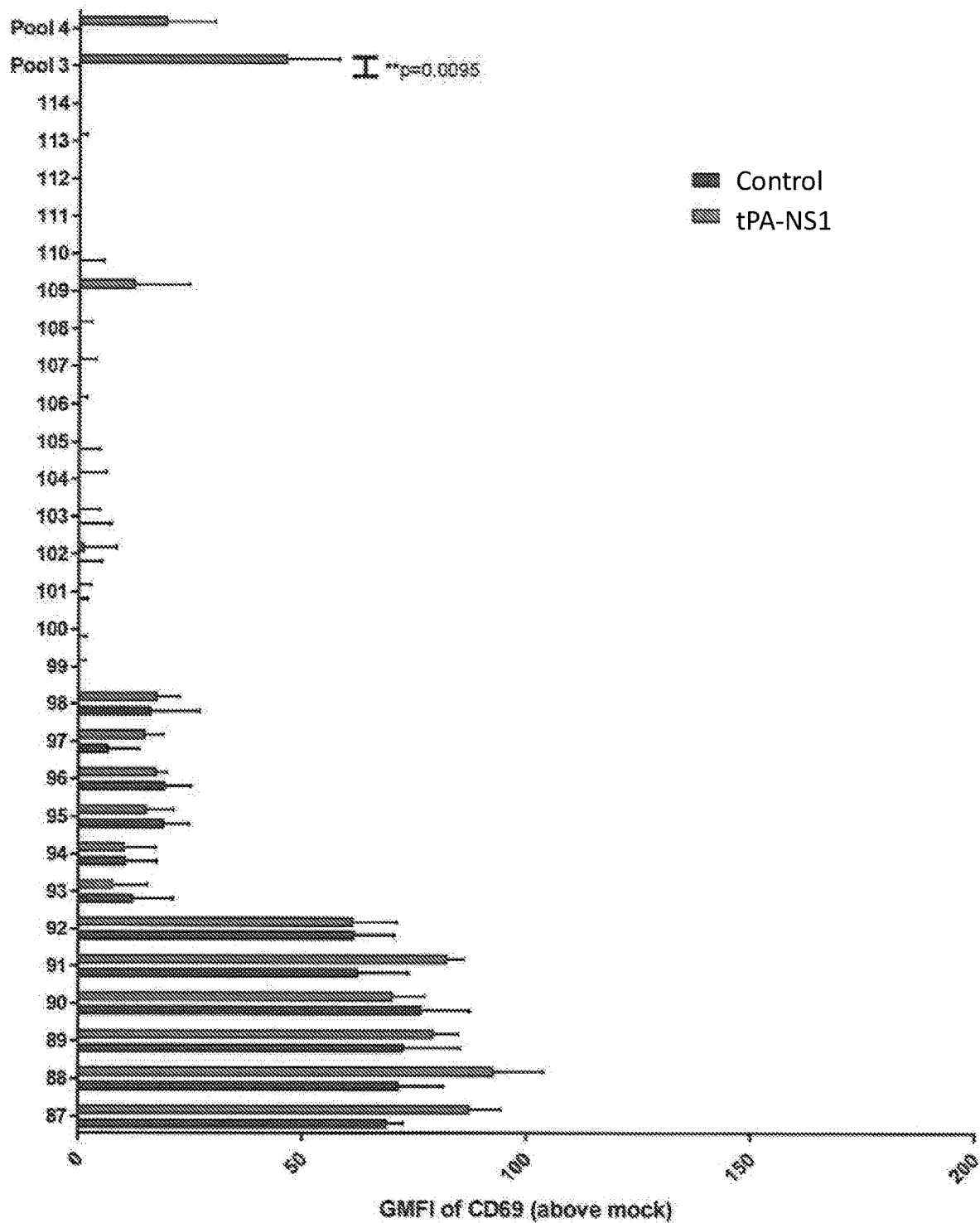

The T helper response of cell populations in control treated animals and tPA-NS1 treated animals is illustrated in FIG. 14 (Pool 3 peptides) and FIG. 15 (Pool 4 peptides).

FIG. 14 illustrates the GMFI of CD69 expression on cells pulsed with peptides 58 to 86, which comprise Pool 3. Notably cells pulsed with peptides 68 and 69 have a statistically significantly higher expression of CD69 in the tPA-NS1 treated mice compared to control pVax treated mice, indicating that these peptides contain T helper (MHC class II restricted) epitopes for cell populations induced by the tPA-NS1 DNA vaccine.

FIG. 15 illustrates the GMFI of CD69 expression on cells pulsed with peptides 87 to 114, which comprise Pool 4, as well as cell pulsed with aggregated Pool 3 peptides and aggregated Pool 4 peptides. No statistically significant difference was discernible between individual peptide pulsed cells in the control treated animals compared to the tPA-NS1 treated animals. However, consistent with the results in FIG. 14, Pool 3 showed a statistically significant increase in CD69 expression in the tPA-NS1 treated animals compared to control pVax treated animals.

Overall the in vivo FTA data demonstrates that immunisation with the tPA-NS1 vector induced strong CD8+ and CD4+ T cell responses and that these responses are likely driven by the recognition of T cell epitopes present in the C-terminus (amino acids 172-352) of the ZIKV$_{PRVABC59}$ NS1 protein.

Confirmation of Epitopes

The results in FIGS. 12 to 15 were confirmed by performing IFNg ELISpot (in accordance with the protocol described above) on cells isolated from mice vaccinated with either the control pVax vector, wtNS1 vector, the tPA-NS1 vector or the vector containing the tPA-NS1-IMX313P (heptamer). Isolated splenocytes were administered peptides from Pools 3; peptides from Pool 4, Pool 4 with peptides 88 and 87 removed, peptides 88 and 87 combined, and peptides 68 and 69 combined.

Figure 16:
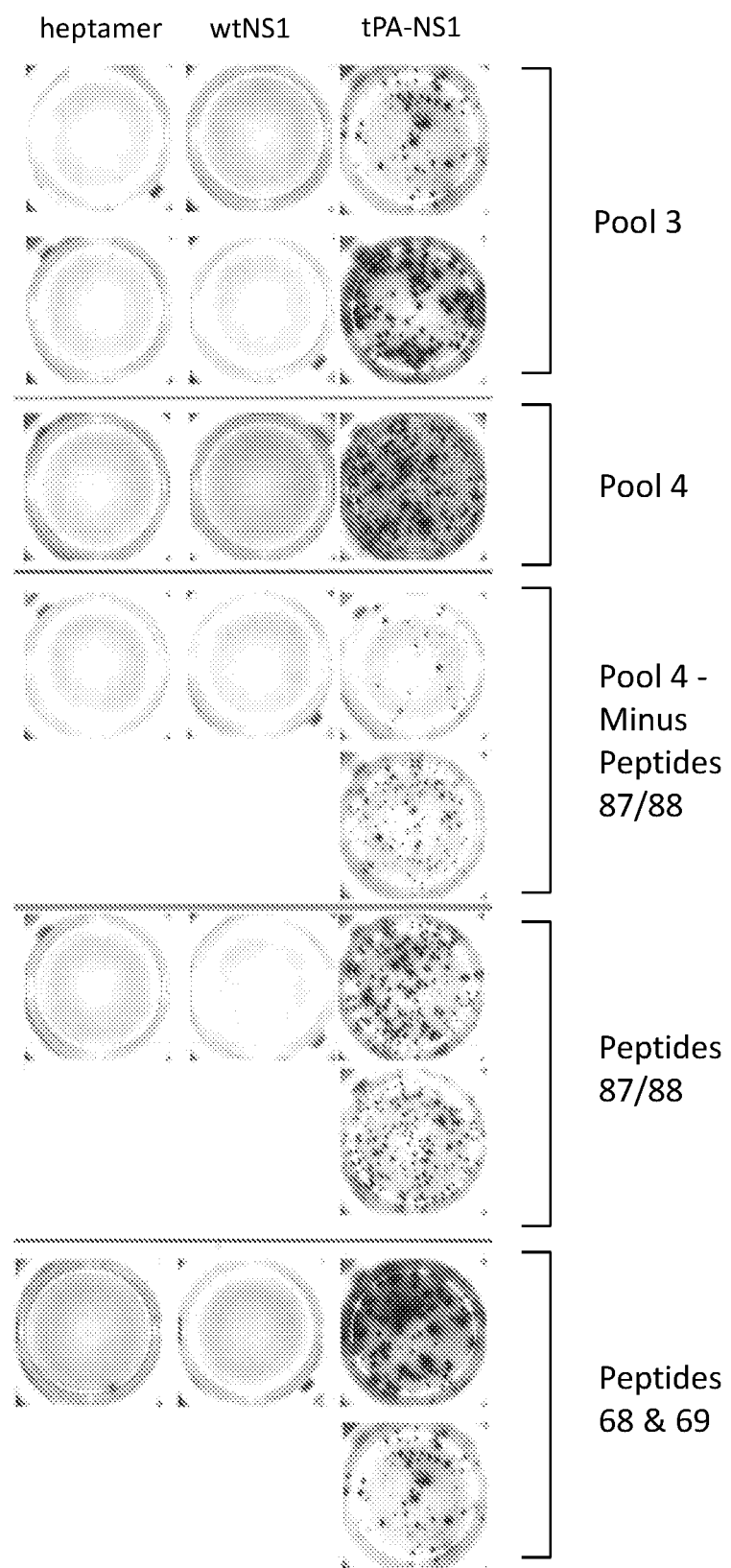

Indicative results are shown in FIG. 16. As can be seen Pools 3 and 4 induce IFNg secretion in cells isolated from tPA-NS1 vaccinated mice, but not wtNS1 vaccinated mice or mice vaccinated with the vector expressing an NS1 heptamer. This induction of IFNg secretion was partially attenuated when peptides 87 and 88 were removed from Pool 4. While the administration, of peptides 88 and 87 together, and peptides 68 and 69 together both induced IFNg secretion. Consequently, these results corroborate the previous findings that the T cell epitopes for NS1 primarily exist in peptides 68, 69, 87 and 88.

Figure 17:
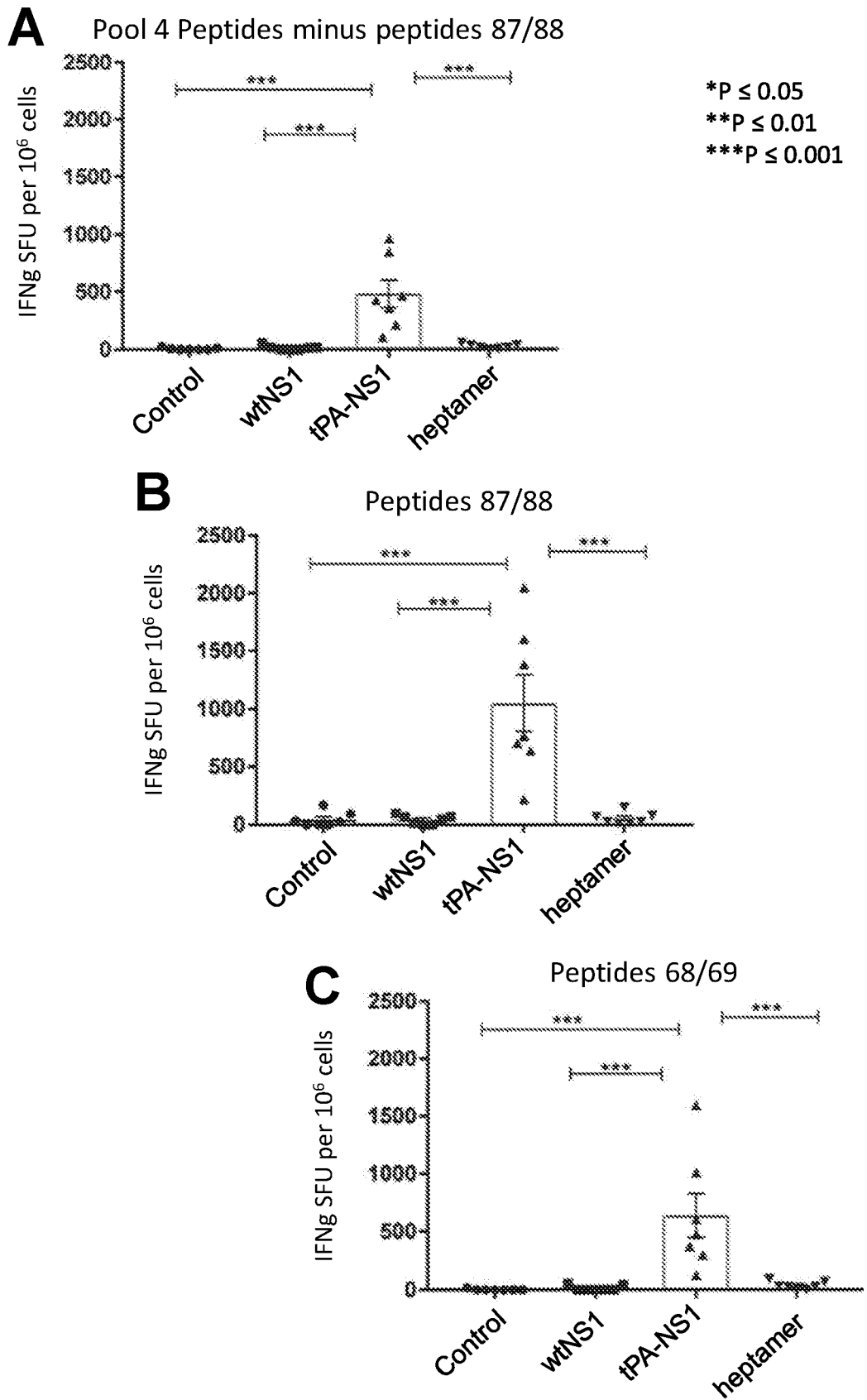

FIGS. 17A-C illustrate quantification of IFNg expression from the ELIspot assays performed on seven mice for each treatment group. As can be seen Pool 4 (FIG. 17-A), peptides 87 and 88 (FIG. 17-B), and peptides 68 and 69 (FIG. 17-C) all induced a statistically significant increase in IFNg secretion in the mice vaccinated with the tPA-NS1 vector, while mice vaccinated with the control, wtNS1 or heptamer vectors showed no increase in IFNg secretion.

Interleukin-2 (IL-2) and IFNg coexpression was assess using a FluoroSpot assay. Animals were vaccinated with either the control pVax vector or the tPA-NS1 vector, in accordance with the protocol set out in FIG. 5. T cells were isolated from animals on day 42 and pulsed with either; Pool 3 peptides, Pool 4 peptides, peptides 87 and 88 or peptides 68 and 69.

A FluoroSpot assay was performed as per manufacturer's instructions using Mouse INFg/IL-2 Fluorospot kit (Mabtech, catalogue FS-4142-2). Mice were treated as per IFNg ELISpot described above.

Figure 18:
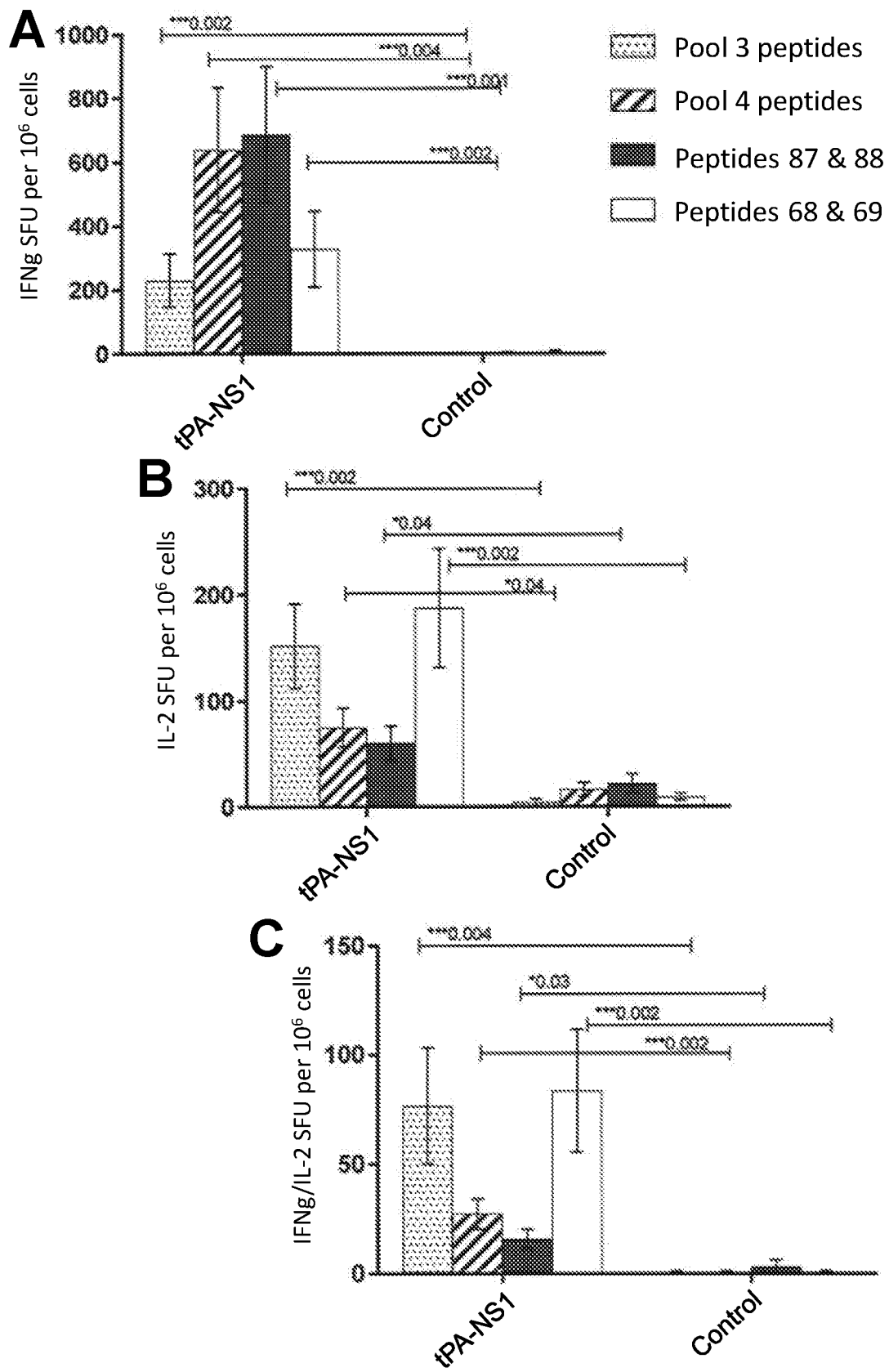

As can be seen in FIGS. 18A-C, IFNg expression was primarily induced by Pool 4 peptides with the increase attributable to peptides 87 and 88 (FIG. 18-A). However IL-2 was primarily induced by Pool 3 peptides, with the increase attributable to peptides 68 and 69 (FIG. 18-B). As can be seen in FIG. 18-C only about half of the IL-2 secreting cell also express IFNg while only a minority of IFNg secreting cells also express IL-2. These results are consistent with Pool 4 and peptides 87 and 88 inducing CTLs, while Pool 3 and peptides 68 and 69 induce T helper cells.

Dose Response to Peptides

Figure 3:
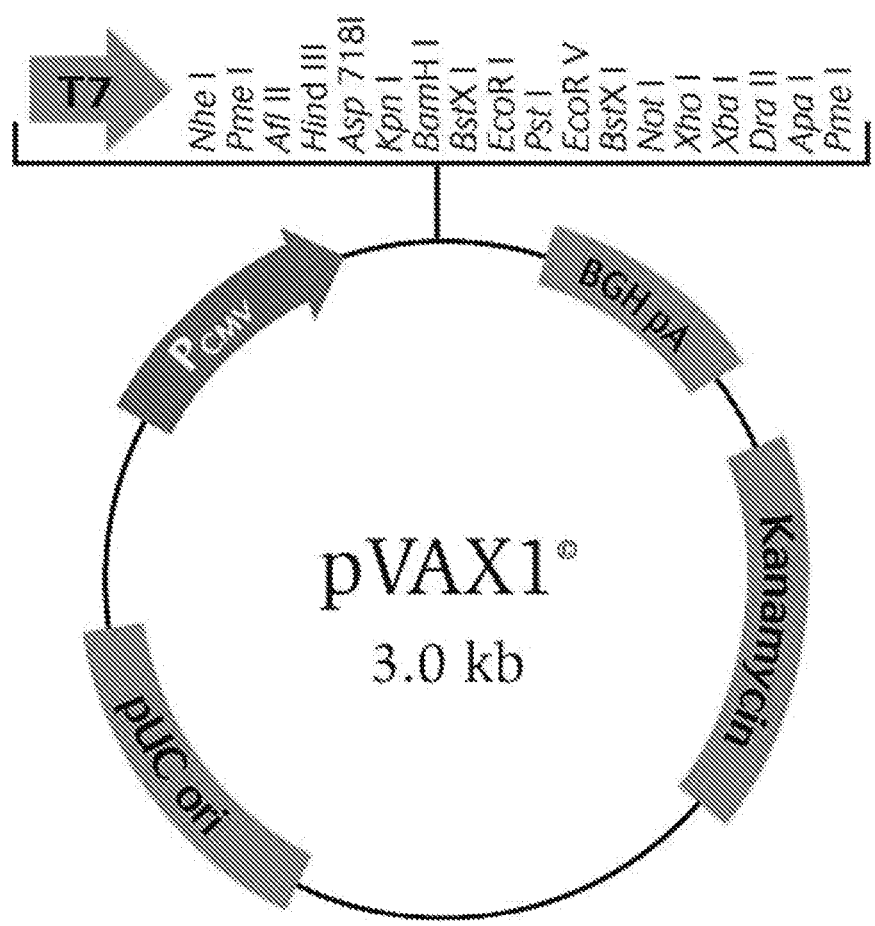
Figure 4:
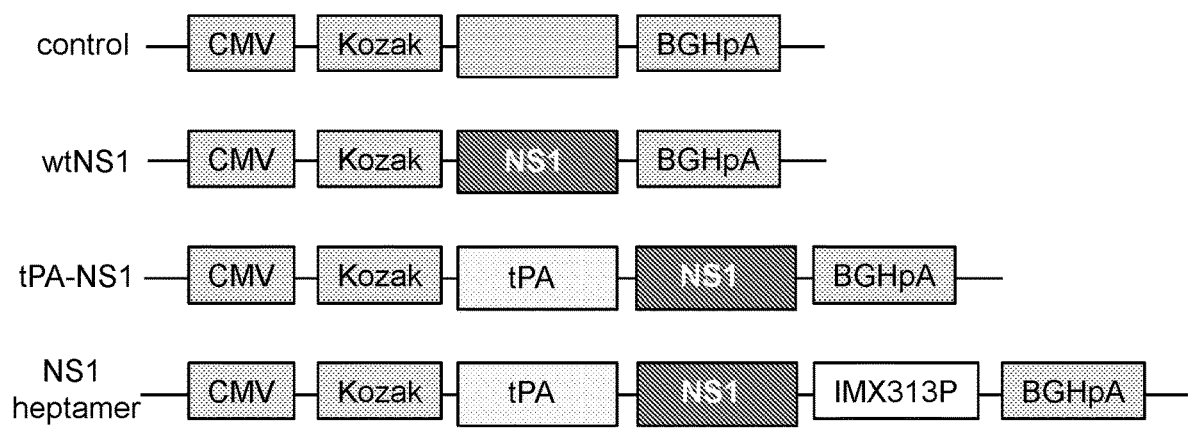
Figure 5:
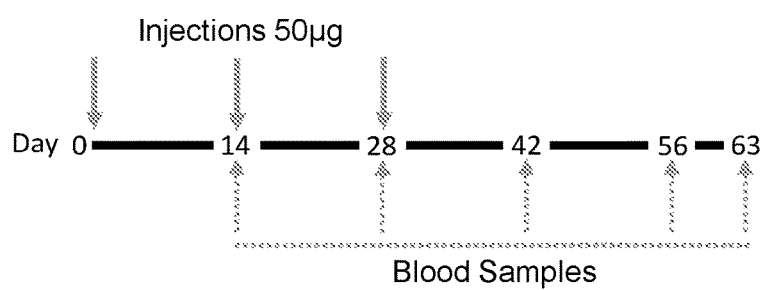
Figure 6:
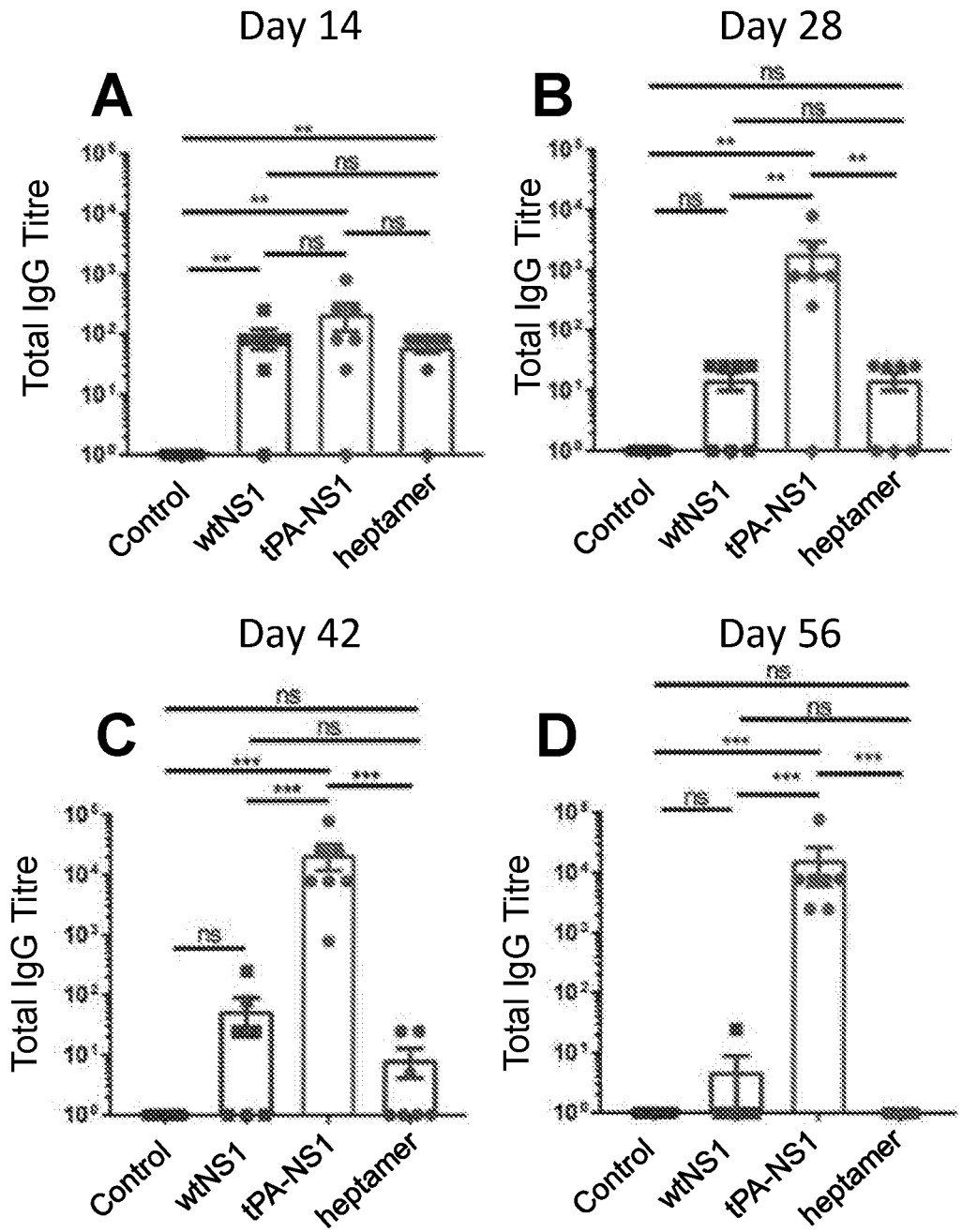
Figure 7:
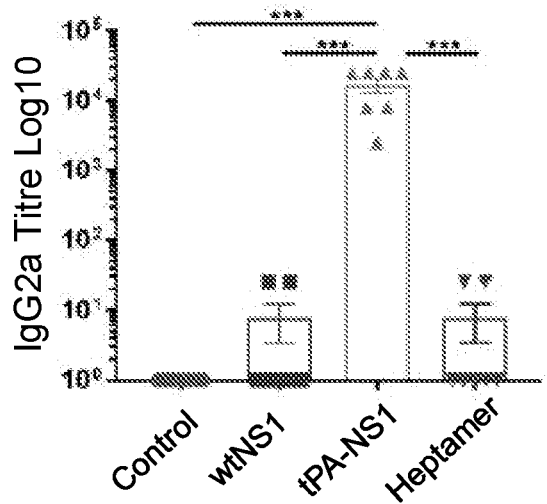
Figure 8:
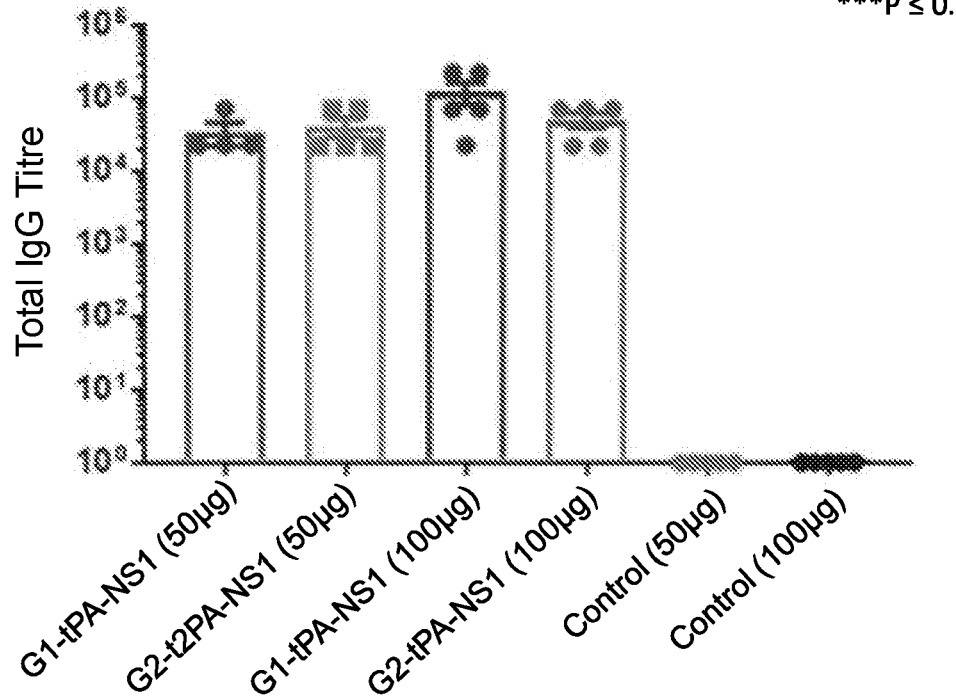
Figure 9:
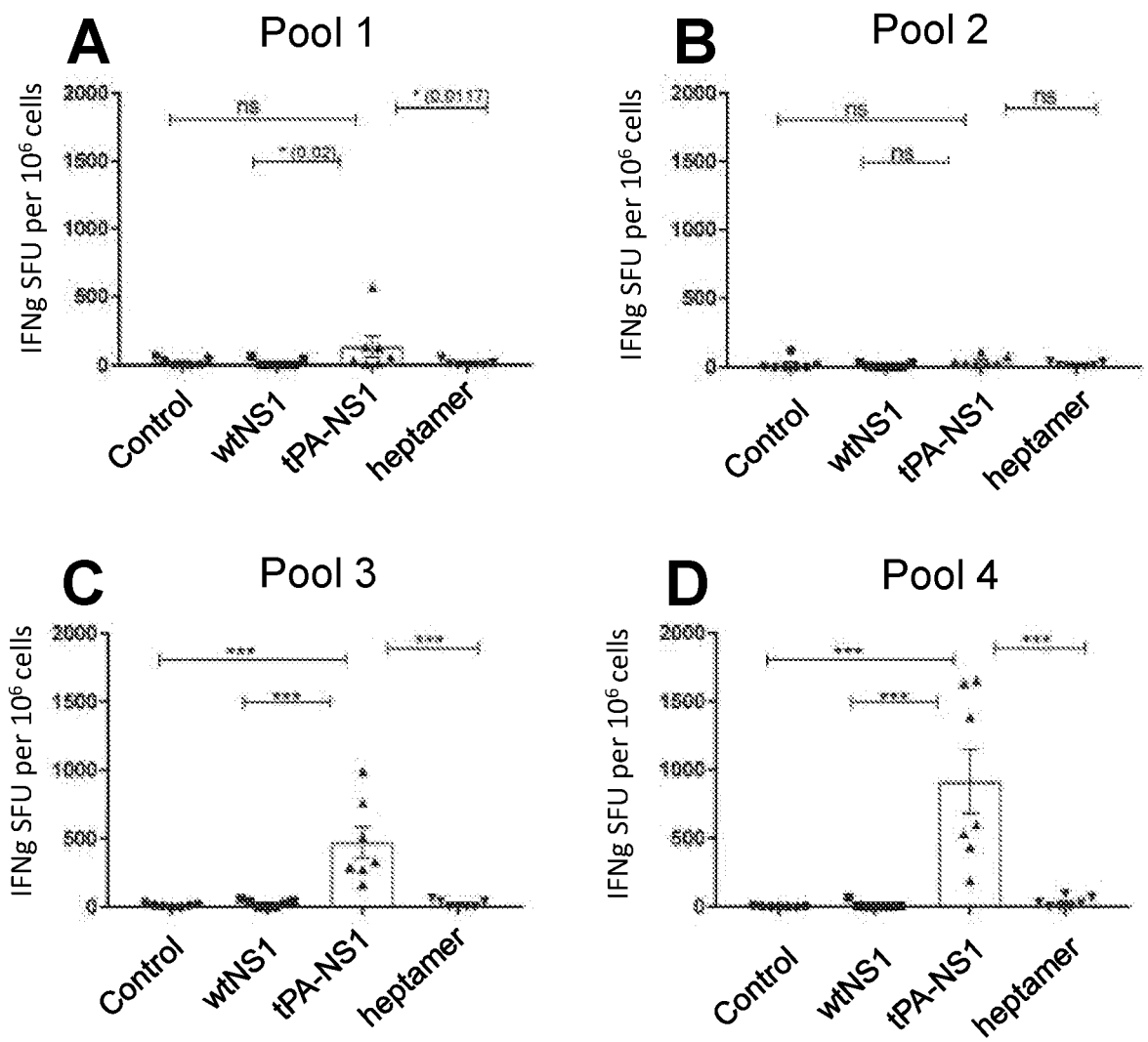
Figure 10:
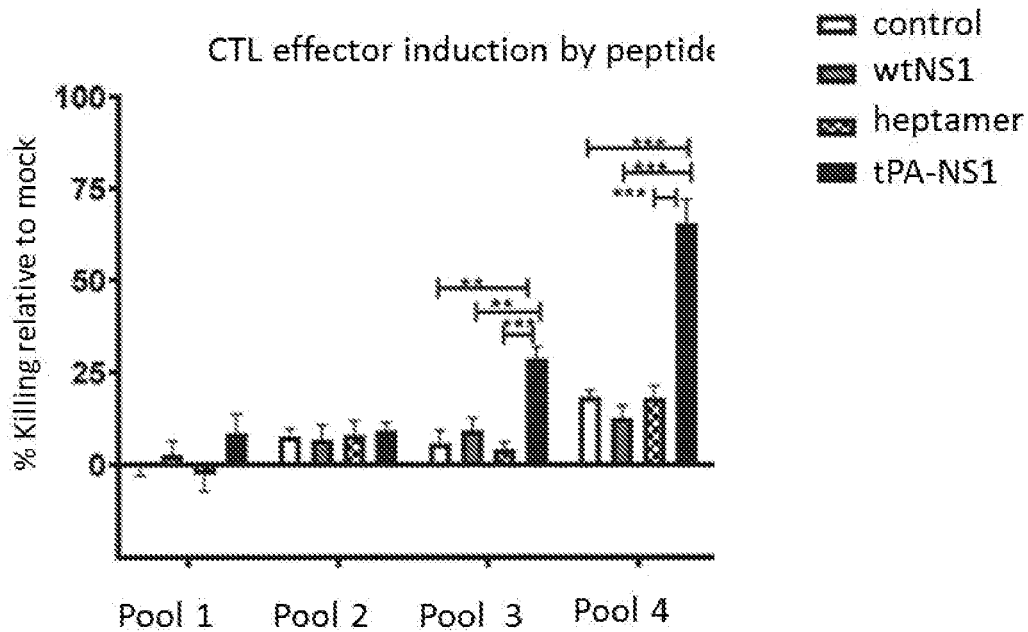
FIG. 10 illustrates that primarily Pool 4 are targets for CTL mediated killing in mice vaccinated with the tPA-NS1 vector. While mice vaccinated with control pVax vector; the wtNS1 vector; or the vector containing the tPA-NS1-IMX313P (heptamer), did not demonstrate killing of target cells.

The effects of the peptides on CTL function and T helper cell activation were assessed in mice vaccinated with either: the control pVax vector; the wtNS1 vector; the tPA-NS1 vector; or the vector containing the tPA-NS1-IMX313P (heptamer) in accordance with the protocol set out in FIG. 5.

To generate the FTA used in experiments described in FIGS. 19 and 20, splenocytes from 11 naïve mice were pooled, split evenly 5 ways and labelled with either 10, 2.7, 0.73, 0.19 or 0.05 mM of CTV. Subsequently, the cells were washed thrice using RPMI+5% FCS and the cells from each aliquot were split evenly 3 ways and these were labelled with either 0.82, 0.23 or 0.08 mM of CFSE to result in 15 distinct populations of target cells (to delineate 5 concentrations of 3 sets of pooled peptides). The different populations were then pulsed with 10 µg/ml, 1 µg/ml, 0.1 µg/ml 0.01 µg/ml or 0 µg/ml of peptides 87 and 89 or peptides 68 and 69.

The arrangement of the FTA matrix for FIGS. 19 and 20 is shown in the table below.

| | 0.05 mM CTV | 0.19 mM CTV | 0.73 mM CTV | 2.7 mM CTV | 10 mM CTV |
|---|---|---|---|---|---|
| 0.82 mM CFSE | Mock (a) | CTL (0.01) | CTL (0.1) | CTL (1) | CTL (10) |
| 0.23 mM CFSE | Mock (b) | Th (0.01) | Th (0.1) | Th (1) | Th (10) |
| 0.08 mM CFSE | P4-ID | P1 | P2 | P3 | P4 |

Four hours after peptide pulsing, the peptide-pulsed targets were washed three times and all the pulsed cells were pooled prior to labelling with 38.65 uM CPD. The labelled cells were washed three times and resuspended in PBS for intravenous challenge into immunised or control mice ($2.25 \times 10^7$ cells ($1.5 \times 10^6$ cells per target cell population) in 200 µl of PBS/mouse). Fifteen hours later, the splenocytes were harvested, depleted of red blood cells, stained with B220 and CD69 and analysed by flow cytometry (BD FACS Canto II). Flowjo Tree Star (version 8.8.7) software was used to generate the flow cytometry plots. As can be seen in FIG. 19, cell killing showed an approximately linear dose response curve, for the dosages of tPA-NS1 vector tested, starting from 0.1 µg to 10 µg, while other vectors showed no notable response.

Comparable results can be seen in FIG. 20, whereby T helper cell activation (as indicted by CD69 expression of B220+ cells) showed a similar dose response curve for tPA-NS1, while other vectors showed no notable response.

Alignment of the sequences of peptide 87 (SEQ ID NO: 8—RTQMKGPWHSEELEI) and peptide 88 (SEQ ID NO: 9—MKGPWHSEELEIRFI) showed the conserved sequence MKGPWHSEELEI (SEQ ID NO: 3).

Alignment of the sequences of peptide 68 (SEQ ID NO: 10—SEKNDTWRLKRAHLI) and peptide 69 (SEQ ID NO:

11—NDTWRLKRAHLIEMK) showed the conserved sequence NDTWRLKRAHLI (SEQ ID NO: 2).

Example 3—Anti-NS1 Antibodies

To assess the specificity of the humoral immune response induced by tPA-NS1 vaccination, serum derived antibodies from vaccinated mice were isolated and assessed for their ability to bind to membrane bound NS1.
Antibodies from tPA-NS1 Vaccinated Mice Recognise Membrane Bound NS1

Vero cells were infected with $ZIKV_{PRVABC59}$ at MOI of 0.1 in order to express membrane bound NS1. To assess if antibodies from vaccinated mice would bind to this membrane bound NS1, serum was collected on day 42 from mice vaccinated with control pVax vector, tPA-NS1 vector, or vector containing tPA-NS1-IMX313P (heptamer), in accordance with the protocol set out in FIG. 5.

The serum was diluted 1 in 200, and then washed NS1 expressing Vero cells were resuspended in 100 µl of dilute serum (1/200), polyclonal rabbit anti-ZIKV NS1 antibody (GeneTex) or 4G2 mouse anti-flavivirus envelope antibody (Clonegene). After 60 minutes of incubation at 4° C., the cells were washed and resuspended with Alexa Fluor 488-labelled goat anti-mouse IgG (Invitrogen) secondary antibody for 60 minutes at 4° C. in the dark. Antibody binding was analysed by flow cytometry.

Figure 21:
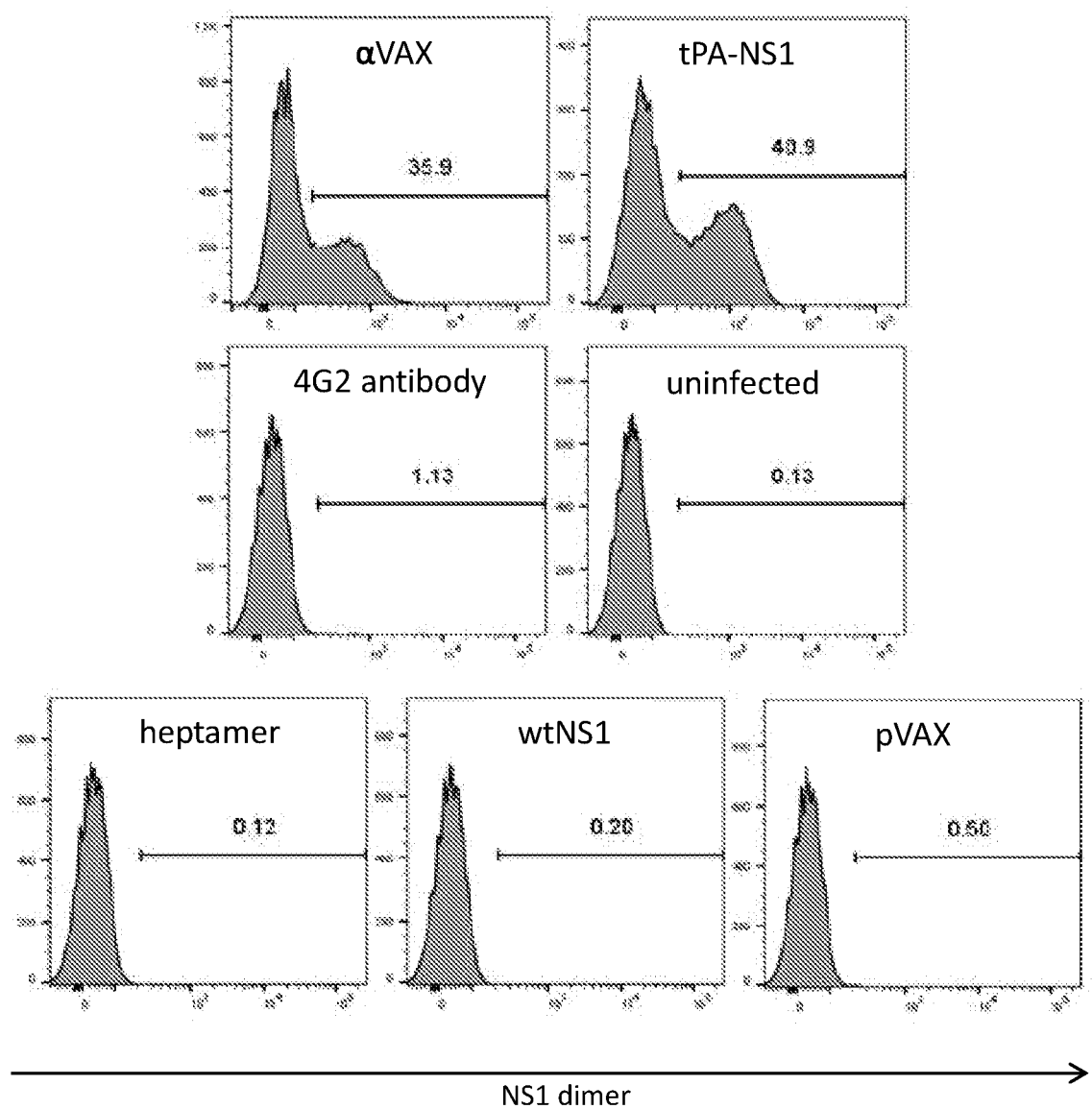

As can be seen in FIG. 21, only pooled sera from tPA-NS1 vaccinated mice bound to NS1 on ZIKV infected Vero cells at the similar frequency to that observed with the positive control (polyclonal rabbit anti-ZIKA NS1 commercial antibody—"αNS1"; mean=40.9% vs 35.9%, respectively). Sera from wtNS1 and tPA-NS1-IMX313P (heptamer) vaccinated mice failed to bind NS1 on infected Vero cells (0.2% and 0.12%, respectively). Further, sera from control empty pVAX ("pVAX") vaccinated mice failed to bind surface expressed NS1 (0.5%). The specificity of NS1 recognition by sera from tPA-NS1 vaccinated mice, was confirmed by the inability of sera to bind to uninfected Vero cells. Consequently, this indicates that serum from tPA-NS1 vaccinated mice binds to the NS1 dimer expressed on the cells infected with Zika, indicating the possibility that these antibodies might induce antibody dependent cell-mediated cytotoxicity (ADCC).

Example 4—T-Cell Response are Essential for NS1 Immunization

Vaccination and Survival Rates

To test if the tPA-NS1 DNA vaccine was effective in preventing Zika virus infection, a mouse model of Zika infection was employed. Mice were vaccinated as set out in FIG. 5 with either 50 µg of tPA-NS1, 100 µg of tPA-NS1, or 100 µg of control (pVax) DNA vaccine. On day 49 mice were infected with Zika via i.v. administration of 200 Plate Forming Units (PFU) of virus. While blood samples were isolated on weeks 2, 4 and 7 and analysed for anti-NS1 antibody titres.

Figure 22:
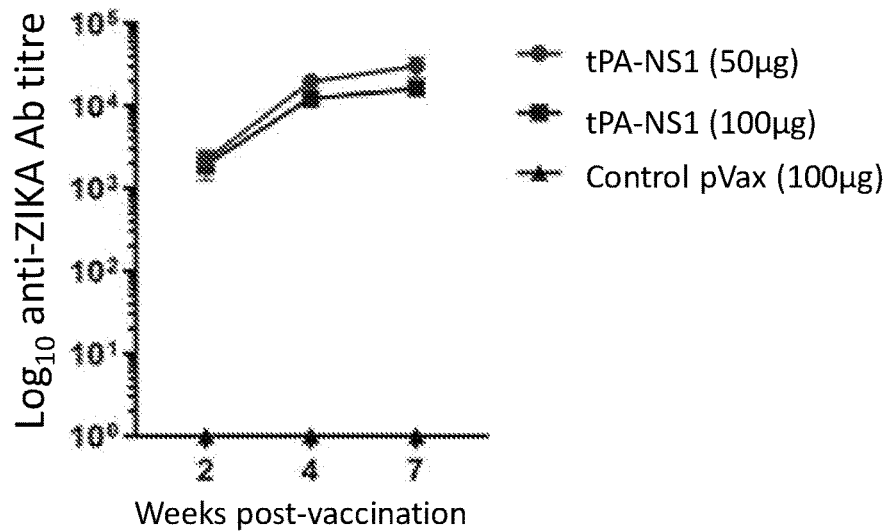

As can be seen in FIG. 22, both 50 µg and 100 µg of tPA-NS1 induced a comparable antibody titre, while pVax alone (control) failed to induce antibodies.

In murine models, Zika virus typically demonstrates an active infection for 7 days, with the infection peaking at day 3. Blood was collected from infected mice at day 1, day 3 and day 7 post infection and the viral loads were assessed using real-time (RT) quantitative PCR as previously described (Larocca R. A. et al. Nature. 2016, 536: 474-478).

Briefly, RNA was extracted from plasma with QIAcube HT (Qiagen, Germany). The wildtype ZIKV BeH815744 Cap gene was utilized as a standard. RNA was purified (Zymo Research), and RNA quality and concentration were assessed by the BIDMC Molecular Core Facility. Log dilutions of the RNA standard were reverse transcribed and included with each RT-PCR assay. Viral loads were calculated as virus particles (VP) per ml.

Figure 23:
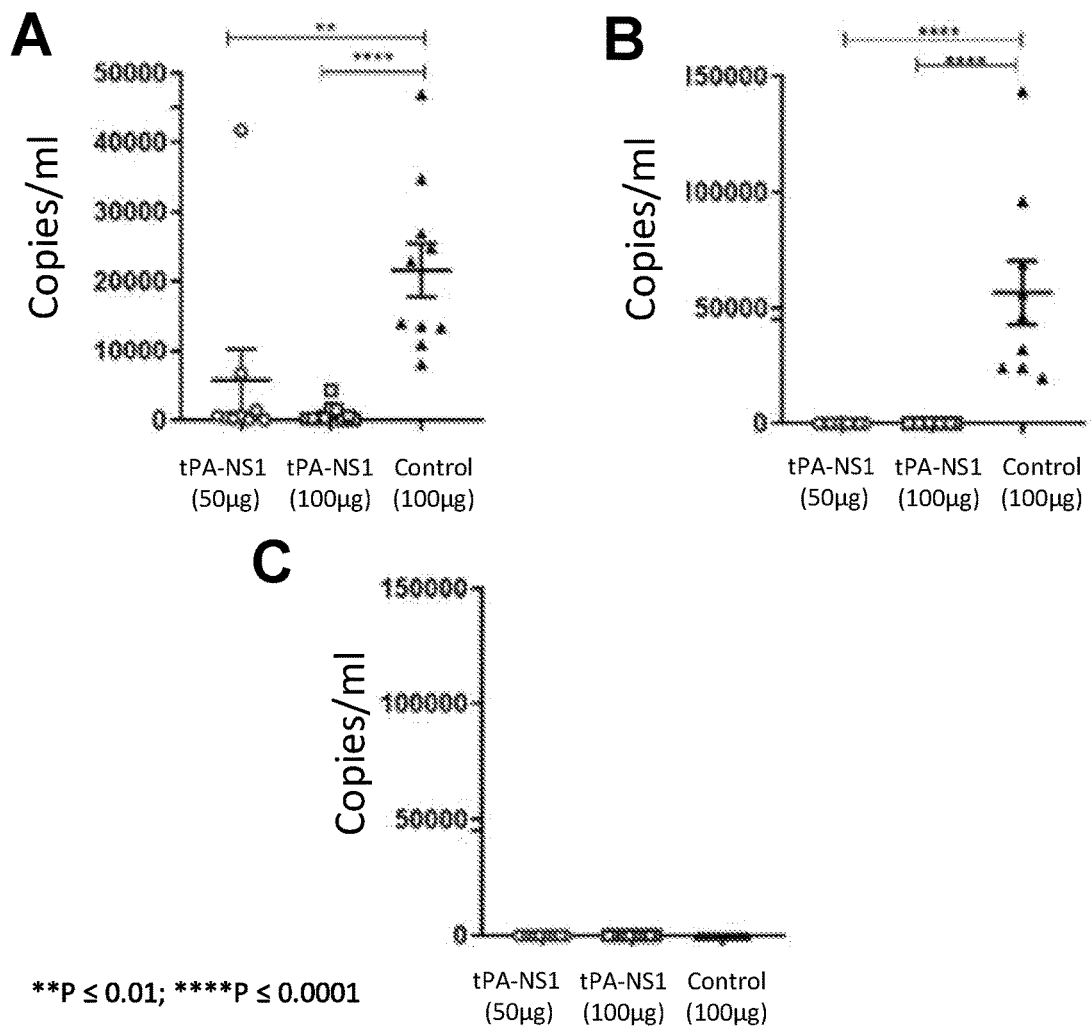

As can be seen in FIG. 23A, mice administered with either 50 µg or 100 µg of tPA-NS1 had a statistically significantly lower viral load on day 1 than mice administered control (pVax) DNA vectors, with only one mouse in the 50 µg treatment group showing a notable infection. By day 3 (FIG. 23B), all mice treated with the tPA-NS1 DNA vector showed little to no notable viral load, while the mean viral load in control treated mice had increased from approximately 21,000 copies/ml on day 1 to approximately 60,000 copies/ml. At day 7 (FIG. 23C), the viral infection was largely resolved in mice with all three groups showing no detectable levels of Zika virus. As such, it appears that NS1 can be the basis of an effected DNA vaccine, but only when linked to a heterologous signal sequence which result in secretion of the NS1 protein, such as the tPA signal sequence (see FIG. 28).
Passive Transfer of Anti-NS1 Antibody is Insufficient to Elicit Immunity The immune system is multifactorial and has a large degree of redundancy. Consequently, there is a poor understanding of correlates that are predictive of protection (immunity) following vaccination. However, the efficacy of vaccination in a variety of infections is not correlated with antibody titre, nor is protection effected by antibodies in a range of immunisations.

With specific regard to Zika viral infections, antibodies specific for the envelope proteins, the pre-membrane protein and NS1 have been identified in patients after infection with Zika virus. However, only antibodies targeting the envelope proteins exhibit significant neutralizing activity (Kudchodkar, S. B. et al., Microbes infect., 2018, 20: 676-684). Consequently, despite the evidence that tPA-NS1 DNA vaccine induces NS1-specific antibodies in mice, whether this correlates, and is sufficient for, protection to Zika could not be concluded.

Therefore, the ability of anti-NS1 antibodies to confer protection was evaluated in a mouse model of passive antibody transfer.

Figure 24:
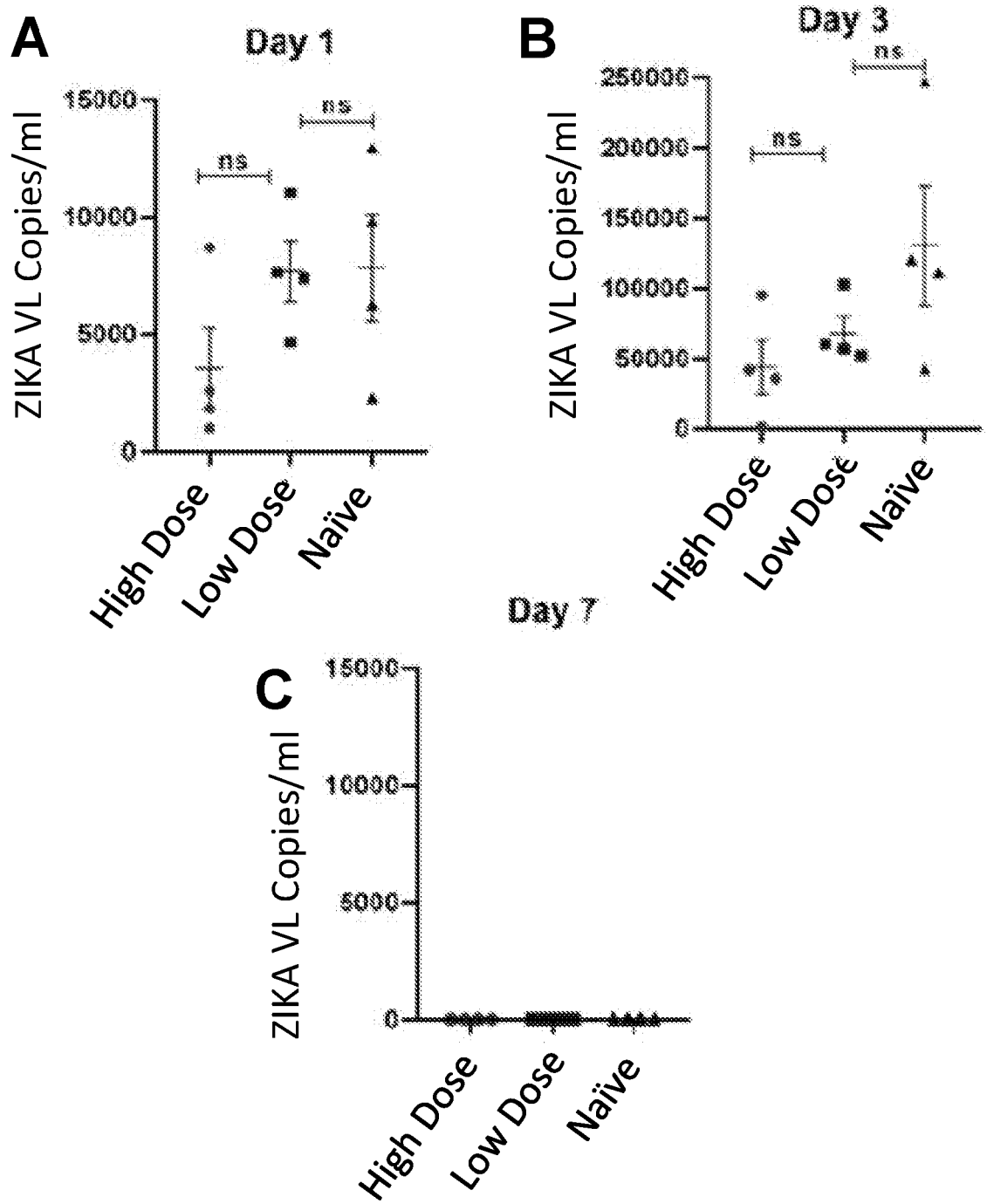

Serum was collected from mice vaccinated with tPA-NS1 DNA and polyclonal IgG was purified using protein G purification kits (Thermo Fisher Scientific). For control, polyclonal serum IgG was purified from naïve (non-immunized) mice. Varying amounts of purified IgG was infused by the i.v. route into naïve recipient mice (n=4 per group) resulting in a final concentration of 2.9 $\log_{10}$ anti-NS1 antibody titre ("high dose") and 2.2 $\log_{10}$ anti-NS1 antibody titre ("Low Dose"), before ZIKV challenge. A comparable dose of IgG from naïve mice was administered to a third, control, group. Mice were subsequently challenged with 200 PFUs of $ZIKA_{ZKV2015}$ and the viral loads were analysed on day 1 (FIG. 24A), day 3 (FIG. 24B) and day 7 (FIG. 24C) post-viral challenge by real-time quantitative PCR, as set out above. All animals were viremic with no statistically significant differences between groups (FIGS. 24A and 24B) irrespective of status of passive transfer of anti-NS1 antibodies. While the infection resolved by day 7 (FIG. 24C) as previously shown (see FIG. 23C). Further, in comparison to FIG. 23, the elevated viral loads, is the mice administered with anti-NS1 antibody, indicates that an antibody response alone is insufficient to provide protection and that antibodies alone are not an appropriate correlate for protection from Zika virus infection.

T-Cell Response is Necessary for Protection from ZIKA Virus Infection

To assess the role of the cell mediated immune response (primarily T cells) in protection against ZIKA virus infection following DNA vaccination, interferon alpha/beta receptor deficient (IFNAR−/−) mice on a Balb/c background (n=6) and wild-type Balb/c mice (n=7) were vaccinated with 50 μg of tPA-NS1 DNA vaccine using the vaccination protocol set out in FIG. 5. Blood was collected at weeks 2, 4 and 7 and ZIKA NS1 antibody titres were analysed using ELISA as set out above in Example 1.

Figure 25:
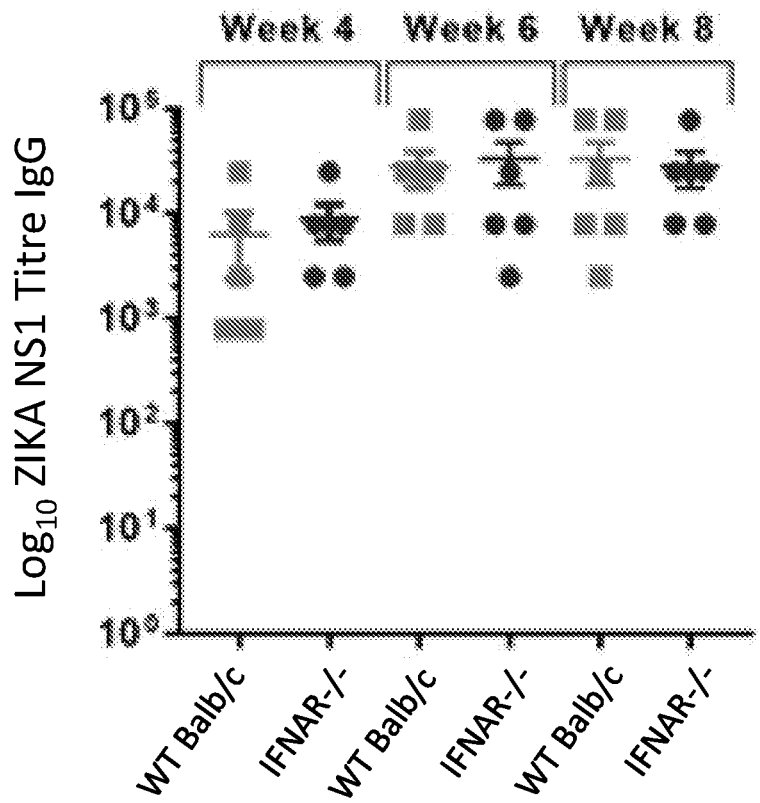

As can be seen in FIG. 25, there were no significant differences in the anti-NS1 Ab titers induced by tPA-NS1 vaccination of IFNAR−/− mice compared to wild-type Balb/c mice. Consequently, IFN signalling, and T cells response, is not needed for induction of an antibody response To assess if the induced antibody response in IFNRA−/− mice was sufficient to confer protection from ZIKA virus in the absence of a T cell response, IFNAR−/− mice were subcutaneously challenged with a lethal dose ($10^3$ culture infection dose 50%) of ZIKA ($MR_{766}$ strain) at week 7 using the protocol set forth in Abbink P. et al. Science, 2016, 353:1129-32. It is known that IFN α/β signalling plays a key role in priming adaptive T-cell responses and directly influences the fate of both CD4+ and CD8+ T cells during initial antigen presentation, with this shaping the effector and memory T-cell pool (Huber J. P. and Farrar J. D. Immunology, 2011, 132:466-74). Therefore, the absence of IFN α/β signalling results in a dysfunctional T cell response in the vaccinated IFNAR−/− mice, ablating T cell mediated protection.

Figure 26:
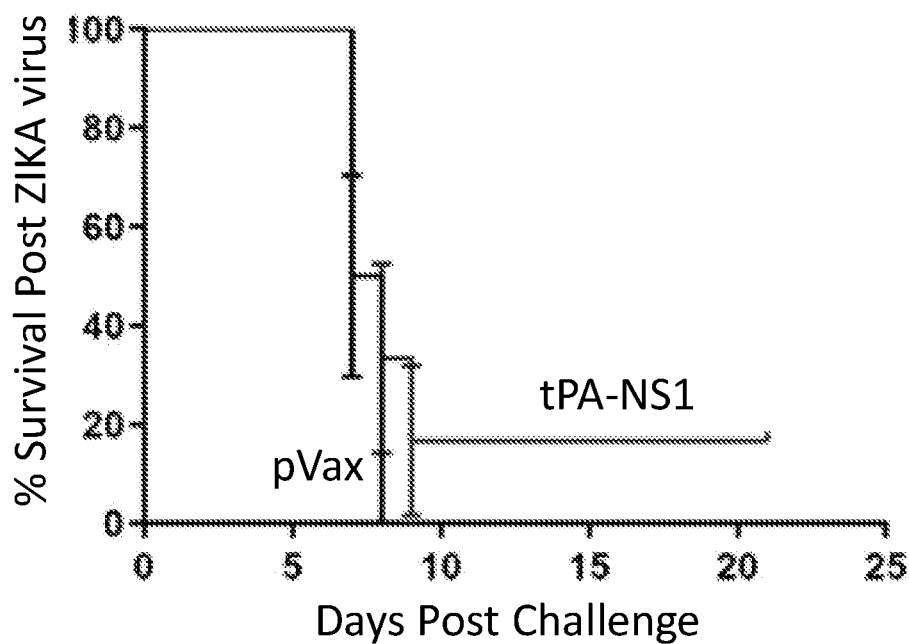

FIG. 26 shows that following ZIKA virus challenge in the absence of a T cell response, the elevation in anti-NS1 antibodies in response to tPA-NS1 vaccination was insufficient to confer protection form ZIKA virus challenge with all but 1 mice succumbing to infection by day 9. This was not significantly different to IFNAR deficient (−/−) mice vaccinated with the empty pVax vector control. This illustrates that in the absence of IFN α/β signalling, the presence of high anti-NS1 antibody titres (FIG. 25) was not sufficient to confer protection and illustrates that anti-NS1 titres are not solely predictive of a protective immune response.

Depletion of T Cells Reduces Protection to ZIKA Virus Infection

To further analyse the role of T cells in NS1 DNA vaccine induced protection against Zika virus infection, CD8+ and/or CD4+ T cells were depleted from Balb/c mice.

To deplete T cells, anti-CD4 (GK1.5) and/or anti-CD8 beta (Lyt3.2 clone 539 53-5.8) (Bio X Cell) monoclonal antibodies were administered at doses of 0.1 mg per mouse (n=10) to tPA-NS1 DNA vaccinated mice via i.p. injection 2 days prior to ZIKA virus challenge. Empty pVax vectors were used for a control. To confirm that CD4+ T cell depletion was maintained through the acute phase of infection, splenocytes were collected and analysed on days 2 and 5 post-treatment. Antibody depletions were >99.9% efficient as determined by flow cytometry (data not shown) using the detection antibodies α-CD4-APC-Cy7 (clone 544 RM4-5), α-CD8-PerCP-Cy 5.5 (clone 53-6.7), α-CD3-AF700 (clone 500A2).

Figure 27:
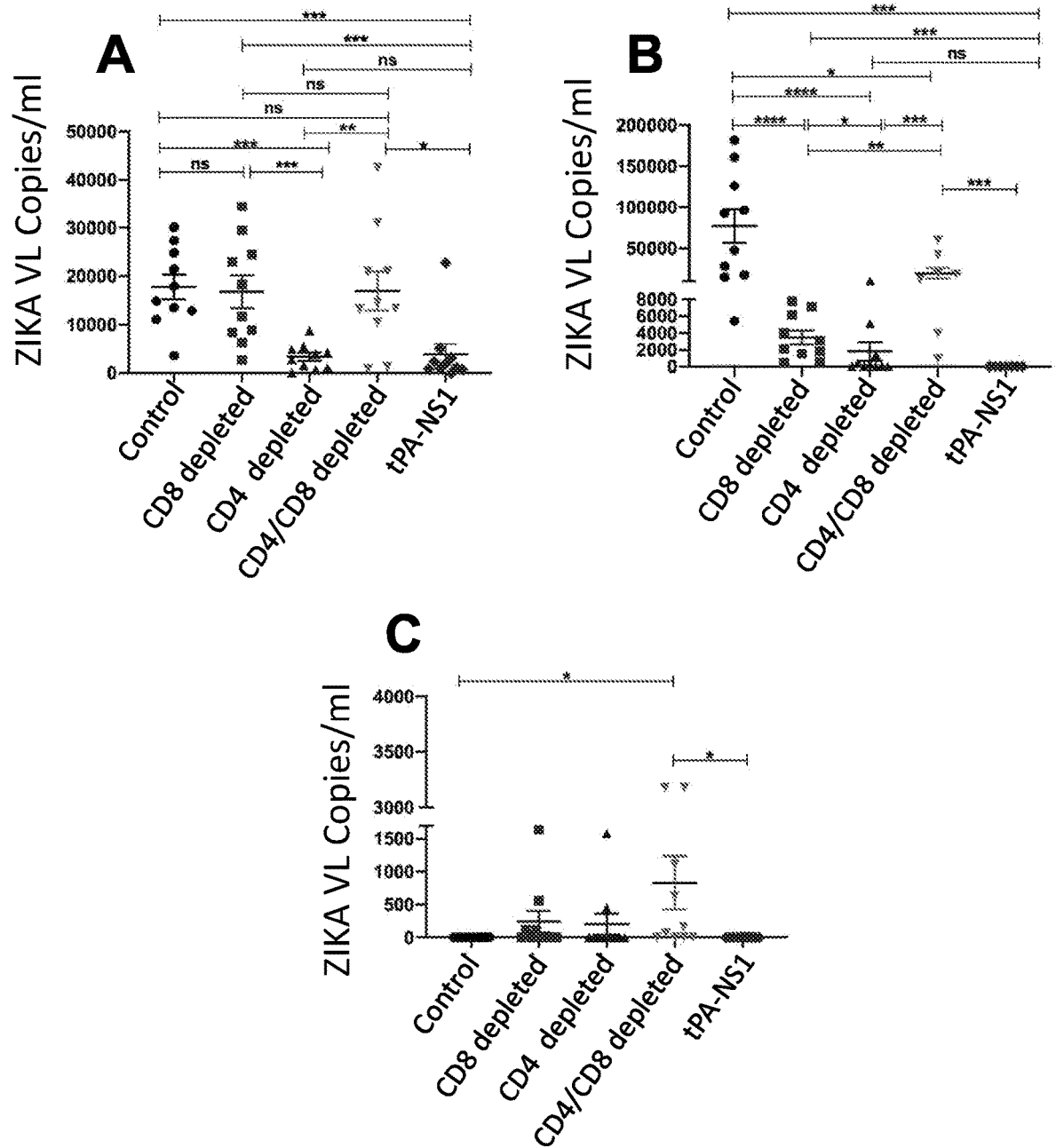

As shown in FIG. 27, depletion of CD8+ T-cells completely abrogated viral control on Day 1 (FIG. 27A) post-challenge, while CD4+ T cell-depleted mice had significantly lower viral loads than control (pVax) or CD8+ depleted mice (***p<0.001) and comparable viral loads on day 1 to tPA-NS1 vaccinated mice. Additionally, mice depleted of both CD8+ and CD4+ T cells were unable to control ZIKV infection on Day 1 (FIG. 27A) indicating an important role for NS1 specific CD8+ T cells in the early control of ZIKV infection after immunisation with tPA-NS1.

By day 3 (FIG. 27B), T cell depleted groups showed varying degrees of viral control when compared to pVAX control. CD8+ T cell depleted mice remained viraemic with a significantly higher viral load than CD4+ T cell depleted mice (*p<0.05), again indicating the need for a sustained CD8+ T cell response in the control of ZIKV infection. This was further confirmed as CD8+/CD4+ T cell depleted mice had a significantly higher viral load than CD8+(p=0.001) or CD4+-depleted mice (*p<0.0001), suggesting that CTL and T helper cell responses are important to protect from ZIKV virus. At day 7 (FIG. 27C), only 20% of CD4+ depleted mice remained viraemic whereas 50% of CD8+ and CD4+/CD8+-depleted animals had a detectable ZIKA viral load compared to control pVAX, while all control mice had resolved the infection.

The above data indicate that T cell-mediated immunity, rather than anti-NS1 antibodies, are crucial for the protection and elimination of ZIKV infection following tPA-NS1 DNA vaccine administration. Consequently, antibody response to NS1 vaccination is not sufficient to predict functional protection to ZIKA virus infection. Rather, it is critical that a T cell response is induced in response to vaccination.

Confirmation of NS1 Secretion

To confirm that the NS1 linked to the heterologous signal peptide (tPA) was secreted from mammalian cells, a western-blot of transfected cells was performed as set out below.

Cell lysates and supernatant fluids were harvested from HEK293T cells 433 transiently transfected (48h) with NS1 DNA vaccines described above, using Lipofectamine LTX reagent (Life Technologies). Fifty μg of protein was analysed in 10-12% (v/v) SDS-PAGE under reducing (with β-mercaptoethanol, β-Me) or non-reducing (without β-Me) conditions as described in Tomusange K, et al. Sci Rep. 2016, 834(6) pp. 29131. Mouse monoclonal anti-NS1 antibody (Biofront) and goat anti-mouse IgG-HRP conjugated secondary antibody (Invitrogen) were used to detect NS1 expression as described previously in Tomusange (see above).

Figure 28:
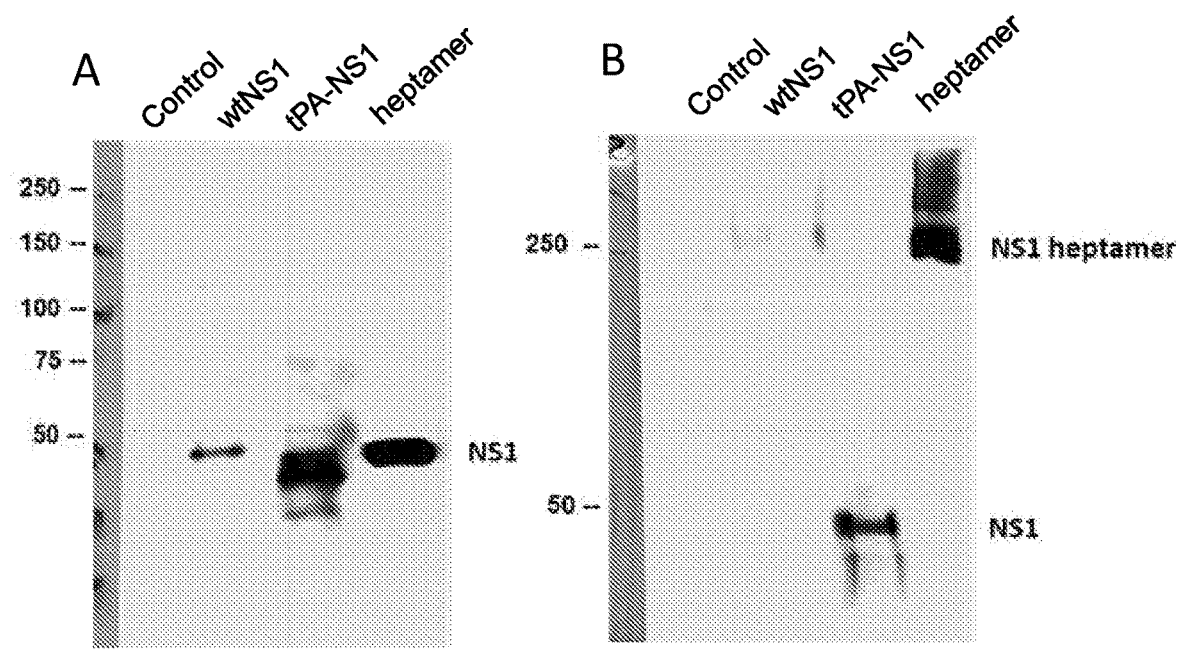

As can be seen in FIG. 28-A NS1 protein is present in cell lysates from HEK293T cell when transfected with wtNS1, tPA-NS1 or heptamer expressing DNA vectors. However, as can be seen in FIG. 28-B, only cell supernatants from cells transfected with tPA-NS1 or heptamer expressing DNA vectors contained NS1 protein confirming that wtNS1 (which lacked the tPA signal peptide) was not secreted from the mammalian cell line.

All methods described herein can be performed in any suitable order unless indicated otherwise herein or clearly contradicted by context. The use of any and all examples, or exemplary language (e.g., "such as") provided herein, is intended merely to better illuminate the example embodiments and does not pose a limitation on the scope of the claimed invention unless otherwise claimed. No language in the specification should be construed as indicating any non-claimed element as essential.

The description provided herein is in relation to several embodiments which may share common characteristics and features. It is to be understood that one or more features of one embodiment may be combinable with one or more features of the other embodiments. In addition, a single feature or combination of features of the embodiments may constitute additional embodiments.

Those skilled in the art will appreciate that the invention described herein is susceptible to variations and modifications other than those specifically described. It is to be understood that the invention includes all such variations and modifications. The invention also includes all of the steps, features, compositions and compounds referred to, or indicated in this specification, individually or collectively, and any and all combinations of any two or more of the steps or features.

The subject headings used herein are included only for the ease of reference of the reader and should not be used to limit the subject matter found throughout the disclosure or the claims. The subject headings should not be used in construing the scope of the claims or the claim limitations.

Also, it is to be noted that, as used herein, the singular forms "a", "an" and "the" include plural aspects unless the context already dictates otherwise.

Future patent applications may be filed on the basis of or claiming priority from the present application.

The invention claimed is:

1. A pharmaceutical composition including:
 a nucleic acid molecule including a sequence having at least 90% sequence identity to the sequence set forth in SEQ ID NO: 4 and encoding an immunogenic peptide comprising a portion of the non-structural protein 1 (NS1 protein) of Zika virus, the nucleic acid encoding a heterologous signal peptide operatively linked to the immunogenic peptide,
 wherein the immunogenic peptide, when expressed, is secreted from a mammalian cell, and wherein the pharmaceutical composition induces an immune response when administered to a mammal.

2. A pharmaceutical composition according to claim 1, wherein the immunogenic peptide has at least 90% sequence identity to a portion of the Zika virus NS1 protein sequence set forth in SEQ ID NO: 1.

3. A pharmaceutical composition according to claim 1, wherein the immunogenic peptide elicits one or more of a T-helper response, a cytotoxic-T-cell response and a B-cell response.

4. A pharmaceutical composition according to claim 1, wherein the immunogenic peptide has at least 90% sequence identity to a portion of the NS1 protein located from position 172 to 352, or from position 172 to 278, or from position 204 to 278, or from position 204 to 352, or from position 204 to 218, or from position 204 to 221, or from positions 207 to 218, or from position 207 to 221, or from position 261 to 275, or from position 261 to 278, or from positions 264 to 275, or from position 264 to 278 of SEQ ID NO: 1.

5. A pharmaceutical composition according to claim 1, wherein the immunogenic peptide has at least 90%, at least 95%, at least 98%, at least 99% or 100% sequence identity to a portion of the non-structural protein 1 (NS1 protein) of Zika virus, across the length of the immunogenic peptide.

6. A pharmaceutical composition according to claim 1, wherein the nucleic acid molecule includes the sequence set forth in SEQ ID NO: 4.

7. A pharmaceutical composition according to claim 1, wherein the heterologous signal peptide directs secretion of the immunogenic peptide from a mammalian cell.

8. A pharmaceutical composition according to claim 1, wherein the heterologous signal peptide is a tissue plasminogen activator (tPA) signal peptide.

9. A pharmaceutical composition according to claim 1, wherein the heterologous signal peptide is not an immunoglobulin (Ig) signalling peptide, or is not an IgE signalling peptide.

10. A pharmaceutical composition according to claim 1, wherein the heterologous signal peptide has 80%, 85%, 90%, 95% or 100% sequence identity to the sequences set forth in SEQ ID NO: 5 or SEQ ID NO: 12.

11. A pharmaceutical composition according to claim 1, wherein the nucleic acid molecule includes a sequence which has at least 80%, 85%, 90%, 95%, 98%, 99% or 100% sequence identity to the sequence set forth in SEQ ID NO: 6.

12. A pharmaceutical composition according to claim 1, wherein the nucleic acid molecule includes a promoter which is a constitutive promoter in a mammalian cell.

13. A pharmaceutical composition according to claim 12, wherein the promoter is a CMV promoter.

14. A pharmaceutical composition according to claim 1, wherein the pharmaceutical composition includes:
 a DNA vector including the nucleic acid molecule encoding the immunogenic peptide and the operatively linked heterologous signal peptide: or
 a viral vector including the nucleic acid molecule encoding the immunogenic peptide and the operatively linked heterologous signal peptide.

15. A pharmaceutical composition according to claim 14, wherein the DNA vector is the pVax 1 vector.

16. A method of eliciting an immune response in a subject, the method including the step of:
 administering to the subject an immunogenic agent, wherein the immunogenic agent is a pharmaceutical composition according to claim 1.

17. A method of eliciting an immune response in a subject according to claim 16, wherein the immune response is a T cell response.

18. A method of reducing viral titer in a subject with a Zika virus infection, the method including a step of prophylactically administering to the subject a pharmaceutical composition according to claim 1.

19. A pharmaceutical composition according to claim 1, wherein the nucleic acid is RNA.

* * * * *

SEQUENCE LISTING

```
<160> NUMBER OF SEQ ID NOS: 131

<210> SEQ ID NO 1
<211> LENGTH: 352
<212> TYPE: PRT
<213> ORGANISM: Zika Virus

<400> SEQUENCE: 1

Asp Val Gly Cys Ser Val Asp Phe Ser Lys Lys Glu Thr Arg Cys Gly
1               5                   10                  15

Thr Gly Val Phe Val Tyr Asn Asp Val Glu Ala Trp Arg Asp Arg Tyr
            20                  25                  30

Lys Tyr His Pro Asp Ser Pro Arg Arg Leu Ala Ala Ala Val Lys Gln
        35                  40                  45

Ala Trp Glu Asp Gly Ile Cys Gly Ile Ser Ser Val Ser Arg Met Glu
    50                  55                  60

Asn Ile Met Trp Arg Ser Val Glu Gly Glu Leu Asn Ala Ile Leu Glu
65                  70                  75                  80

Glu Asn Gly Val Gln Leu Thr Val Val Gly Ser Val Lys Asn Pro
                85                  90                  95

Met Trp Arg Gly Pro Gln Arg Leu Pro Val Pro Val Asn Glu Leu Pro
            100                 105                 110

His Gly Trp Lys Ala Trp Gly Lys Ser Tyr Phe Val Arg Ala Ala Lys
        115                 120                 125

Thr Asn Asn Ser Phe Val Val Asp Gly Asp Thr Leu Lys Glu Cys Pro
    130                 135                 140

Leu Lys His Arg Ala Trp Asn Ser Phe Leu Val Glu Asp His Gly Phe
145                 150                 155                 160

Gly Val Phe His Thr Ser Val Trp Leu Lys Val Arg Glu Asp Tyr Ser
                165                 170                 175

Leu Glu Cys Asp Pro Ala Val Ile Gly Thr Ala Val Lys Gly Lys Glu
            180                 185                 190

Ala Val His Ser Asp Leu Gly Tyr Trp Ile Glu Ser Glu Lys Asn Asp
        195                 200                 205

Thr Trp Arg Leu Lys Arg Ala His Leu Ile Glu Met Lys Thr Cys Glu
    210                 215                 220

Trp Pro Lys Ser His Thr Leu Trp Thr Asp Gly Ile Glu Glu Ser Asp
225                 230                 235                 240

Leu Ile Ile Pro Lys Ser Leu Ala Gly Pro Leu Ser His His Asn Thr
                245                 250                 255

Arg Glu Gly Tyr Arg Thr Gln Met Lys Gly Pro Trp His Ser Glu Glu
            260                 265                 270

Leu Glu Ile Arg Phe Glu Glu Cys Pro Gly Thr Lys Val His Val Glu
        275                 280                 285

Glu Thr Cys Gly Thr Arg Gly Pro Ser Leu Arg Ser Thr Thr Ala Ser
```

```
                290               295               300
Gly Arg Val Ile Glu Glu Trp Cys Cys Arg Glu Cys Thr Met Pro Pro
305                 310                 315                 320

Leu Ser Phe Arg Ala Lys Asp Gly Cys Trp Tyr Gly Met Glu Ile Arg
                325                 330                 335

Pro Arg Lys Glu Pro Glu Ser Asn Leu Val Arg Ser Met Val Thr Ala
            340                 345                 350

<210> SEQ ID NO 2
<211> LENGTH: 12
<212> TYPE: PRT
<213> ORGANISM: Zika Virus

<400> SEQUENCE: 2

Asn Asp Thr Trp Arg Leu Lys Arg Ala His Leu Ile
1               5                   10

<210> SEQ ID NO 3
<211> LENGTH: 12
<212> TYPE: PRT
<213> ORGANISM: Zika Virus

<400> SEQUENCE: 3

Met Lys Gly Pro Trp His Ser Glu Glu Leu Glu Ile
1               5                   10

<210> SEQ ID NO 4
<211> LENGTH: 1053
<212> TYPE: DNA
<213> ORGANISM: Artificial Sequence
<220> FEATURE:
<223> OTHER INFORMATION: Codon Optimised

<400> SEQUENCE: 4
gatgtgggct gcagcgtgga cttcagcaag aaagaaacca gatgcggcac cggcgtgttc      60
gtgtacaacg atgtcgaggc ctggcgggac agatacaagt atcaccctga cagccccaga     120
cggctggccg ctgctgtgaa acaggcttgg gaggatggca tctgcggcat cagcagcgtg     180
tcccggatgg aaaacatcat gtggcggagc gtggaaggca gctgaacgc catcctggaa     240
gagaatggcg tgcagctgac agtggtcgtg ggcagcgtga agaaccctat gtggcgagga     300
cctcagagac tgcccgtgcc tgtgaatgaa ctgcctcacg gatggaaggc ctggggcaag     360
agctattttg tgcgggctgc caagaccaac aacagcttcg tggtggacgg cgacaccctg     420
aaagagtgcc ctctgaaaca cagagcctgg aatagcttcc tggtcgagga tcacggcttt     480
ggcgtgttcc acacaagcgt gtggctgaaa gtgcgcgagg actactccct ggaatgcgac     540
cctgccgtga ttggcacagc cgtgaaggga aagaagccg tgcacagcga tctcggctac     600
tggatcgaga gcgagaagaa cgatacctgg cggctgaaga gagcccacct gatcgagatg     660
aagacctgcg agtggcccaa gagccacaca ctgtggaccg atggcatcga ggaaagcgac     720
ctgatcatcc ctaagagcct ggccggacct ctgagccacc acaataccag agagggctac     780
agaacccaga tgaagggccc atggcacagc gaggaactgg aaatcagatt cgaggaatgc     840
cccggcacca aggtgcacgt ggaagagaca tgtggcacaa gaggccccag cctgagaagc     900
acaacagcct ctggcagagt gatcgaagag tggtgctgcc gcgagtgcac aatgcctcca     960
ctgagcttca gagccaagga cggctgttgg tacggcatgg aaatccggcc tagaaaagag    1020
cccgagagca acctcgtgcg gagcatggtt aca                                 1053
```

<210> SEQ ID NO 5
<211> LENGTH: 23
<212> TYPE: PRT
<213> ORGANISM: Homo sapiens

<400> SEQUENCE: 5

Met Asp Ala Met Lys Arg Gly Leu Cys Cys Val Leu Leu Leu Cys Gly
1               5                   10                  15

Ala Val Phe Val Ser Ala Ser
            20

<210> SEQ ID NO 6
<211> LENGTH: 69
<212> TYPE: DNA
<213> ORGANISM: Artificial Sequence
<220> FEATURE:
<223> OTHER INFORMATION: Codon optimised

<400> SEQUENCE: 6
atggatgcaa tgaagagagg gctctgctgt gtgctgctgc tgtgtggagc agtcttcgtt      60
tcggctagc                                                             69

<210> SEQ ID NO 7
<211> LENGTH: 1122
<212> TYPE: DNA
<213> ORGANISM: Artificial Sequence
<220> FEATURE:
<223> OTHER INFORMATION: Codon optimised

<400> SEQUENCE: 7
atggatgcaa tgaagagagg gctctgctgt gtgctgctgc tgtgtggagc agtcttcgtt      60
tcggctagcg atgtgggctg cagcgtggac ttcagcaaga agaaaccag atgcggcacc      120 ggcgtgttcg tgtacaacga tgtcgaggcc tggcgggaca gatacaagta tcaccctgac      180
agccccagac ggctggccgc tgctgtgaaa caggcttggg aggatggcat ctgcggcatc      240
agcagcgtgt cccggatgga aaacatcatg tggcggagcg tggaaggcga gctgaacgcc      300
atcctggaag agaatggcgt gcagctgaca gtggtcgtgg cagcgtgaa gaaccctatg      360 tggcgaggac ctcagagact gcccgtgcct gtgaatgaac tgcctcacgg atggaaggcc      420
tggggcaaga gctattttgt gcgggctgcc aagaccaaca acagcttcgt ggtggacggc      480
gacaccctga agagtgccc tctgaaacac agagcctgga atagcttcct ggtcgaggat      540
cacggctttg gcgtgttcca cacaagcgtg tggctgaaag tgcgcgagga ctactccctg      600
gaatgcgacc ctgccgtgat tggcacagcc gtgaagggaa agaagccgt gcacagcgat      660 ctcggctact ggatcgagag cgagaagaac gatacctggc ggctgaagag agcccacctg      720
atcgagatga gacctgcga gtggcccaag agccacacac tgtggaccga tggcatcgag      780
gaaagcgacc tgatcatccc taagagcctg gccggacctc tgagccacca caataccaga      840
gagggctaca gaacccagat gaagggccca tggcacagca ggaactgga atcagattc      900 gaggaatgcc ccggcaccaa ggtgcacgtg aagagacat gtggcacaag aggccccagc      960
ctgagaagca aacagcctc tggcagagtg atcgaagagt ggtgctgccg cgagtgcaca      1020
atgcctccac tgagcttcag agccaaggac ggctgttggt acggcatgga aatccggcct      1080
agaaaagagc ccgagagcaa cctcgtgcgg agcatggtta ca                        1122

<210> SEQ ID NO 8
<211> LENGTH: 15

```
<212> TYPE: PRT
<213> ORGANISM: Zika Virus

<400> SEQUENCE: 8

Arg Thr Gln Met Lys Gly Pro Trp His Ser Glu Glu Leu Gl

```
                         85                  90                  95
Met Trp Arg Gly Pro Gln Arg Leu Pro Val Pro Val Asn Glu Leu Pro
                100                 105                 110

His Gly Trp Lys Ala Trp Gly Lys Ser Tyr Phe Val Arg Ala Ala Lys
            115                 120                 125

Thr Asn Asn Ser Phe Val Val Asp Gly Asp Thr Leu Lys Glu Cys Pro
        130                 135                 140

Leu Glu His Arg Ala Trp Asn Ser Phe Leu Val Glu Asp His Gly Phe
145                 150                 155                 160

Gly Val Phe His Thr Ser Val Trp Leu Lys Val Arg Glu Asp Tyr Ser
                165                 170                 175

Leu Glu Cys Asp Pro Ala Val Ile Gly Thr Ala Val Lys Gly Arg Glu
            180                 185                 190

Ala Ala His Ser Asp Leu Gly Tyr Trp Ile Glu Ser Glu Lys Asn Asp
        195                 200                 205

Thr Trp Arg Leu Lys Arg Ala His Leu Ile Glu Met Lys Thr Cys Glu
    210                 215                 220

Trp Pro Lys Ser His Thr Leu Trp Thr Asp Gly Val Glu Glu Ser Asp
225                 230                 235                 240

Leu Ile Ile Pro Lys Ser Leu Ala Gly Pro Leu Ser His His Asn Thr
                245                 250                 255

Arg Glu Gly Tyr Arg Thr Gln Val Lys Gly Pro Trp His Ser Glu Glu
            260                 265                 270

Leu Glu Ile Arg Phe Glu Glu Cys Pro Gly Thr Lys Val Tyr Val Glu
        275                 280                 285

Glu Thr Cys Gly Thr Arg Gly Pro Ser Leu Arg Ser Thr Thr Ala Ser
    290                 295                 300

Gly Arg Val Ile Glu Glu Trp Cys Cys Arg Glu Cys Thr Met Pro Pro
305                 310                 315                 320

Leu Ser Phe Arg Ala Lys Asp Gly Cys Trp Tyr Gly Met Glu Ile Arg
                325                 330                 335

Pro Arg Lys Glu Pro Glu Ser Asn Leu Val Arg Ser Met Val Thr Ala
            340                 345                 350

<210> SEQ ID NO 14
<211> LENGTH: 352
<212> TYPE: PRT
<213> ORGANISM: Zika Virus

<400> SEQUENCE: 14

Asp Val Gly Cys Ser Val Asp Phe Ser Lys Lys Glu Thr Arg Cys Gly
1               5                   10                  15

Thr Gly Val Phe Val Tyr Asn Asp Val Glu Ala Trp Arg Asp Arg Tyr
            20                  25                  30

Lys Tyr His Pro Asp Ser Pro Arg Arg Leu Ala Ala Ala Val Lys Gln
        35                  40                  45

Ala Trp Glu Asp Gly Ile Cys Gly Ile Ser Ser Val Ser Arg Met Glu
    50                  55                  60

Asn Ile Met Trp Arg Ser Val Glu Gly Glu Leu Asn Ala Ile Leu Glu
65                  70                  75                  80

Glu Asn Gly Val Gln Leu Thr Val Val Gly Ser Val Lys Asn Pro
                85                  90                  95

Met Trp Arg Gly Pro Gln Arg Leu Pro Val Pro Val Asn Glu Leu Pro
                100                 105                 110
```

-continued

His Gly Trp Lys Ala Trp Gly Lys Ser Tyr Phe Val Arg Ala Ala Lys
            115                 120                 125

Thr Asn Asn Ser Phe Val Val Asp Gly Asp Thr Leu Lys Glu Cys Pro
        130                 135                 140

Leu Lys His Arg Ala Trp Asn Ser Phe Leu Val Glu Asp His Gly Phe
145                 150                 155                 160

Gly Ile Phe His Thr Ser Val Trp Leu Lys Val Arg Glu Asp Tyr Ser
                165                 170                 175

Leu Glu Cys Asp Pro Ala Val Ile Gly Thr Ala Val Lys Gly Lys Glu
            180                 185                 190

Ala Val His Ser Asp Leu Gly Tyr Trp Ile Glu Ser Glu Lys Asn Asp
        195                 200                 205

Thr Trp Arg Leu Lys Arg Ala His Leu Ile Glu Met Lys Thr Cys Glu
210                 215                 220

Trp Pro Lys Ser His Thr Leu Trp Thr Asp Gly Ile Glu Glu Ser Asp
225                 230                 235                 240

Leu Ile Ile Pro Lys Ser Leu Ala Gly Pro Leu Ser His His Asn Thr
                245                 250                 255

Arg Glu Gly Tyr Arg Thr Gln Met Lys Gly Pro Trp His Ser Glu Glu
            260                 265                 270

Leu Glu Ile Arg Phe Glu Glu Cys Pro Gly Thr Lys Val His Val Glu
        275                 280                 285

Glu Thr Cys Gly Thr Arg Gly Pro Ser Leu Arg Ser Thr Thr Ala Ser
            290                 295                 300

Gly Arg Val Ile Glu Glu Trp Cys Cys Arg Glu Cys Thr Met Pro Pro
305                 310                 315                 320

Leu Ser Phe Arg Ala Lys Asp Gly Cys Trp Tyr Gly Met Glu Ile Arg
                325                 330                 335

Pro Arg Lys Glu Pro Glu Ser Asn Leu Val Arg Ser Met Val Thr Ala
            340                 345                 350

<210> SEQ ID NO 15
<211> LENGTH: 352
<212> TYPE: PRT
<213> ORGANISM: Zika Virus

<400> SEQUENCE: 15

Asp Val Gly Cys Ser Val Asp Phe Ser Lys Lys Glu Thr Arg Cys Gly
1               5                   10                  15

Thr Gly Val Phe Val Tyr Asn Asp Val Glu Ala Trp Arg Asp Arg Tyr
                20                  25                  30

Lys Tyr His Pro Asp Ser Pro Arg Arg Leu Ala Ala Ala Val Lys Gln
            35                  40                  45

Ala Trp Glu Asp Gly Ile Cys Gly Ile Ser Ser Val Ser Arg Met Glu
        50                  55                  60

Asn Ile Met Trp Arg Ser Val Glu Gly Glu Leu Asn Ala Ile Leu Glu
65                  70                  75                  80

Glu Asn Gly Val Gln Leu Thr Val Val Gly Ser Val Lys Asn Pro
                85                  90                  95

Met Trp Arg Gly Pro Gln Arg Leu Pro Val Pro Val Asn Glu Leu Pro
            100                 105                 110

His Gly Trp Lys Ala Trp Gly Lys Ser His Phe Val Arg Ala Ala Lys
            115                 120                 125

Thr Asn Asn Ser Phe Val Val Asp Gly Asp Thr Leu Lys Glu Cys Pro
        130                 135                 140

```
Leu Lys His Arg Ala Trp Asn Ser Phe Leu Val Glu Asp His Gly Phe
145                 150                 155                 160

Gly Val Phe His Thr Ser Val Trp Leu Lys Val Arg Glu Asp Tyr Ser
            165                 170                 175

Leu Glu Cys Asp Pro Ala Val Ile Gly Thr Ala Val Lys Gly Lys Glu
            180                 185                 190

Ala Val His Ser Asp Leu Gly Tyr Trp Ile Glu Ser Glu Lys Asn Asp
            195                 200                 205

Thr Trp Arg Leu Lys Arg Ala His Leu Ile Glu Met Lys Thr Cys Glu
            210                 215                 220

Trp Pro Lys Ser His Thr Leu Trp Thr Asp Gly Ile Glu Glu Ser Asp
225                 230                 235                 240

Leu Ile Ile Pro Lys Ser Leu Ala Gly Pro Leu Ser His His Asn Thr
            245                 250                 255

Arg Glu Gly Tyr Arg Thr Gln Met Lys Gly Pro Trp His Ser Glu Glu
            260                 265                 270

Leu Glu Ile Arg Phe Glu Glu Cys Pro Gly Thr Lys Val His Val Glu
            275                 280                 285

Glu Thr Cys Gly Thr Arg Gly Pro Ser Leu Arg Ser Thr Thr Ala Ser
            290                 295                 300

Gly Arg Val Ile Glu Glu Trp Cys Cys Arg Glu Cys Thr Met Pro Pro
305                 310                 315                 320

Leu Ser Phe Arg Ala Lys Asp Gly Cys Trp Tyr Gly Met Glu Ile Arg
            325                 330                 335

Pro Arg Lys Glu Pro Glu Ser Asn Leu Val Arg Ser Met Val Thr Ala
            340                 345                 350

<210> SEQ ID NO 16
<211> LENGTH: 352
<212> TYPE: PRT
<213> ORGANISM: Zika Virus

<400> SEQUENCE: 16

Asp Val Gly Cys Ser Val Asp Phe Ser Lys Lys Glu Thr Arg Cys Gly
1               5                   10                  15

Thr Gly Val Phe Val Tyr Asn Asp Val Glu Ala Trp Arg Asp Arg Tyr
            20                  25                  30

Lys Tyr His Pro Asp Ser Pro Arg Arg Leu Ala Ala Ala Val Lys Gln
            35                  40                  45

Ala Trp Glu Asp Gly Ile Cys Gly Ile Ser Ser Val Ser Arg Met Glu
    50                  55                  60

Asn Ile Met Trp Arg Ser Val Glu Gly Glu Leu Asn Ala Ile Leu Glu
65                  70                  75                  80

Glu Asn Gly Val Gln Leu Thr Val Val Gly Ser Val Lys Asn Pro
                85                  90                  95

Met Trp Arg Gly Pro Gln Arg Leu Pro Val Pro Val Asn Glu Leu Pro
            100                 105                 110

His Gly Trp Lys Ala Trp Gly Lys Ser Tyr Phe Val Arg Ala Ala Lys
            115                 120                 125

Thr Asn Asn Ser Phe Val Val Asp Gly Asp Thr Leu Lys Glu Cys Pro
            130                 135                 140

Leu Lys His Arg Ala Trp Asn Ser Phe Leu Val Glu Asp His Gly Phe
145                 150                 155                 160

Gly Val Phe His Thr Ser Val Trp Leu Lys Val Arg Glu Asp Tyr Ser
```

Leu Glu Cys Asp Pro Ala Val Ile Gly Thr Ala Ala Lys Gly Lys Glu
                180                 185                 190

Ala Val His Ser Asp Leu Gly Tyr Trp Ile Glu Ser Glu Lys Asn Asp
                195                 200                 205

Thr Trp Arg Leu Lys Arg Ala His Leu Ile Glu Met Lys Thr Cys Glu
                210                 215                 220

Trp Pro Lys Ser His Thr Leu Trp Thr Asp Gly Ile Glu Glu Ser Asp
225                 230                 235                 240

Leu Ile Ile Pro Lys Ser Leu Ala Gly Pro Leu Ser His His Asn Thr
                245                 250                 255

Arg Glu Gly Tyr Arg Thr Gln Met Glu Gly Pro Trp His Ser Glu Glu
                260                 265                 270

Leu Glu Ile Arg Phe Glu Glu Cys Pro Gly Thr Lys Val His Val Glu
                275                 280                 285

Glu Thr Cys Gly Thr Arg Gly Pro Ser Leu Arg Ser Thr Thr Ala Ser
                290                 295                 300

Gly Arg Val Ile Glu Glu Trp Cys Cys Arg Glu Cys Thr Met Pro Pro
305                 310                 315                 320

Leu Ser Phe Arg Ala Lys Asp Gly Cys Trp Tyr Gly Met Glu Ile Arg
                325                 330                 335

Pro Arg Lys Glu Pro Glu Ser Asn Leu Val Arg Ser Met Val Thr Ala
                340                 345                 350

<210> SEQ ID NO 17
<211> LENGTH: 352
<212> TYPE: PRT
<213> ORGANISM: Zika Virus

<400> SEQUENCE: 17

Asp Val Gly Cys Ser Val Asp Phe Ser Lys Lys Glu Thr Arg Cys Gly
1               5                   10                  15

Thr Gly Val Phe Val Tyr Asn Asp Val Glu Ala Trp Arg Asp Arg Tyr
                20                  25                  30

Lys Tyr His Pro Asp Ser Pro Arg Arg Leu Ala Ala Ala Val Lys Gln
                35                  40                  45

Ala Trp Glu Asp Gly Ile Cys Gly Ile Ser Ser Val Ser Arg Met Glu
50                  55                  60

Asn Ile Met Trp Arg Ser Val Glu Gly Glu Leu Asn Ala Ile Leu Glu
65                  70                  75                  80

Glu Asn Gly Val Gln Leu Thr Val Val Gly Ser Val Lys Asn Pro
                85                  90                  95

Met Trp Arg Gly Pro Gln Arg Leu Pro Val Pro Val Asn Glu Leu Pro
                100                 105                 110

His Gly Trp Lys Ala Trp Gly Lys Ser Tyr Phe Val Arg Ala Ala Lys
                115                 120                 125

Thr Asn Asn Ser Phe Val Val Asp Gly Asp Thr Leu Lys Glu Cys Pro
130                 135                 140

Leu Lys His Arg Ala Trp Asn Ser Phe Leu Val Glu Asp His Gly Phe
145                 150                 155                 160

Gly Val Phe His Thr Ser Val Trp Leu Lys Val Arg Glu Asp Tyr Ser
                165                 170                 175

Leu Glu Cys Asp Pro Ala Val Ile Gly Thr Ala Ala Lys Gly Lys Glu
                180                 185                 190

```
Ala Val His Ser Asp Leu Gly Tyr Trp Ile Glu Ser Glu Lys Asn Asp
            195                 200                 205

Thr Trp Arg Leu Lys Arg Ala His Leu Ile Glu Met Lys Thr Cys Glu
    210                 215                 220

Trp Pro Lys Ser His Thr Leu Trp Thr Asp Gly Ile Glu Glu Ser Asp
225                 230                 235                 240

Leu Ile Ile Pro Lys Ser Leu Ala Gly Pro Leu Ser His His Asn Thr
                245                 250                 255

Arg Glu Gly Tyr Arg Thr Gln Met Lys Gly Pro Trp His Ser Glu Glu
                260                 265                 270

Leu Glu Ile Arg Phe Glu Glu Cys Pro Gly Thr Lys Val His Val Glu
                275                 280                 285

Glu Thr Cys Gly Thr Arg Gly Pro Ser Leu Arg Ser Thr Thr Ala Ser
    290                 295                 300

Gly Arg Val Ile Glu Glu Trp Cys Cys Arg Glu Cys Thr Met Pro Pro
305                 310                 315                 320

Leu Ser Phe Arg Ala Lys Asp Gly Cys Trp Tyr Gly Met Glu Ile Arg
                325                 330                 335

Pro Arg Lys Glu Pro Glu Ser Asn Leu Val Arg Ser Met Val Thr Ala
                340                 345                 350

<210> SEQ ID NO 18
<211> LENGTH: 15
<212> TYPE: PRT
<213> ORGANISM: Artificial Sequence
<220> FEATURE:
<223> OTHER INFORMATION: Peptide 1

<400> SEQUENCE: 18

Gly Cys Ser Val Asp Phe Ser Lys Lys Glu Thr Arg Cys Gly Thr
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Peptide 2

<400> SEQUENCE: 19

Val Asp Phe Ser Lys Lys Glu Thr Arg Cys Gly Thr Gly Val Phe
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Peptide 3

<400> SEQUENCE: 20

Ser Lys Lys Glu Thr Arg Cys Gly Thr Gly Val Phe Val Tyr Asn
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Peptide 4

<400> SEQUENCE: 21
```

Glu Thr Arg Cys Gly Thr Gly Val Phe Val Tyr Asn Asp Val Glu
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Peptide 5

<400> SEQUENCE: 22

Cys Gly Thr Gly Val Phe Val Tyr Asn Asp Val Glu Ala Trp Arg
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Peptide 6

<400> SEQUENCE: 23

Gly Val Phe Val Tyr Asn Asp Val Glu Ala Trp Arg Asp Arg Tyr
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Peptide 7

<400> SEQUENCE: 24

Val Tyr Asn Asp Val Glu Ala Trp Arg Asp Arg Tyr Lys Tyr His
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Peptide 8

<400> SEQUENCE: 25

Asp Val Glu Ala Trp Arg Asp Arg Tyr Lys Tyr His Pro Asp Ser
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Peptide 9

<400> SEQUENCE: 26

Ala Trp Arg Asp Arg Tyr Lys Tyr His Pro Asp Ser Pro Arg Arg
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Peptide 10

<400> SEQUENCE: 27

Asp Arg Tyr Lys Tyr His Pro Asp Ser Pro Arg Arg Leu Ala Ala

```
<210> SEQ ID NO 28
<211> LENGTH: 15
<212> TYPE: PRT
<213> ORGANISM: Artificial Sequence
<220> FEATURE:
<223> OTHER INFORMATION: Peptide 11

<400> SEQUENCE: 28

Lys Tyr His Pro Asp Ser Pro Arg Arg Leu Ala Ala Ala Val Lys
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Peptide 12

<400> SEQUENCE: 29

Pro Asp Ser Pro Arg Arg Leu Ala Ala Ala Val Lys Gln Ala Trp
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: Peptide 13

<400> SEQUENCE: 30

Pro Arg Arg Leu Ala Ala Ala Val Lys Gln Ala Trp Glu Asp Gly
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Peptide 14

<400> SEQUENCE: 31

Leu Ala Ala Ala Val Lys Gln Ala Trp Glu Asp Gly Ile Cys Gly
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Peptide 15

<400> SEQUENCE: 32

Ala Val Lys Gln Ala Trp Glu Asp Gly Ile Cys Gly Ile Ser Ser
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: Peptide 16

<400> SEQUENCE: 33

Gln Ala Trp Glu Asp Gly Ile Cys Gly Ile Ser Ser Val Ser Arg
1               5                   10                  15
```

```
<210> SEQ ID NO 34
<211> LENGTH: 15
<212> TYPE: PRT
<213> ORGANISM: Artificial Sequence
<220> FEATURE:
<223> OTHER INFORMATION: Peptide 17

<400> SEQUENCE: 34

Glu Asp Gly Ile Cys Gly Ile Ser Ser Val Ser Arg Met Glu Asn
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Peptide 18

<400> SEQUENCE: 35

Ile Cys Gly Ile Ser Ser Val Ser Arg Met Glu Asn Ile Met Trp
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Peptide 19

<400> SEQUENCE: 36

Ile Ser Ser Val Ser Arg Met Glu Asn Ile Met Trp Arg Ser Val
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Peptide 20

<400> SEQUENCE: 37

Val Ser Arg Met Glu Asn Ile Met Trp Arg Ser Val Glu Gly Glu
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: Peptide 21

<400> SEQUENCE: 38

Met Glu Asn Ile Met Trp Arg Ser Val Glu Gly Glu Leu Asn Ala
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: Peptide 22

<400> SEQUENCE: 39

Ile Met Trp Arg Ser Val Glu Gly Glu Leu Asn Ala Ile Leu Glu
1               5                   10                  15
```

```
<210> SEQ ID NO 40
<211> LENGTH: 15
<212> TYPE: PRT
<213> ORGANISM: Artificial Sequence
<220> FEATURE:
<223> OTHER INFORMATION: Peptide 23

<400> SEQUENCE: 40

Arg Ser Val Glu Gly Glu Leu Asn Ala Ile Leu Glu Glu Asn Gly
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Peptide 24

<400> SEQUENCE: 41

Glu Gly Glu Leu Asn Ala Ile Leu Glu Glu Asn Gly Val Gln Leu
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: Peptide 25

<400> SEQUENCE: 42

Leu Asn Ala Ile Leu Glu Glu Asn Gly Val Gln Leu Thr Val Val
1               5                   10                  15

<210> SEQ ID NO 43
<211> LENGTH: 15
<212> TYPE: PRT
<213> ORGANISM: Artificial Sequence
<220> FEATURE:
<223> OTHER INFORMATION: Peptide 26

<400> SEQUENCE: 43

Ile Leu Glu Glu Asn Gly Val Gln Leu Ile Val Val Val Gly Ser
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: Peptide 27

<400> SEQUENCE: 44

Glu Asn Gly Val Gln Leu Thr Val Val Val Gly Ser Val Lys Asn
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: Peptide 28

<400> SEQUENCE: 45

Val Gln Leu Thr Val Val Val Gly Ser Val Lys Asn Pro Met Trp
1               5                   10                  15
```

```
<210> SEQ ID NO 46
<211> LENGTH: 14
<212> TYPE: PRT
<213> ORGANISM: Artificial Sequence
<220> FEATURE:
<223> OTHER INFORMATION: Peptide 29

<400> SEQUENCE: 46

Trp Val Val Gly Ser Val Lys Asn Pro Met Trp Arg Gly Pro
1               5                   10

<210> SEQ ID NO 47
<211> LENGTH: 15
<212> TYPE: PRT
<213> ORGANISM: Artificial Sequence
<220> FEATURE:
<223> OTHER INFORMATION: Peptide 30

<400> SEQUENCE: 47

Val Gly Ser Val Lys Asn Pro Met Trp Arg Gly Pro Gln Arg Leu
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: Peptide 31

<400> SEQUENCE: 48

Val Lys Asn Pro Met Trp Arg Gly Pro Gln Arg Leu Pro Val Pro
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: Peptide 32

<400> SEQUENCE: 49

Pro Met Trp Arg Gly Pro Gln Arg Leu Pro Val Pro Val Asn Glu
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: Peptide 33

<400> SEQUENCE: 50

Arg Gly Pro Gln Arg Leu Pro Val Pro Val Asn Glu Leu Pro His
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: Peptide 34

<400> SEQUENCE: 51

Gln Arg Leu Pro Val Pro Val Asn Glu Leu Pro His Gly Trp Lys
1               5                   10                  15

<210> SEQ ID NO 52
```

```
<211> LENGTH: 15
<212> TYPE: PRT
<213> ORGANISM: Artificial Sequence
<220> FEATURE:
<223> OTHER INFORMATION: Peptide 35

<400> SEQUENCE: 52

Pro Val Pro Val Asn Glu Leu Pro His Gly Trp Lys Ala Trp Gly
 1               5                  10                  15

<210> SEQ ID NO 53
<211> LENGTH: 15
<212> TYPE: PRT
<213> ORGANISM: Artificial Sequence
<220> FEATURE:
<223> OTHER INFORMATION: Peptide 36

<400> SEQUENCE: 53

Val Asn Glu Leu Pro His Gly Trp Lys Ala Trp Gly Lys Ser Tyr
 1               5                  10                  15

<210> SEQ ID NO 54
<211> LENGTH: 15
<212> TYPE: PRT
<213> ORGANISM: Artificial Sequence
<220> FEATURE:
<223> OTHER INFORMATION: Peptide 37

<400> SEQUENCE: 54

Leu Pro His Gly Trp Lys Ala Trp Gly Lys Ser Tyr Phe Val Arg
 1               5                  10                  15

<210> SEQ ID NO 55
<211> LENGTH: 15
<212> TYPE: PRT
<213> ORGANISM: Artificial Sequence
<220> FEATURE:
<223> OTHER INFORMATION: Peptide 38

<400> SEQUENCE: 55

Gly Trp Lys Ala Trp Gly Lys Ser Tyr Phe Val Arg Ala Ala Lys
 1               5                  10                  15

<210> SEQ ID NO 56
<211> LENGTH: 15
<212> TYPE: PRT
<213> ORGANISM: Artificial Sequence
<220> FEATURE:
<223> OTHER INFORMATION: Peptide 39

<400> SEQUENCE: 56

Ala Trp Gly Lys Ser Tyr Phe Val Arg Ala Ala Lys Thr Asn Asn
 1               5                  10                  15

<210> SEQ ID NO 57
<211> LENGTH: 15
<212> TYPE: PRT
<213> ORGANISM: Artificial Sequence
<220> FEATURE:
<223> OTHER INFORMATION: Peptide 40

<400> SEQUENCE: 57

Lys Ser Tyr Phe Val Arg Ala Ala Lys Thr Asn Asn Ser Phe Val
 1               5                  10                  15

<210> SEQ ID NO 58
<211> LENGTH: 15
```

```
<212> TYPE: PRT
<213> ORGANISM: Artificial Sequence
<220> FEATURE:
<223> OTHER INFORMATION: Peptide 41

<400> SEQUENCE: 58

Phe Val Arg Ala Ala Lys Thr Asn Asn Ser Phe Val Val Asp Gly
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: Peptide 42

<400> SEQUENCE: 59

Ala Ala Lys Thr Asn Asn Ser Phe Val Val Asp Gly Asp Thr Leu
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: Peptide 43

<400> SEQUENCE: 60

Thr Asn Asn Ser Phe Val Val Asp Gly Asp Thr Leu Lys Glu Cys
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: Peptide 44

<400> SEQUENCE: 61

Ser Phe Val Val Asp Gly Asp Thr Leu Lys Glu Cys Pro Leu Lys
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: Peptide 45

<400> SEQUENCE: 62

Val Asp Gly Asp Thr Leu Lys Glu Cys Pro Leu Lys His Arg Ala
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: Peptide 46

<400> SEQUENCE: 63

Asp Thr Leu Lys Glu Cys Pro Leu Lys His Arg Ala Trp Asn Ser
1               5                   10                  15

<210> SEQ ID NO 64
<211> LENGTH: 15
<212> TYPE: PRT
```

```
<213> ORGANISM: Artificial Sequence
<220> FEATURE:
<223> OTHER INFORMATION: Peptide 47

<400> SEQUENCE: 64

Lys Glu Cys Pro Leu Lys His Arg Ala Trp Asn Ser Phe Leu Val
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: Peptide 48

<400> SEQUENCE: 65

Pro Leu Lys His Arg Ala Trp Asn Ser Phe Leu Val Glu Asp His
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: Peptide 49

<400> SEQUENCE: 66

His Arg Ala Trp Asn Ser Phe Leu Val Glu Asp His Gly Phe Gly
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: Peptide 50

<400> SEQUENCE: 67

Trp Asn Ser Phe Leu Val Glu Asp His Gly Phe Gly Val Phe His
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: Peptide 51

<400> SEQUENCE: 68

Phe Leu Val Glu Asp His Gly Phe Gly Val Phe His Thr Ser Val
1               5                   10                  15

<210> SEQ ID NO 69
<211> LENGTH: 15
<212> TYPE: PRT
<213> ORGANISM: Artificial Sequence
<220> FEATURE:
<223> OTHER INFORMATION: Peptide 52

<400> SEQUENCE: 69

Glu Asp His Gly Phe Gly Val Phe His Thr Ser Val Trp Leu Lys
1               5                   10                  15

<210> SEQ ID NO 70
<211> LENGTH: 15
<212> TYPE: PRT
<213> ORGANISM: Artificial Sequence
```

```
<220> FEATURE:
<223> OTHER INFORMATION: Peptide 53

<400> SEQUENCE: 70

Gly Phe Gly Val Phe His Thr Ser Val Trp Leu Lys Val Arg Glu
1               5                   10                  15

<210> SEQ ID NO 71
<211> LENGTH: 15
<212> TYPE: PRT
<213> ORGANISM: Artificial Sequence
<220> FEATURE:
<223> OTHER INFORMATION: Peptide 54

<400> SEQUENCE: 71

Val Phe His Thr Ser Val Trp Leu Lys Val Arg Glu Asp Tyr Ser
1               5                   10                  15

<210> SEQ ID NO 72
<211> LENGTH: 15
<212> TYPE: PRT
<213> ORGANISM: Artificial Sequence
<220> FEATURE:
<223> OTHER INFORMATION: Peptide 55

<400> SEQUENCE: 72

Thr Ser Val Trp Leu Lys Val Arg Glu Asp Tyr Ser Leu Glu Cys
1               5                   10                  15

<210> SEQ ID NO 73
<211> LENGTH: 15
<212> TYPE: PRT
<213> ORGANISM: Artificial Sequence
<220> FEATURE:
<223> OTHER INFORMATION: Peptide 56

<400> SEQUENCE: 73

Trp Leu Lys Val Arg Glu Asp Tyr Ser Leu Glu Cys Asp Pro Ala
1               5                   10                  15

<210> SEQ ID NO 74
<211> LENGTH: 15
<212> TYPE: PRT
<213> ORGANISM: Artificial Sequence
<220> FEATURE:
<223> OTHER INFORMATION: Peptide 57

<400> SEQUENCE: 74

Val Arg Glu Asp Tyr Ser Leu Glu Cys Asp Pro Ala Val Ile Gly
1               5                   10                  15

<210> SEQ ID NO 75
<211> LENGTH: 15
<212> TYPE: PRT
<213> ORGANISM: Artificial Sequence
<220> FEATURE:
<223> OTHER INFORMATION: Peptide 58

<400> SEQUENCE: 75

Asp Tyr Ser Leu Glu Cys Asp Pro Ala Val Ile Gly Thr Ala Val
1               5                   10                  15

<210> SEQ ID NO 76
<211> LENGTH: 15
<212> TYPE: PRT
<213> ORGANISM: Artificial Sequence
<220> FEATURE:
```

<223> OTHER INFORMATION: Peptide 59

<400> SEQUENCE: 76

Leu Glu Cys Asp Pro Ala Val Ile Gly Thr Ala Val Lys Gly Lys
1               5                   10                  15

<210> SEQ ID NO 77
<211> LENGTH: 15
<212> TYPE: PRT
<213> ORGANISM: Artificial Sequence
<220> FEATURE:
<223> OTHER INFORMATION: Peptide 60

<400> SEQUENCE: 77

Asp Pro Ala Val Ile Gly Thr Ala Val Lys Gly Lys Glu Ala Val
1               5                   10                  15

<210> SEQ ID NO 78
<211> LENGTH: 15
<212> TYPE: PRT
<213> ORGANISM: Artificial Sequence
<220> FEATURE:
<223> OTHER INFORMATION: Peptide 61

<400> SEQUENCE: 78

Val Ile Gly Thr Ala Val Lys Gly Lys Glu Ala Val His Ser Asp
1               5                   10                  15

<210> SEQ ID NO 79
<211> LENGTH: 15
<212> TYPE: PRT
<213> ORGANISM: Artificial Sequence
<220> FEATURE:
<223> OTHER INFORMATION: Peptide 62

<400> SEQUENCE: 79

Thr Ala Val Lys Gly Lys Glu Ala Val His Ser Asp Leu Gly Tyr
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: Peptide 63

<400> SEQUENCE: 80

Lys Gly Lys Glu Ala Val His Ser Asp Leu Gly Tyr Trp Ile Glu
1               5                   10                  15

<210> SEQ ID NO 81
<211> LENGTH: 15
<212> TYPE: PRT
<213> ORGANISM: Artificial Sequence
<220> FEATURE:
<223> OTHER INFORMATION: Peptide 64

<400> SEQUENCE: 81

Glu Ala Val His Ser Asp Leu Gly Tyr Trp Ile Glu Ser Glu Lys
1               5                   10                  15

<210> SEQ ID NO 82
<211> LENGTH: 15
<212> TYPE: PRT
<213> ORGANISM: Artificial Sequence
<220> FEATURE:
<223> OTHER INFORMATION: Peptide 65

```
<400> SEQUENCE: 82

His Ser Asp Leu Gly Tyr Trp Ile Glu Ser Glu Lys Asn Asp Thr
1               5                   10                  15

<210> SEQ ID NO 83
<211> LENGTH: 15
<212> TYPE: PRT
<213> ORGANISM: Artificial Sequence
<220> FEATURE:
<223> OTHER INFORMATION: Peptide 66

<400> SEQUENCE: 83

Leu Gly Tyr Trp Ile Glu Ser Glu Lys Asn Asp Thr Trp Arg Leu
1               5                   10                  15

<210> SEQ ID NO 84
<211> LENGTH: 15
<212> TYPE: PRT
<213> ORGANISM: Artificial Sequence
<220> FEATURE:
<223> OTHER INFORMATION: Peptide 67

<400> SEQUENCE: 84

Trp Ile Glu Ser Glu Lys Asn Asp Thr Trp Arg Leu Lys Arg Ala
1               5                   10                  15

<210> SEQ ID NO 85
<211> LENGTH: 15
<212> TYPE: PRT
<213> ORGANISM: Artificial Sequence
<220> FEATURE:
<223> OTHER INFORMATION: Peptide 68

<400> SEQUENCE: 85

Ser Glu Lys Asn Asp Thr Trp Arg Leu Lys Arg Ala His Leu Ile
1               5                   10                  15

<210> SEQ ID NO 86
<211> LENGTH: 15
<212> TYPE: PRT
<213> ORGANISM: Artificial Sequence
<220> FEATURE:
<223> OTHER INFORMATION: Peptide 69

<400> SEQUENCE: 86

Asn Asp Thr Trp Arg Leu Lys Arg Ala His Leu Ile Glu Met Lys
1               5                   10                  15

<210> SEQ ID NO 87
<211> LENGTH: 15
<212> TYPE: PRT
<213> ORGANISM: Artificial Sequence
<220> FEATURE:
<223> OTHER INFORMATION: Peptide 70

<400> SEQUENCE: 87

Trp Arg Leu Lys Arg Ala His Leu Ile Glu Met Lys Thr Cys Glu
1               5                   10                  15

<210> SEQ ID NO 88
<211> LENGTH: 15
<212> TYPE: PRT
<213> ORGANISM: Artificial Sequence
<220> FEATURE:
<223> OTHER INFORMATION: Peptide 71
```

```
<400> SEQUENCE: 88

Lys Arg Ala His Leu Ile Glu Met Lys Thr Cys Glu Trp Pro Lys
1               5                   10                  15

<210> SEQ ID NO 89
<211> LENGTH: 15
<212> TYPE: PRT
<213> ORGANISM: Artificial Sequence
<220> FEATURE:
<223> OTHER INFORMATION: Peptide 72

<400> SEQUENCE: 89

His Leu Ile Glu Met Lys Thr Cys Glu Trp Pro Lys Ser His Thr
1               5                   10                  15

<210> SEQ ID NO 90
<211> LENGTH: 15
<212> TYPE: PRT
<213> ORGANISM: Artificial Sequence
<220> FEATURE:
<223> OTHER INFORMATION: Peptide 73

<400> SEQUENCE: 90

Glu Met Lys Thr Cys Glu Trp Pro Lys Ser His Thr Leu Trp Thr
1               5                   10                  15

<210> SEQ ID NO 91
<211> LENGTH: 15
<212> TYPE: PRT
<213> ORGANISM: Artificial Sequence
<220> FEATURE:
<223> OTHER INFORMATION: Peptide 74

<400> SEQUENCE: 91

Thr Cys Glu Trp Pro Lys Ser His Thr Leu Trp Thr Asp Gly Ile
1               5                   10                  15

<210> SEQ ID NO 92
<211> LENGTH: 15
<212> TYPE: PRT
<213> ORGANISM: Artificial Sequence
<220> FEATURE:
<223> OTHER INFORMATION: Peptide 75

<400> SEQUENCE: 92

Trp Pro Lys Ser His Thr Leu Trp Thr Asp Gly Ile Glu Glu Ser
1               5                   10                  15

<210> SEQ ID NO 93
<211> LENGTH: 15
<212> TYPE: PRT
<213> ORGANISM: Artificial Sequence
<220> FEATURE:
<223> OTHER INFORMATION: Peptide 76

<400> SEQUENCE: 93

Ser His Thr Leu Trp Thr Asp Gly Ile Glu Glu Ser Asp Leu Ile
1               5                   10                  15

<210> SEQ ID NO 94
<211> LENGTH: 15
<212> TYPE: PRT
<213> ORGANISM: Artificial Sequence
<220> FEATURE:
<223> OTHER INFORMATION: Peptide 77

<400> SEQUENCE: 94
```

```
Leu Trp Thr Asp Gly Ile Glu Glu Ser Asp Leu Ile Ile Pro Lys
1               5                   10                  15
```

<210> SEQ ID NO 95
<211> LENGTH: 15
<212> TYPE: PRT
<213> ORGANISM: Artificial Sequence
<220> FEATURE:
<223> OTHER INFORMATION: Peptide 78

<400> SEQUENCE: 95

```
Asp Gly Ile Glu Glu Ser Asp Leu Ile Ile Pro Lys Ser Leu Ala
1               5                   10                  15
```

<210> SEQ ID NO 96
<211> LENGTH: 15
<212> TYPE: PRT
<213> ORGANISM: Artificial Sequence
<220> FEATURE:
<223> OTHER INFORMATION: Peptide 79

<400> SEQUENCE: 96

```
Glu Glu Ser Asp Leu Ile Ile Pro Lys Ser Leu Ala Gly Pro Leu
1               5                   10                  15
```

<210> SEQ ID NO 97
<211> LENGTH: 15
<212> TYPE: PRT
<213> ORGANISM: Artificial Sequence
<220> FEATURE:
<223> OTHER INFORMATION: Peptide 80

<400> SEQUENCE: 97

```
Asp Leu Ile Ile Pro Lys Ser Leu Ala Gly Pro Leu Ser His His
1               5                   10                  15
```

<210> SEQ ID NO 98
<211> LENGTH: 15
<212> TYPE: PRT
<213> ORGANISM: Artificial Sequence
<220> FEATURE:
<223> OTHER INFORMATION: Peptide 81

<400> SEQUENCE: 98

```
Ile Pro Lys Ser Leu Ala Gly Pro Leu Ser His His Asn Thr Arg
1               5                   10                  15
```

<210> SEQ ID NO 99
<211> LENGTH: 15
<212> TYPE: PRT
<213> ORGANISM: Artificial Sequence
<220> FEATURE:
<223> OTHER INFORMATION: Peptide 82

<400> SEQUENCE: 99

```
Ser Leu Ala Gly Pro Leu Ser His His Asn Thr Arg Glu Gly Tyr
1               5                   10                  15
```

<210> SEQ ID NO 100
<211> LENGTH: 15
<212> TYPE: PRT
<213> ORGANISM: Artificial Sequence
<220> FEATURE:
<223> OTHER INFORMATION: Peptide 83

<400> SEQUENCE: 100

```
Gly Pro Leu Ser His His Asn Thr Arg Glu Gly Tyr Arg Thr Gln
1               5                   10                  15
```

<210> SEQ ID NO 101
<211> LENGTH: 15
<212> TYPE: PRT
<213> ORGANISM: Artificial Sequence
<220> FEATURE:
<223> OTHER INFORMATION: Peptide 84

<400> SEQUENCE: 101

```
Ser His His Asn Thr Arg Glu Gly Tyr Arg Thr Gln Met Lys Gly
1               5                   10                  15
```

<210> SEQ ID NO 102
<211> LENGTH: 15
<212> TYPE: PRT
<213> ORGANISM: Artificial Sequence
<220> FEATURE:
<223> OTHER INFORMATION: Peptide 85

<400> SEQUENCE: 102

```
Asn Thr Arg Glu Gly Tyr Arg Thr Gln Met Lys Gly Pro Trp His
1               5                   10                  15
```

<210> SEQ ID NO 103
<211> LENGTH: 15
<212> TYPE: PRT
<213> ORGANISM: Artificial Sequence
<220> FEATURE:
<223> OTHER INFORMATION: Peptide 86

<400> SEQUENCE: 103

```
Glu Gly Tyr Arg Thr Gln Met Lys Gly Pro Trp His Ser Glu Glu
1               5                   10                  15
```

<210> SEQ ID NO 104
<211> LENGTH: 15
<212> TYPE: PRT
<213> ORGANISM: Artificial Sequence
<220> FEATURE:
<223> OTHER INFORMATION: Peptide 87

<400> SEQUENCE: 104

```
Arg Thr Gln Met Lys Gly Pro Trp His Ser Glu Glu Leu Glu Ile
1               5                   10                  15
```

<210> SEQ ID NO 105
<211> LENGTH: 15
<212> TYPE: PRT
<213> ORGANISM: Artificial Sequence
<220> FEATURE:
<223> OTHER INFORMATION: Peptide 88

<400> SEQUENCE: 105

```
Met Lys Gly Pro Trp His Ser Glu Glu Leu Glu Ile Arg Phe Glu
1               5                   10                  15
```

<210> SEQ ID NO 106
<211> LENGTH: 15
<212> TYPE: PRT
<213> ORGANISM: Artificial Sequence
<220> FEATURE:
<223> OTHER INFORMATION: Peptide 89

<400> SEQUENCE: 106

```
Pro Trp His Ser Glu Glu Leu Glu Ile Arg Phe Glu Glu Cys Pro
```

```
1               5                   10                  15
```

<210> SEQ ID NO 107
<211> LENGTH: 15
<212> TYPE: PRT
<213> ORGANISM: Artificial Sequence
<220> FEATURE:
<223> OTHER INFORMATION: Peptide 90

<400> SEQUENCE: 107

```
Ser Glu Glu Leu Glu Ile Arg Phe Glu Glu Cys Pro Gly Thr Lys
1               5                   10                  15
```

<210> SEQ ID NO 108
<211> LENGTH: 15
<212> TYPE: PRT
<213> ORGANISM: Artificial Sequence
<220> FEATURE:
<223> OTHER INFORMATION: Peptide 91

<400> SEQUENCE: 108

```
Leu Glu Ile Arg Phe Glu Glu Cys Pro Gly Thr Lys Val His Val
1               5                   10                  15
```

<210> SEQ ID NO 109
<211> LENGTH: 15
<212> TYPE: PRT
<213> ORGANISM: Artificial Sequence
<220> FEATURE:
<223> OTHER INFORMATION: Peptide 92

<400> SEQUENCE: 109

```
Arg Phe Glu Glu Cys Pro Gly Thr Lys Val His Val Glu Glu Thr
1               5                   10                  15
```

<210> SEQ ID NO 110
<211> LENGTH: 15
<212> TYPE: PRT
<213> ORGANISM: Artificial Sequence
<220> FEATURE:
<223> OTHER INFORMATION: Peptide 93

<400> SEQUENCE: 110

```
Glu Cys Pro Gly Thr Lys Val His Val Glu Glu Thr Cys Gly Thr
1               5                   10                  15
```

<210> SEQ ID NO 111
<211> LENGTH: 15
<212> TYPE: PRT
<213> ORGANISM: Artificial Sequence
<220> FEATURE:
<223> OTHER INFORMATION: Peptide 94

<400> SEQUENCE: 111

```
Gly Thr Lys Val His Val Glu Glu Thr Cys Gly Thr Arg Gly Pro
1               5                   10                  15
```

<210> SEQ ID NO 112
<211> LENGTH: 15
<212> TYPE: PRT
<213> ORGANISM: Artificial Sequence
<220> FEATURE:
<223> OTHER INFORMATION: Peptide 95

<400> SEQUENCE: 112

```
Val His Val Glu Glu Thr Cys Gly Thr Arg Gly Pro Ser Leu Arg
1               5                   10                  15
```

<210> SEQ ID NO 113
<211> LENGTH: 15
<212> TYPE: PRT
<213> ORGANISM: Artificial Sequence
<220> FEATURE:
<223> OTHER INFORMATION: Peptide 96

<400> SEQUENCE: 113

Glu Glu Thr Cys Gly Thr Arg Gly Pro Ser Leu Arg Ser Ile Thr
1               5                   10                  15

<210> SEQ ID NO 114
<211> LENGTH: 15
<212> TYPE: PRT
<213> ORGANISM: Artificial Sequence
<220> FEATURE:
<223> OTHER INFORMATION: Peptide 97

<400> SEQUENCE: 114

Cys Gly Thr Arg Gly Pro Ser Leu Arg Ser Thr Thr Ala Ser Gly
1               5                   10                  15

<210> SEQ ID NO 115
<211> LENGTH: 15
<212> TYPE: PRT
<213> ORGANISM: Artificial Sequence
<220> FEATURE:
<223> OTHER INFORMATION: Peptide 98

<400> SEQUENCE: 115

Arg Gly Pro Ser Leu Arg Ser Thr Thr Ala Ser Gly Arg Val Ile
1               5                   10                  15

<210> SEQ ID NO 116
<211> LENGTH: 15
<212> TYPE: PRT
<213> ORGANISM: Artificial Sequence
<220> FEATURE:
<223> OTHER INFORMATION: Peptide 99

<400> SEQUENCE: 116

Ser Leu Arg Ser Thr Thr Ala Ser Gly Arg Val Ile Glu Glu Trp
1               5                   10                  15

<210> SEQ ID NO 117
<211> LENGTH: 15
<212> TYPE: PRT
<213> ORGANISM: Artificial Sequence
<220> FEATURE:
<223> OTHER INFORMATION: Peptide 100

<400> SEQUENCE: 117

Ser Thr Thr Ala Ser Gly Arg Val Ile Glu Glu Trp Cys Cys Arg
1               5                   10                  15

<210> SEQ ID NO 118
<211> LENGTH: 15
<212> TYPE: PRT
<213> ORGANISM: Artificial Sequence
<220> FEATURE:
<223> OTHER INFORMATION: Peptide 101

<400> SEQUENCE: 118

Ala Ser Gly Arg Val Ile Glu Glu Trp Cys Cys Arg Glu Cys Thr
1               5                   10                  15

<210> SEQ ID NO 119
<211> LENGTH: 15
<212> TYPE: PRT
<213> ORGANISM: Artificial Sequence
<220> FEATURE:
<223> OTHER INFORMATION: Peptide 102

<400> SEQUENCE: 119

Arg Val Ile Glu Glu Trp Cys Cys Arg Glu Cys Thr Met Pro Pro
1               5                   10                  15

<210> SEQ ID NO 120
<211> LENGTH: 15
<212> TYPE: PRT
<213> ORGANISM: Artificial Sequence
<220> FEATURE:
<223> OTHER INFORMATION: Peptide 103

<400> SEQUENCE: 120

Glu Glu Trp Cys Cys Arg Glu Cys Thr Met Pro Pro Leu Ser Phe
1               5                   10                  15

<210> SEQ ID NO 121
<211> LENGTH: 15
<212> TYPE: PRT
<213> ORGANISM: Artificial Sequence
<220> FEATURE:
<223> OTHER INFORMATION: Peptide 104

<400> SEQUENCE: 121

Cys Cys Arg Glu Cys Thr Met Pro Pro Leu Ser Phe Arg Ala Lys
1               5                   10                  15

<210> SEQ ID NO 122
<211> LENGTH: 15
<212> TYPE: PRT
<213> ORGANISM: Artificial Sequence
<220> FEATURE:
<223> OTHER INFORMATION: Peptide 105

<400> SEQUENCE: 122

Glu Cys Thr Met Pro Pro Leu Ser Phe Arg Ala Lys Asp Gly Cys
1               5                   10                  15

<210> SEQ ID NO 123
<211> LENGTH: 15
<212> TYPE: PRT
<213> ORGANISM: Artificial Sequence
<220> FEATURE:
<223> OTHER INFORMATION: Peptide 106

<400> SEQUENCE: 123

Met Pro Pro Leu Ser Phe Arg Ala Lys Asp Gly Cys Trp Tyr Gly
1               5                   10                  15

<210> SEQ ID NO 124
<211> LENGTH: 15
<212> TYPE: PRT
<213> ORGANISM: Artificial Sequence
<220> FEATURE:
<223> OTHER INFORMATION: Peptide 107

<400> SEQUENCE: 124

Leu Ser Phe Arg Ala Lys Asp Gly Cys Trp Tyr Gly Met Glu Ile
1               5                   10                  15

```
<210> SEQ ID NO 125
<211> LENGTH: 15
<212> TYPE: PRT
<213> ORGANISM: Artificial Sequence
<220> FEATURE:
<223> OTHER INFORMATION: Peptide 108

<400> SEQUENCE: 125

Arg Ala Lys Asp Gly Cys Trp Tyr Gly Met Glu Ile Arg Pro Arg
1               5                   10                  15

<210> SEQ ID NO 126
<211> LENGTH: 15
<212> TYPE: PRT
<213> ORGANISM: Artificial Sequence
<220> FEATURE:
<223> OTHER INFORMATION: Peptide 109

<400> SEQUENCE: 126

Asp Gly Cys Trp Tyr Gly Met Glu Ile Arg Pro Arg Lys Glu Pro
1               5                   10                  15

<210> SEQ ID NO 127
<211> LENGTH: 15
<212> TYPE: PRT
<213> ORGANISM: Artificial Sequence
<220> FEATURE:
<223> OTHER INFORMATION: Peptide 110

<400> SEQUENCE: 127

Trp Tyr Gly Met Glu Ile Arg Pro Arg Lys Glu Pro Glu Ser Asn
1               5                   10                  15

<210> SEQ ID NO 128
<211> LENGTH: 15
<212> TYPE: PRT
<213> ORGANISM: Artificial Sequence
<220> FEATURE:
<223> OTHER INFORMATION: Peptide 111

<400> SEQUENCE: 128

Met Glu Ile Arg Pro Arg Lys Glu Pro Glu Ser Asn Leu Val Arg
1               5                   10                  15

<210> SEQ ID NO 129
<211> LENGTH: 15
<212> TYPE: PRT
<213> ORGANISM: Artificial Sequence
<220> FEATURE:
<223> OTHER INFORMATION: Peptide 112

<400> SEQUENCE: 129

Arg Pro Arg Lys Glu Pro Glu Ser Asn Leu Val Arg Ser Met Val
1               5                   10                  15

<210> SEQ ID NO 130
<211> LENGTH: 15
<212> TYPE: PRT
<213> ORGANISM: Artificial Sequence
<220> FEATURE:
<223> OTHER INFORMATION: Peptide 113

<400> SEQUENCE: 130

Lys Glu Pro Glu Ser Asn Leu Val Arg Ser Met Val Thr Ala Gly
1               5                   10                  15

<210> SEQ ID NO 131
```

```
<211> LENGTH: 13
<212> TYPE: PRT
<213> ORGANISM: Artificial Sequence
<220> FEATURE:
<223> OTHER INFORMATION: Peptide 114

<400> SEQUENCE: 131

Glu Ser Asn Leu Val Arg Ser Met Val Thr Ala Gly Ser
1               5                   10
```